(12) United States Patent
Cote et al.

(10) Patent No.: US 10,745,675 B2
(45) Date of Patent: Aug. 18, 2020

(54) MODIFIED ENZYMES FOR PRODUCING INCREASED ISOMELEZITOSE

(71) Applicant: The United States of America, as represented by the Secretary of Agriculture, Washington, DC (US)

(72) Inventors: Gregory L. Cote, Edwards, IL (US); Christopher D. Skory, Washington, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/966,294

(22) Filed: Apr. 30, 2018

(65) Prior Publication Data

US 2018/0320149 A1 Nov. 8, 2018

Related U.S. Application Data

(60) Provisional application No. 62/500,104, filed on May 2, 2017.

(51) Int. Cl.
| | |
|---|---|
| *C12N 9/10* | (2006.01) |
| *C12P 19/18* | (2006.01) |
| *C12P 19/00* | (2006.01) |

(52) U.S. Cl.
CPC ............ *C12N 9/1051* (2013.01); *C12P 19/00* (2013.01); *C12P 19/18* (2013.01); *C12Y 204/01005* (2013.01)

(58) Field of Classification Search
None
See application file for complete search history.

(56) References Cited

U.S. PATENT DOCUMENTS

| | | | |
|---|---|---|---|
| 2012/0225458 A1 | 9/2012 | Pelzer et al. | |
| 2015/0218532 A1 | 8/2015 | Cote et al. | |
| 2016/0122445 A1* | 5/2016 | Nambiar | ............. C08B 37/0021 514/59 |

OTHER PUBLICATIONS

Li et al. Biotechnol Bioeng. Jul. 2014;111(7):1273-87. Epub May 6, 2014. (Year: 2014).*
Bornscheuer et al. Curr Protoc Protein Sci. Nov. 2011;Chapter 26:Unit26.7. (Year: 2011).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Accession Q03VD3. Nov. 14, 2006 (Year: 2006).*
Accession Q03VD8. Nov. 14, 2006. (Year: 2006).*
Accession Q9RE05. May 1, 2000 (Year: 2000).*
Accession P27470. Aug. 1, 1992 (Year: 1992).*
Accession BCQ31103. Jun. 30, 2016 (Year: 2016).*
Cote, Gregory et al., Isomelezitose formation by glucansucrases, Carbohydrate Research, (2017), 439:57-60.
Cote, Gregory et al., Cloning, expression, and characterization of an insoluble glucan-producing glucansucrase from Leuconostoc mesenteroides NRRL B-1118, Appl Microbiol, (2012), 93:2387-2394.
Hellmuth, Hendrik et al., Engineering the Glucansucrase GTFR Enzyme Reaction and Glycosidic Bond Specificity: Toward Tailor-Made Polymer and Oligosaccharide Products, Biochemistry, (2008), 47:6678-6684.
Malten, Marco et al., Production and Secretion of Recombinant Leuonostoc mesenteroides Dextransucrase DsrS in Bacillus megaterium, Wiley InterScience, (2004), pp. 206-218.
Meng, Xiangfeng et al., Residue Leu940 Has a Crucial Role in the Linkage and Reaction Specificity of the Glucansucrase GTF180 of the Probiotic Bacterium Lactobacillus reuteri 180*, The Journal of Biological Chemistry, (2014), 289(47): 32773-32782.
Meng, Xiangfeng et al., Characterization of the Functional Roles of Amino Acid Residues in Acceptor Binding Subsite +1 in the Active Site of the Glucansucrase GTF180 from Lactobacillus reuteri 180, JBC Papers in Press. Published in Oct. 27, 2015 as Manuscript M115.687558, The American Society for Biochemistry and Molwcular Biology, Inc., (2015), pp. 1-23.
Meng, Xiangfeng et al.,Truncation of domain V of the multidomain glucansucrase GTF180 of Lactobacillus reuteri 180 heavily impairs its polysaccharide-synthesizing ability, Appl Microbiol Biotechnol, Springer, Published On-line (2015), pp. 10.
Moulis, Claire et al., Understanding the Polymerization Mechanism of Glycoside-Hydrolase Family 70 Glucansucrases*, The Journal of Biological Chemistry, (2006), 281(42): 31254-31267.
Skory, Christopher et al., Secreted expression of Leuconostoc mesenteroides glucansucrase in Lactococcus lactis for the production of insoluble glucans, Appl Microbiol Biotechnol, (2015), 99:10001-10010.
Meng, Xiangfeng et al., Characterization of the Functional Roles of Amino Acid Residues in Acceptor Binding Subsite +1 in the Active Site of the Glucansucrase GTF180 from Lactobacillus retaieri 180, JBC Papers in Press. Published on Oct. 27, 2015 as Manuscript M115.687558, The The American Society for Biochemisiry and Molecular Biology, Inc., (2015), pp. 10.
Cote, Gregory et al., "Effects of mutations at threonine-654 on the insoluble glucan synthesized by Leuconostoc mesenteroides NRRL B-1118 glucansucrase," Appl Biotechnol, (2014), 98:6651-6658.
Cote, Gregory et al., "Effect of a single point mutation on the interaction of glucans with a glucansucrase from Leuconostoc mesenteroides NRRL B-1118," Carbohydrate Research, (2016), 428:57-61.
Cote, Gregory et al., "Isomelezitose formation by glucansucrases," Carboyhdrate Research, (2017), 439:57-60.

(Continued)

*Primary Examiner* — Christian L Fronda
(74) *Attorney, Agent, or Firm* — John D. Fado; Mark D. McNemar

(57) ABSTRACT

Provided herein are compositions and methods for the synthesis of the trisaccharide, isomelezitose, using genetically modified glucansucrase enzymes from representative microorganisms, including lactic acid bacteria such as *Leuconostoc mesenteroides*. Various modified enzymes are detailed, increasing isomelezitose yields and provide the foundation for large-scale production of isomelezitose for food, industrial and biomedical applications.

17 Claims, 6 Drawing Sheets

Specification includes a Sequence Listing.

(56) References Cited

OTHER PUBLICATIONS

Cote, Gregory et al., "Production of isomelezitose from sucrose by engineered glucansucrases," Amylase, (2017), 1:82-93.
International Searching Authority, PCT/US2018/030373 for The United States of America, as Represented by the Secretary of Agriculture, International Filing Date May 1, 2018.

* cited by examiner

```
                            *
GTF180  WNKDSENVDYGGL-QLQGGELKYVN
DsrI    WNIASES--KGTD-HLQGGALLYVN
DsrS    WNETSED--MSND-HLQNGALTYVN
GtfI    WNGESEK--PYDD-HLQNGALLFDN
GtfG    WNEVSES--PSND-HLQGGALTYVN
Asr     WNKQTEDEAFDGLQWLQGGFLAYQD
```

FIG. 1

ID NO:5) in the domain

SEQUENCE LISTING

<160> NUMBER OF SEQ ID NOS: 21

<210> SEQ ID NO 1
<211> LENGTH: 6174
<212> TYPE: DNA
<213> ORGANISM: Leuconostoc citreum

<400> SEQUENCE: 1

```
atgaaacaac aagaaacagt tacccgtaaa aaactttata aatccggtaa ggtttgggtt      60
gcagcagcta ctgcatttgc ggtattgggg gtttcaactg taacaacagt ccatgcggat     120
acaaattcga atgtcgctgt taagcaaata aataatacag gaaccaatga ttctggcgaa     180
aaaaaggtac cggttccatc aactaataat gatagtttga agcaaggaac agatggtttt     240
tggtatgatt cagacggcaa tcgtgtcgat cagaagacca atcagattct gcttactgcg     300
gaacaactta aaaaaaataa cgaaaaaaat ttatcagtaa tcagtgatga tacatcaaaa     360
aaagatgatg aaaatatttc taagcagacc aaaaattgcta atcaacaaac agtagatact     420
gctaaaggcc tgactaccag taatttatct gatcccatca ctgggggtca ctatgaaaat     480
cacaatggct actttgttta tatagatgct tcaggaaaac aagtaacagg tttgcaaaat     540
attgatggta atttacaata ttttgatgac aatggatatc aagtcaaggg atccttccga     600
gatgtcaacg gcaagcatat ctattttgat tcagtaacag ggaaagctag ttcaaatgtt     660
gatattgtta acggtaaagc tcaaggatat gatgcgcaag gcaaccaatt aaagaaaagt     720
tatgtcgccg atagttctgg gcaaacttac tattttgatg gtaatggcca accgttaatc     780
ggcttgcaaa caattgatgg gaacctacaa tattttaacc aacaaggggt tcaaataaag     840
ggtggtttcc aagatgttaa caataaacgt atttattttg caccaaacac aggtaatgcc     900
gttgccaata ctgaaataat aacggtaaaa ttacaggggc gtgacgcaaa tggtaaccag     960
gtaaagaatg catttagtaa agatgttgca ggaaatacat tttattttga cgcaaacggt    1020
gtgatgttaa cagggttgca aactatttca ggaaagacat attatcttga tgaacaagga    1080
cacctgagaa aaaattacgc gggaacattc aataatcagt ttatgtactt cgatgctgat    1140
acaggtgcgg gtaaaacagc gattgaatat caatttgatc aaggattggt atcacaaagt    1200
aatgaaaata ctcctcacaa tgccgcaaag tcttatgata aaagtagttt tgaaaatgtt    1260
gatggttact aacagcaga tacatggtat cgtccaaccg atattttaaa aaatggagat    1320
acttggacgg catctaccga aactgatatg cgtccgcttt taatgacatg gtggcctgac    1380
aaacaaacac aagcaaatta cttgaattttt atgtctagta aaggacttgg tataacgacc    1440
acttatacag cagctacgtc acaaaaaaca ctaaatgacg cagcctttgt tattcaaaca    1500
gcaattgaac aacaaatatc tttgaaaaaa agtactgagt ggttacgtga tgcaattgat    1560
agttttgtga agacgcaagc taattggaat aagcaaacag aagatgaagc tttcgatggt    1620
ttgcagtggc ttcaagggg attcctagct tatcaagatg attcacatcg gacgccgaat    1680
actgattcag gaaataacag aaaactagga cgtcaaccaa ttaatatcga tggttcgaaa    1740
gatacaactg atggtaaagg ctctgaattc ttattagcta cgatattga caactcaaat    1800
ccgattgttc aagctgagca attaaactgg ctacactatt taatgaattt tggtagtatt    1860
acaggtaata atgacaatgc gaattttgat ggcattcgtg tagatgctgt tgataatgtt    1920
gatgctgatt tactaaaaat agctggcgat tatttttaaag ctctatatgg tacagataaa    1980
agcgacgcca atgccaataa gcatttgtct attttagaag actggaacgg taagatcct     2040
cagtatgtta atcaacaggg caatgcgcaa ttaacaatgg attacacagt tacttcacag    2100
```

```
tttggcaatt ctctaacaca tggcgccaac aacaggagta acatgtggta tttcttagat    2160
actggctatt atcttaatgg agatcttaat aagaagatag tagataagaa ccgtccaaat    2220
tctggcactt tggttaacag aattgctaat tcaggtgata caaaagttat tccaaattat    2280
agttttgtta gagcacatga ttcgatgct  caagatccaa ttagaaaagc catgattgat    2340
catggtatta ttaaaaacat gcaggatact ttcactttg  accaactggc tcagggaatg    2400
gaattctact ataagatca  agagaatccg tctggtttca aaaagtataa cgattataac    2460
ttacctagtg cttatgcaat gttgttgact aataaggata ctgtacctcg tgtctattat    2520
ggagatatgt acctcgaagg cgggcaatat atggaaaaag ggacgattta caatcctgtc    2580
atttcagcgt tgctcaaagc tagaataaaa tatgtttctg gtgggcaaac aatggctacc    2640
gatagttctg aaaagacct  taagatggc  gaaactgatt tgttaacaag tgttcgattt    2700
ggtaaaggaa ttatgacatc agatcaaacc acaacacaag acaatagcca agattataaa    2760
aatcgaggca tcggtgtcat tgttggtaat aaccctgacc ttaagttgaa caatgataag    2820
accattacct tgcatatggg aaaggcgcat aagaatcaac tttaccgtgc cttagtatta    2880
tcaaatgact caggaattga tgtttatgat agtgatgata aagcaccaac tttgagaaca    2940
aatgacaacg gtgacttgat tttccataag acaaatacgt ttgtgaagca agatggaact    3000
attataaatt acgaaatgaa gggatcatta aatgctttaa tttcaggtta tttaggtgtc    3060
tgggtgccag ttggagctag tgattcacaa gatgctcgta cagtggcaac tgagtcatca    3120
tcaagtaatg atggttctgt attccattca aatgctgcat tagattctaa tgttatatat    3180
gaaggctttt caaactttca agcgatgccg acttctcctg agcaaagtac aaatgttgtt    3240
attgcaacaa aggctaactt atttaaagaa ttaggtatta ctagttttga gttagcaccct    3300 caatataggt ctagtggtga cactaattac ggtggcatgt cattcttaga ttctttctta    3360
aataatggtt atgcatttac cgatagatat gatttaggct ttaacaaagc agacgggaat    3420
cctaacccaa caaagtatgg aacagatcaa gatttacgta atgcaataga ggcattacac    3480
aaaaacggca tgcaggctat agctgattgg gttcctgacc aaatatatgc tttaccagga    3540
aaggaagttg ttaccgctac tagagtagac gaacggggaa atcaactaaa agacacagat    3600
tttgtcaact tactctatgt tgctaatact aaaagtagtg gtgtggatta tcaggcaaag    3660
tatggcggcg aattttaga  taaattaaga gaagagtacc catcgttatt caaacagaac    3720
caagtatcga caggtcagcc aattgatgct tctacaaaaa ttaagcaatg gtcagctaaa    3780
tatatgaatg ggaccaatat tttacatcga ggtgcttatt atgttttgaa agactgggct    3840
actaaccagt attttaacat tgcaaaaacg aatgaagtat ttttgccact acagttgcag    3900
aataaagatg cgcaaactgg tttcattagt gatgcctccg gtgtaaaata ttactcaatt    3960
agtggttatc aagcaaaaga tacttttatt gaagatggta atgggaattg gtattacttt    4020
gataaagatg gttacatggt gcgttcgcag caaggagaaa atcctataag aacagtcgaa    4080
actagtgtca acacacgaaa cggtaattat tactttatgc caaatggtgt cgagttgcgc    4140
aaaggctttg gaacggataa tagtggtaat gtctattatt ttgatgatca aggtaagatg    4200
gtgagagata aatacattaa cgatgatgct aataatttt  atcacttaaa tgttgatggg    4260
actatgtctc gaggactatt taaatttgat tctgatactc tacagtattt tgctagtaat    4320
ggtgtccaaa taaagatag  ttatgcgaag gatagtaaag gcaataaata ttattttgac    4380
tcagctacag gaaataacga tactgggaaa gcccaaactt gggatggtaa tggctactat    4440
```

```
attactattg attctgatgc gaacaataca attggggtta acacagacta cactgcctac    4500
atcactagct cgctgcgcga agatggctta tttgctaacg caccttacgg tgttgtaaca    4560
aaagaccaaa atggtaacga tcttaagtgg cagtatatta accatacgaa acagtacgaa    4620
gggcaacaag tgcaagtcac gcgtcaatac acagacagta agggagtcag ctggaactta    4680
attacctttg ctggtggtga tttacaagga caaaggcttt gggtggatag tcgtgcgtta    4740
actatgacac catttaaaac gatgaaccaa ataagcttca ttagttatgc taaccgcaat    4800
gatgggttgt ttttgaatgc gccataccaa gtcaaggggt atcaattagc tgggatgtcc    4860
aaccaataca agggccaaca agtgaccatt gctggggtgg cgaacgtttc tggaaaagac    4920
tggagtctga ttagttttaa tgggacacag tactggattg atagtcaggc attgaatacc    4980
aatttcacac atgacatgaa ccaaaaggtc tttgtcaata aactagtaa tcttgatggg    5040 ttattcttaa atgcgccata ccgtcaaccg ggttataagt tagccggttt ggctaaaaat    5100
tacaacaacc aaacggttac tgttagtcaa cagtactttg atgatcaagg cacggtctgg    5160
agtcaggttg tccttggggg tcagacggtc tgggttgata accatgcatt ggcacagatg    5220
caagttagtg atacagacca acagctctat gtgaatagca atggtcggaa tgatgggtta    5280
ttcttgaatg cgccatatcg tggtcaaggg tcacaactga taggcatgac ggcagattat    5340
aatgggcaac atgtacaagt gaccaagcaa gggcaagatg cctatggtgc acaatggcgt    5400
cttattacgc taaataatca acaggtctgg gttgatagtc gcgctttgag cacaacaatc    5460
atgcaagcca tgaatgataa tatgtatgta aatagcagcc aacggacaga tggcttgtgg    5520
ttaaacgcac cttatacgat gagtgggggct aaatgggctg gtgatacacg ttcagctaat    5580
gggcgctatg tccatatttc aaaagcttat tcaaacgaag tcggcaatac atattacttg    5640
acgaatttga atggtcaaag cacatggatt gacaagcggg cgtttactgt gaccttcgat    5700
caggtggtgg cattaaatgc aacgattgtg gcacgccaac gaccagatgg gatgtttaag    5760
acagcaccat atggtgaagc gggggcgcag tttgtcgatt atgtgacaaa ctataaccag    5820
caaaccgtgc cagtaacaaa gcaacattca gatgctcagg gaatcaatg gtacttagcg    5880 acagtgaatg ggacacaata ctggattgat caacggtcat tttcaccagt agtaacgaag    5940
gtggttgatt atcaagctaa gattgtgcca cggacaacac gtgatggtgt gtttagtggc    6000
gcaccctatg gggaagtgaa tgctaagcta gttaacatgg caactgcgta tcaaaatcaa    6060
gttgtccatg cgacagggga atatacgaat gcttcaggga tcacatggag tcagttcgcg    6120
ttaagcgggc aagaagacaa gctatggatt gataagcgtg ctttgcaagc ttaa          6174
```

<210> SEQ ID NO 2
<211> LENGTH: 2057
<212> TYPE: PRT
<213> ORGANISM: Leuconostoc citreum

<400> SEQUENCE: 2

Met Lys Gln Gln Glu Thr Val Thr Arg Lys Lys Leu Tyr Lys Ser Gly
1               5                   10                  15

Lys Val Trp Val Ala Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe

```
            65                  70                  75                  80
Trp Tyr Asp Ser Asp Gly Asn Arg Val Asp Gln Lys Thr Asn Gln Ile
                85                  90                  95

Leu Leu Thr Ala Glu Gln Leu Lys Lys Asn Glu Lys Asn Leu Ser
            100                 105                 110

Val Ile Ser Asp Asp Thr Ser Lys Asp Glu Asn Ile Ser Lys
            115                 120                 125

Gln Thr Lys Ile Ala Asn Gln Gln Thr Val Asp Thr Ala Lys Gly Leu
        130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asn Gly
            180                 185                 190

Tyr Gln Val Lys Gly Ser Phe Arg Asp Val Asn Gly Lys His Ile Tyr
                195                 200                 205

Phe Asp Ser Val Thr Gly Lys Ala Ser Ser Asn Val Asp Ile Val Asn
        210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285

Lys Arg Ile Tyr Phe Ala Pro Asn Thr Gly Asn Ala Val Ala Asn Thr
        290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
        370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
        450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495
```

-continued

Val Ile Gln Thr Ala Ile Glu Gln Gln Ile Ser Leu Lys Lys Ser Thr
            500                 505                 510

Glu Trp Leu Arg Asp Ala Ile Asp Ser Phe Val Lys Thr Gln Ala Asn
        515                 520                 525

Trp Asn Lys Gln Thr Glu Asp Glu Ala Phe Asp Gly Leu Gln Trp Leu
    530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
        595                 600                 605

Asn Trp Leu His Tyr Leu Met Asn Phe Gly Ser Ile Thr Gly Asn Asn
    610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gln Gly Asn
        675                 680                 685

Ala Gln Leu Thr Met Asp Tyr Thr Val Thr Ser Gln Phe Gly Asn Ser
    690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
        755                 760                 765

Asp Ala Gln Asp Pro Ile Arg Lys Ala Met Ile Asp His Gly Ile Ile
    770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
        835                 840                 845

Gln Tyr Met Glu Lys Gly Thr Ile Tyr Asn Pro Val Ile Ser Ala Leu
    850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
                885                 890                 895

Ser Val Arg Phe Gly Lys Gly Ile Met Thr Ser Asp Gln Thr Thr Thr
            900                 905                 910

```
Gln Asp Asn Ser Gln Asp Tyr Lys Asn Arg Gly Ile Gly Val Ile Val
        915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
            965                 970                 975

Thr Leu Arg Thr Asn Asp Asn Gly Asp Leu Ile Phe His Lys Thr Asn
        980                 985                 990

Thr Phe Val Lys Gln Asp Gly Thr Ile Ile Asn Tyr Glu Met Lys Gly
        995                 1000                1005

Ser Leu Asn Ala Leu Ile Ser Gly Tyr Leu Gly Val Trp Val Pro
        1010                1015                1020

Val Gly Ala Ser Asp Ser Gln Asp Ala Arg Thr Val Ala Thr Glu
        1025                1030                1035

Ser Ser Ser Ser Asn Asp Gly Ser Val Phe His Ser Asn Ala Ala
        1040                1045                1050

Leu Asp Ser Asn Val Ile Tyr Glu Gly Phe Ser Asn Phe Gln Ala
        1055                1060                1065

Met Pro Thr Ser Pro Glu Gln Ser Thr Asn Val Ile Ala Thr
        1070                1075                1080

Lys Ala Asn Leu Phe Lys Glu Leu Gly Ile Thr Ser Phe Glu Leu
        1085                1090                1095

Ala Pro Gln Tyr Arg Ser Ser Gly Asp Thr Asn Tyr Gly Gly Met
        1100                1105                1110

Ser Phe Leu Asp Ser Phe Leu Asn Asn Gly Tyr Ala Phe Thr Asp
        1115                1120                1125

Arg Tyr Asp Leu Gly Phe Asn Lys Ala Asp Gly Asn Pro Asn Pro
        1130                1135                1140

Thr Lys Tyr Gly Thr Asp Gln Asp Leu Arg Asn Ala Ile Glu Ala
        1145                1150                1155

Leu His Lys Asn Gly Met Gln Ala Ile Ala Asp Trp Val Pro Asp
        1160                1165                1170

Gln Ile Tyr Ala Leu Pro Gly Lys Glu Val Val Thr Ala Thr Arg
        1175                1180                1185

Val Asp Glu Arg Gly Asn Gln Leu Lys Asp Thr Asp Phe Val Asn
        1190                1195                1200

Leu Leu Tyr Val Ala Asn Thr Lys Ser Ser Gly Val Asp Tyr Gln
        1205                1210                1215

Ala Lys Tyr Gly Gly Glu Phe Leu Asp Lys Leu Arg Glu Glu Tyr
        1220                1225                1230

Pro Ser Leu Phe Lys Gln Asn Gln Val Ser Thr Gly Gln Pro Ile
        1235                1240                1245

Asp Ala Ser Thr Lys Ile Lys Gln Trp Ser Ala Lys Tyr Met Asn
        1250                1255                1260

Gly Thr Asn Ile Leu His Arg Gly Ala Tyr Tyr Val Leu Lys Asp
        1265                1270                1275

Trp Ala Thr Asn Gln Tyr Phe Asn Ile Ala Lys Thr Asn Glu Val
        1280                1285                1290

Phe Leu Pro Leu Gln Leu Gln Asn Lys Asp Ala Gln Thr Gly Phe
        1295                1300                1305

Ile Ser Asp Ala Ser Gly Val Lys Tyr Tyr Ser Ile Ser Gly Tyr
```

-continued

```
            1310                1315                1320
Gln Ala Lys Asp Thr Phe Ile Glu Asp Gly Asn Gly Asn Trp Tyr
        1325                1330                1335
Tyr Phe Asp Lys Asp Gly Tyr Met Val Arg Ser Gln Gln Gly Glu
        1340                1345                1350
Asn Pro Ile Arg Thr Val Glu Thr Ser Val Asn Thr Arg Asn Gly
        1355                1360                1365
Asn Tyr Tyr Phe Met Pro Asn Gly Val Glu Leu Arg Lys Gly Phe
        1370                1375                1380
Gly Thr Asp Asn Ser Gly Asn Val Tyr Tyr Phe Asp Asp Gln Gly
        1385                1390                1395
Lys Met Val Arg Asp Lys Tyr Ile Asn Asp Asp Ala Asn Asn Phe
        1400                1405                1410
Tyr His Leu Asn Val Asp Gly Thr Met Ser Arg Gly Leu Phe Lys
        1415                1420                1425
Phe Asp Ser Asp Thr Leu Gln Tyr Phe Ala Ser Asn Gly Val Gln
        1430                1435                1440
Ile Lys Asp Ser Tyr Ala Lys Asp Ser Lys Gly Asn Lys Tyr Tyr
        1445                1450                1455
Phe Asp Ser Ala Thr Gly Asn Asn Asp Thr Gly Lys Ala Gln Thr
        1460                1465                1470
Trp Asp Gly Asn Gly Tyr Tyr Ile Thr Ile Asp Ser Asp Ala Asn
        1475                1480                1485
Asn Thr Ile Gly Val Asn Thr Asp Tyr Thr Ala Tyr Ile Thr Ser
        1490                1495                1500
Ser Leu Arg Glu Asp Gly Leu Phe Ala Asn Ala Pro Tyr Gly Val
        1505                1510                1515
Val Thr Lys Asp Gln Asn Gly Asn Asp Leu Lys Trp Gln Tyr Ile
        1520                1525                1530
Asn His Thr Lys Gln Tyr Glu Gly Gln Gln Val Gln Val Thr Arg
        1535                1540                1545
Gln Tyr Thr Asp Ser Lys Gly Val Ser Trp Asn Leu Ile Thr Phe
        1550                1555                1560
Ala Gly Gly Asp Leu Gln Gly Gln Arg Leu Trp Val Asp Ser Arg
        1565                1570                1575
Ala Leu Thr Met Thr Pro Phe Lys Thr Met Asn Gln Ile Ser Phe
        1580                1585                1590
Ile Ser Tyr Ala Asn Arg Asn Asp Gly Leu Phe Leu Asn Ala Pro
        1595                1600                1605
Tyr Gln Val Lys Gly Tyr Gln Leu Ala Gly Met Ser Asn Gln Tyr
        1610                1615                1620
Lys Gly Gln Gln Val Thr Ile Ala Gly Val Ala Asn Val Ser Gly
        1625                1630                1635
Lys Asp Trp Ser Leu Ile Ser Phe Asn Gly Thr Gln Tyr Trp Ile
        1640                1645                1650
Asp Ser Gln Ala Leu Asn Thr Asn Phe Thr His Asp Met Asn Gln
        1655                1660                1665
Lys Val Phe Val Asn Thr Thr Ser Asn Leu Asp Gly Leu Phe Leu
        1670                1675                1680
Asn Ala Pro Tyr Arg Gln Pro Gly Tyr Lys Leu Ala Gly Leu Ala
        1685                1690                1695
Lys Asn Tyr Asn Asn Gln Thr Val Thr Val Ser Gln Gln Tyr Phe
        1700                1705                1710
```

-continued

Asp Asp Gln Gly Thr Val Trp Ser Gln Val Val Leu Gly Gly Gln
    1715                1720                1725

Thr Val Trp Val Asp Asn His Ala Leu Ala Gln Met Gln Val Ser
    1730                1735                1740

Asp Thr Asp Gln Gln Leu Tyr Val Asn Ser Asn Gly Arg Asn Asp
    1745                1750                1755

Gly Leu Phe Leu Asn Ala Pro Tyr Arg Gly Gln Gly Ser Gln Leu
    1760                1765                1770

Ile Gly Met Thr Ala Asp Tyr Asn Gly Gln His Val Gln Val Thr
    1775                1780                1785

Lys Gln Gly Gln Asp Ala Tyr Gly Ala Gln Trp Arg Leu Ile Thr
    1790                1795                1800

Leu Asn Asn Gln Gln Val Trp Val Asp Ser Arg Ala Leu Ser Thr
    1805                1810                1815

Thr Ile Met Gln Ala Met Asn Asp Asn Met Tyr Val Asn Ser Ser
    1820                1825                1830

Gln Arg Thr Asp Gly Leu Trp Leu Asn Ala Pro Tyr Thr Met Ser
    1835                1840                1845

Gly Ala Lys Trp Ala Gly Asp Thr Arg Ser Ala Asn Gly Arg Tyr
    1850                1855                1860

Val His Ile Ser Lys Ala Tyr Ser Asn Glu Val Gly Asn Thr Tyr
    1865                1870                1875

Tyr Leu Thr Asn Leu Asn Gly Gln Ser Thr Trp Ile Asp Lys Arg
    1880                1885                1890

Ala Phe Thr Val Thr Phe Asp Gln Val Val Ala Leu Asn Ala Thr
    1895                1900                1905

Ile Val Ala Arg Gln Arg Pro Asp Gly Met Phe Lys Thr Ala Pro
    1910                1915                1920

Tyr Gly Glu Ala Gly Ala Gln Phe Val Asp Tyr Val Thr Asn Tyr
    1925                1930                1935

Asn Gln Gln Thr Val Pro Val Thr Lys Gln His Ser Asp Ala Gln
    1940                1945                1950

Gly Asn Gln Trp Tyr Leu Ala Thr Val Asn Gly Thr Gln Tyr Trp
    1955                1960                1965

Ile Asp Gln Arg Ser Phe Ser Pro Val Val Thr Lys Val Val Asp
    1970                1975                1980

Tyr Gln Ala Lys Ile Val Pro Arg Thr Thr Arg Asp Gly Val Phe
    1985                1990                1995

Ser Gly Ala Pro Tyr Gly Glu Val Asn Ala Lys Leu Val Asn Met
    2000                2005                2010

Ala Thr Ala Tyr Gln Asn Gln Val Val His Ala Thr Gly Glu Tyr
    2015                2020                2025

Thr Asn Ala Ser Gly Ile Thr Trp Ser Gln Phe Ala Leu Ser Gly
    2030                2035                2040

Gln Glu Asp Lys Leu Trp Ile Asp Lys Arg Ala Leu Gln Ala
    2045                2050                2055

<210> SEQ ID NO 3
<211> LENGTH: 2018
<212> TYPE: PRT
<213> ORGANISM: Leuconostoc citreum

<400> SEQUENCE: 3

Asp Thr Asn Ser Asn Val Ala Val Lys Gln Ile Asn Asn Thr Gly Thr

-continued

```
1               5                   10                  15
Asn Asp Ser Gly Glu Lys Lys Val Pro Val Pro Ser Thr Asn Asn Asp
                20                  25                  30

Ser Leu Lys Gln Gly Thr Asp Gly Phe Trp Tyr Asp Ser Asp Gly Asn
                35                  40                  45

Arg Val Asp Gln Lys Thr Asn Gln Ile Leu Leu Thr Ala Glu Gln Leu
    50                  55                  60

Lys Lys Asn Asn Glu Lys Asn Leu Ser Val Ile Ser Asp Asp Thr Ser
65                  70                  75                  80

Lys Lys Asp Asp Glu Asn Ile Ser Lys Gln Thr Lys Ile Ala Asn Gln
                85                  90                  95

Gln Thr Val Asp Thr Ala Lys Gly Leu Thr Thr Ser Asn Leu Ser Asp
                100                 105                 110

Pro Ile Thr Gly Gly His Tyr Glu Asn His Asn Gly Tyr Phe Val Tyr
                115                 120                 125

Ile Asp Ala Ser Gly Lys Gln Val Thr Gly Leu Gln Asn Ile Asp Gly
            130                 135                 140

Asn Leu Gln Tyr Phe Asp Asp Asn Gly Tyr Gln Val Lys Gly Ser Phe
145                 150                 155                 160

Arg Asp Val Asn Gly Lys His Ile Tyr Phe Asp Ser Val Thr Gly Lys
                165                 170                 175

Ala Ser Ser Asn Val Asp Ile Val Asn Gly Lys Ala Gln Gly Tyr Asp
            180                 185                 190

Ala Gln Gly Asn Gln Leu Lys Lys Ser Tyr Val Ala Asp Ser Ser Gly
        195                 200                 205

Gln Thr Tyr Tyr Phe Asp Gly Asn Gly Gln Pro Leu Ile Gly Leu Gln
    210                 215                 220

Thr Ile Asp Gly Asn Leu Gln Tyr Phe Asn Gln Gln Gly Val Gln Ile
225                 230                 235                 240

Lys Gly Gly Phe Gln Asp Val Asn Asn Lys Arg Ile Tyr Phe Ala Pro
                245                 250                 255

Asn Thr Gly Asn Ala Val Ala Asn Thr Glu Ile Ile Asn Gly Lys Leu
            260                 265                 270

Gln Gly Arg Asp Ala Asn Gly Asn Gln Val Lys Asn Ala Phe Ser Lys
        275                 280                 285

Asp Val Ala Gly Asn Thr Phe Tyr Phe Asp Ala Asn Gly Val Met Leu
    290                 295                 300

Thr Gly Leu Gln Thr Ile Ser Gly Lys Thr Tyr Tyr Leu Asp Glu Gln
305                 310                 315                 320

Gly His Leu Arg Lys Asn Tyr Ala Gly Thr Phe Asn Asn Gln Phe Met
                325                 330                 335

Tyr Phe Asp Ala Asp Thr Gly Ala Gly Lys Thr Ala Ile Glu Tyr Gln
            340                 345                 350

Phe Asp Gln Gly Leu Val Ser Gln Ser Asn Glu Asn Thr Pro His Asn
        355                 360                 365

Ala Ala Lys Ser Tyr Asp Lys Ser Ser Phe Glu Asn Val Asp Gly Tyr
    370                 375                 380

Leu Thr Ala Asp Thr Trp Tyr Arg Pro Thr Asp Ile Leu Lys Asn Gly
385                 390                 395                 400

Asp Thr Trp Thr Ala Ser Thr Glu Thr Asp Met Arg Pro Leu Leu Met
                405                 410                 415

Thr Trp Trp Pro Asp Lys Gln Thr Gln Ala Asn Tyr Leu Asn Phe Met
                420                 425                 430
```

-continued

```
Ser Ser Lys Gly Leu Gly Ile Thr Thr Thr Tyr Thr Ala Ala Thr Ser
        435                 440                 445

Gln Lys Thr Leu Asn Asp Ala Ala Phe Val Ile Gln Thr Ala Ile Glu
    450                 455                 460

Gln Gln Ile Ser Leu Lys Lys Ser Thr Glu Trp Leu Arg Asp Ala Ile
465                 470                 475                 480

Asp Ser Phe Val Lys Thr Gln Ala Asn Trp Asn Lys Gln Thr Glu Asp
                485                 490                 495

Glu Ala Phe Asp Gly Leu Gln Trp Leu Gln Gly Phe Leu Ala Tyr
            500                 505                 510

Gln Asp Asp Ser His Arg Thr Pro Asn Thr Asp Ser Gly Asn Asn Arg
            515                 520                 525

Lys Leu Gly Arg Gln Pro Ile Asn Ile Asp Gly Ser Lys Asp Thr Thr
    530                 535                 540

Asp Gly Lys Gly Ser Glu Phe Leu Leu Ala Asn Asp Ile Asp Asn Ser
545                 550                 555                 560

Asn Pro Ile Val Gln Ala Glu Gln Leu Asn Trp Leu His Tyr Leu Met
                565                 570                 575

Asn Phe Gly Ser Ile Thr Gly Asn Asn Asp Asn Ala Asn Phe Asp Gly
            580                 585                 590

Ile Arg Val Asp Ala Val Asp Asn Val Asp Ala Asp Leu Leu Lys Ile
        595                 600                 605

Ala Gly Asp Tyr Phe Lys Ala Leu Tyr Gly Thr Asp Lys Ser Asp Ala
    610                 615                 620

Asn Ala Asn Lys His Leu Ser Ile Leu Glu Asp Trp Asn Gly Lys Asp
625                 630                 635                 640

Pro Gln Tyr Val Asn Gln Gln Gly Asn Ala Gln Leu Thr Met Asp Tyr
                645                 650                 655

Thr Val Thr Ser Gln Phe Gly Asn Ser Leu Thr His Gly Ala Asn Asn
            660                 665                 670

Arg Ser Asn Met Trp Tyr Phe Leu Asp Thr Gly Tyr Tyr Leu Asn Gly
        675                 680                 685

Asp Leu Asn Lys Lys Ile Val Asp Lys Asn Arg Pro Asn Ser Gly Thr
    690                 695                 700

Leu Val Asn Arg Ile Ala Asn Ser Gly Asp Thr Lys Val Ile Pro Asn
705                 710                 715                 720

Tyr Ser Phe Val Arg Ala His Asp Tyr Asp Ala Gln Asp Pro Ile Arg
                725                 730                 735

Lys Ala Met Ile Asp His Gly Ile Ile Lys Asn Met Gln Asp Thr Phe
            740                 745                 750

Thr Phe Asp Gln Leu Ala Gln Gly Met Glu Phe Tyr Tyr Lys Asp Gln
        755                 760                 765

Glu Asn Pro Ser Gly Phe Lys Lys Tyr Asn Asp Tyr Asn Leu Pro Ser
    770                 775                 780

Ala Tyr Ala Met Leu Leu Thr Asn Lys Asp Thr Val Pro Arg Val Tyr
785                 790                 795                 800

Tyr Gly Asp Met Tyr Leu Glu Gly Gly Gln Tyr Met Glu Lys Gly Thr
                805                 810                 815

Ile Tyr Asn Pro Val Ile Ser Ala Leu Leu Lys Ala Arg Ile Lys Tyr
            820                 825                 830

Val Ser Gly Gly Gln Thr Met Ala Thr Asp Ser Gly Lys Asp Leu
        835                 840                 845
```

```
Lys Asp Gly Glu Thr Asp Leu Leu Thr Ser Val Arg Phe Gly Lys Gly
850                 855                 860

Ile Met Thr Ser Asp Gln Thr Thr Thr Gln Asp Asn Ser Gln Asp Tyr
865                 870                 875                 880

Lys Asn Arg Gly Ile Gly Val Ile Val Gly Asn Asn Pro Asp Leu Lys
                885                 890                 895

Leu Asn Asn Asp Lys Thr Ile Thr Leu His Met Gly Lys Ala His Lys
            900                 905                 910

Asn Gln Leu Tyr Arg Ala Leu Val Leu Ser Asn Asp Ser Gly Ile Asp
        915                 920                 925

Val Tyr Asp Ser Asp Asp Lys Ala Pro Thr Leu Arg Thr Asn Asp Asn
930                 935                 940

Gly Asp Leu Ile Phe His Lys Thr Asn Thr Phe Val Lys Gln Asp Gly
945                 950                 955                 960

Thr Ile Ile Asn Tyr Glu Met Lys Gly Ser Leu Asn Ala Leu Ile Ser
                965                 970                 975

Gly Tyr Leu Gly Val Trp Val Pro Val Gly Ala Ser Asp Ser Gln Asp
            980                 985                 990

Ala Arg Thr Val Ala Thr Glu Ser  Ser  Ser  Ser Asn Asp  Gly Ser Val
        995                 1000                1005

Phe His  Ser Asn Ala Ala Leu  Asp Ser Asn Val Ile  Tyr Glu Gly
1010                 1015                1020

Phe Ser  Asn Phe Gln Ala Met  Pro Thr Ser Pro Glu  Gln Ser Thr
1025                 1030                1035

Asn Val  Val Ile Ala Thr Lys  Ala Asn Leu Phe Lys  Glu Leu Gly
1040                 1045                1050

Ile Thr  Ser Phe Glu Leu Ala  Pro Gln Tyr Arg Ser  Ser Gly Asp
1055                 1060                1065

Thr Asn  Tyr Gly Gly Met Ser  Phe Leu Asp Ser Phe  Leu Asn Asn
1070                 1075                1080

Gly Tyr  Ala Phe Thr Asp Arg  Tyr Asp Leu Gly Phe  Asn Lys Ala
1085                 1090                1095

Asp Gly  Asn Pro Asn Pro Thr  Lys Tyr Gly Thr Asp  Gln Asp Leu
1100                 1105                1110

Arg Asn  Ala Ile Glu Ala Leu  His Lys Asn Gly Met  Gln Ala Ile
1115                 1120                1125

Ala Asp  Trp Val Pro Asp Gln  Ile Tyr Ala Leu Pro  Gly Lys Glu
1130                 1135                1140

Val Val  Thr Ala Thr Arg Val  Asp Glu Arg Gly Asn  Gln Leu Lys
1145                 1150                1155

Asp Thr  Asp Phe Val Asn Leu  Leu Tyr Val Ala Asn  Thr Lys Ser
1160                 1165                1170

Ser Gly  Val Asp Tyr Gln Ala  Lys Tyr Gly Gly Glu  Phe Leu Asp
1175                 1180                1185

Lys Leu  Arg Glu Glu Tyr Pro  Ser Leu Phe Lys Gln  Asn Gln Val
1190                 1195                1200

Ser Thr  Gly Gln Pro Ile Asp  Ala Ser Thr Lys Ile  Lys Gln Trp
1205                 1210                1215

Ser Ala  Lys Tyr Met Asn Gly  Thr Asn Ile Leu His  Arg Gly Ala
1220                 1225                1230

Tyr Tyr  Val Leu Lys Asp Trp  Ala Thr Asn Gln Tyr  Phe Asn Ile
1235                 1240                1245

Ala Lys  Thr Asn Glu Val Phe  Leu Pro Leu Gln Leu  Gln Asn Lys
```

-continued

```
             1250              1255              1260
Asp Ala Gln Thr Gly Phe Ile Ser Asp Ala Ser Gly Val Lys Tyr
             1265              1270              1275
Tyr Ser Ile Ser Gly Tyr Gln Ala Lys Asp Thr Phe Ile Glu Asp
             1280              1285              1290
Gly Asn Gly Asn Trp Tyr Tyr Phe Asp Lys Asp Gly Tyr Met Val
             1295              1300              1305
Arg Ser Gln Gln Gly Glu Asn Pro Ile Arg Thr Val Glu Thr Ser
             1310              1315              1320
Val Asn Thr Arg Asn Gly Asn Tyr Tyr Phe Met Pro Asn Gly Val
             1325              1330              1335
Glu Leu Arg Lys Gly Phe Gly Thr Asp Asn Ser Gly Asn Val Tyr
             1340              1345              1350
Tyr Phe Asp Asp Gln Gly Lys Met Val Arg Asp Lys Tyr Ile Asn
             1355              1360              1365
Asp Asp Ala Asn Asn Phe Tyr His Leu Asn Val Asp Gly Thr Met
             1370              1375              1380
Ser Arg Gly Leu Phe Lys Phe Asp Ser Asp Thr Leu Gln Tyr Phe
             1385              1390              1395
Ala Ser Asn Gly Val Gln Ile Lys Asp Ser Tyr Ala Lys Asp Ser
             1400              1405              1410
Lys Gly Asn Lys Tyr Tyr Phe Asp Ser Ala Thr Gly Asn Asn Asp
             1415              1420              1425
Thr Gly Lys Ala Gln Thr Trp Asp Gly Asn Gly Tyr Tyr Ile Thr
             1430              1435              1440
Ile Asp Ser Asp Ala Asn Asn Thr Ile Gly Val Asn Thr Asp Tyr
             1445              1450              1455
Thr Ala Tyr Ile Thr Ser Ser Leu Arg Glu Asp Gly Leu Phe Ala
             1460              1465              1470
Asn Ala Pro Tyr Gly Val Val Thr Lys Asp Gln Asn Gly Asn Asp
             1475              1480              1485
Leu Lys Trp Gln Tyr Ile Asn His Thr Lys Gln Tyr Glu Gly Gln
             1490              1495              1500
Gln Val Gln Val Thr Arg Gln Tyr Thr Asp Ser Lys Gly Val Ser
             1505              1510              1515
Trp Asn Leu Ile Thr Phe Ala Gly Gly Asp Leu Gln Gly Gln Arg
             1520              1525              1530
Leu Trp Val Asp Ser Arg Ala Leu Thr Met Thr Pro Phe Lys Thr
             1535              1540              1545
Met Asn Gln Ile Ser Phe Ile Ser Tyr Ala Asn Arg Asn Asp Gly
             1550              1555              1560
Leu Phe Leu Asn Ala Pro Tyr Gln Val Lys Gly Tyr Gln Leu Ala
             1565              1570              1575
Gly Met Ser Asn Gln Tyr Lys Gly Gln Gln Val Thr Ile Ala Gly
             1580              1585              1590
Val Ala Asn Val Ser Gly Lys Asp Trp Ser Leu Ile Ser Phe Asn
             1595              1600              1605
Gly Thr Gln Tyr Trp Ile Asp Ser Gln Ala Leu Asn Thr Asn Phe
             1610              1615              1620
Thr His Asp Met Asn Gln Lys Val Phe Val Asn Thr Thr Ser Asn
             1625              1630              1635
Leu Asp Gly Leu Phe Leu Asn Ala Pro Tyr Arg Gln Pro Gly Tyr
             1640              1645              1650
```

```
Lys Leu Ala Gly Leu Ala Lys Asn Tyr Asn Asn Gln Thr Val Thr
1655                1660                1665

Val Ser Gln Gln Tyr Phe Asp Asp Gly Thr Val Trp Ser Gln
1670                1675                1680

Val Val Leu Gly Gly Gln Thr Val Trp Val Asp Asn His Ala Leu
1685                1690                1695

Ala Gln Met Gln Val Ser Asp Thr Asp Gln Gln Leu Tyr Val Asn
1700                1705                1710

Ser Asn Gly Arg Asn Asp Gly Leu Phe Leu Asn Ala Pro Tyr Arg
1715                1720                1725

Gly Gln Gly Ser Gln Leu Ile Gly Met Thr Ala Asp Tyr Asn Gly
1730                1735                1740

Gln His Val Gln Val Thr Lys Gln Gly Gln Asp Ala Tyr Gly Ala
1745                1750                1755

Gln Trp Arg Leu Ile Thr Leu Asn Asn Gln Gln Val Trp Val Asp
1760                1765                1770

Ser Arg Ala Leu Ser Thr Thr Ile Met Gln Ala Met Asn Asp Asn
1775                1780                1785

Met Tyr Val Asn Ser Ser Gln Arg Thr Asp Gly Leu Trp Leu Asn
1790                1795                1800

Ala Pro Tyr Thr Met Ser Gly Ala Lys Trp Ala Gly Asp Thr Arg
1805                1810                1815

Ser Ala Asn Gly Arg Tyr Val His Ile Ser Lys Ala Tyr Ser Asn
1820                1825                1830

Glu Val Gly Asn Thr Tyr Tyr Leu Thr Asn Leu Asn Gly Gln Ser
1835                1840                1845

Thr Trp Ile Asp Lys Arg Ala Phe Thr Val Thr Phe Asp Gln Val
1850                1855                1860

Val Ala Leu Asn Ala Thr Ile Val Ala Arg Gln Arg Pro Asp Gly
1865                1870                1875

Met Phe Lys Thr Ala Pro Tyr Gly Glu Ala Gly Ala Gln Phe Val
1880                1885                1890

Asp Tyr Val Thr Asn Tyr Asn Gln Gln Thr Val Pro Val Thr Lys
1895                1900                1905

Gln His Ser Asp Ala Gln Gly Asn Gln Trp Tyr Leu Ala Thr Val
1910                1915                1920

Asn Gly Thr Gln Tyr Trp Ile Asp Gln Arg Ser Phe Ser Pro Val
1925                1930                1935

Val Thr Lys Val Val Asp Tyr Gln Ala Lys Ile Val Pro Arg Thr
1940                1945                1950

Thr Arg Asp Gly Val Phe Ser Gly Ala Pro Tyr Gly Glu Val Asn
1955                1960                1965

Ala Lys Leu Val Asn Met Ala Thr Ala Tyr Gln Asn Gln Val Val
1970                1975                1980

His Ala Thr Gly Glu Tyr Thr Asn Ala Ser Gly Ile Thr Trp Ser
1985                1990                1995

Gln Phe Ala Leu Ser Gly Gln Glu Asp Lys Leu Trp Ile Asp Lys
2000                2005                2010

Arg Ala Leu Gln Ala
2015
```

<210> SEQ ID NO 4
<211> LENGTH: 4545

<212> TYPE: DNA
<213> ORGANISM: Leuconostoc mesenteroides

<400> SEQUENCE: 4

```
atgagaaata gaaatgcaac aagcgttttc cggaaaaaga tgtataaatc tgggaaaatg        60
ttagtcattg cagggagtgt ttcaataatt ggtgttacca gttttattca acaagcacaa       120
gctgatgttt cacaaaacaa tggggtagta gtggccacgg cagtcgatca atcgaatttg       180
gatgcgacta cgtctgacaa atcaatcaca acagatgata aagctgcaac aacagcagct       240
acatcaacag atgataaggc tacaacaaca gtagctacat caacagatga taaggataca       300
acaacagcag ctacatcaac agatgataag gctacaacaa cagtagctac atcaacagat       360
gataaggcta caacaacagc agctacatca acagatgata aagctgcaac aacagcagct       420
acatcaacgg atgataaagc tgcaacaaca gcagctacat caacggatga taaagctgca       480
acaacagcag atacatcaac agatgataaa gctgcaacaa cagcagctac atcaacagat       540
gataaggcta caacaacagc agctacatca acagatgata aacagcaac aacagtcggc        600
acatctgata ataacaattc agctacagcg agcgataaag atgtaagttc atcggcacaa       660
aaaagtcaaa cgattgataa caattcgaag acggccgata ctactgcagc attagaagct       720
agttcaaaga tctgaaaac gattgatggc aaaacatatt attacgacga tgatgatcaa       780
gtaaaaaaga actttgctac cgtaattgat ggtaaggtac tttattttga taagagact       840
ggcgcattag ctgatacaaa tgactatcaa tttttagaag gattgactag tgaaaataat       900
acttatacgg agcataatgc ctcagttggt acatcttctg atagttatac aaacgttgac       960
gggtacctaa cagccgacag ttggtacagg cctaaggaca tattagtcaa cggtcaaaac      1020
tgggaatcat caaaggatga cgatttacga ccattgttaa tgacttggtg gccagataag      1080
gcaacacaag taaactattt gaatgcgatg aagtatttag atgccactga acggaaact       1140
gtttatactt cagatgacag tcaagacgct ttgaacaaag cagcacagaa cattcaagtg      1200
aaaattgaag aaaaaattag tcaagaaggc caaacacaat ggctaaagga tgatatttca      1260
aaatttgttg atagccaatc aaattggaat attgctagtg aatcaaaagg aactgatcat      1320
ttgcaaggtg gtgcattgtt gtatgtcaat agtgataaaa caccagatgc caattctgat      1380
tatcgattac ttaatcgcac accaacaaat caaacaggca cgcctttgta tacgacagat      1440
ccaactcaag gtggttatga cttcctcttg gccaatgatg tggataattc aaacccagtt      1500
gttcaagcag aacaactaaa ttggatgtat tacttgttaa actttggatc aattactaat      1560
aacgatgcag atgctaactt tgatagtatt cgagtagatg ctgttgataa cgttgatgcc      1620
gacttattgc aaattgcagc tgattatttc aaggcagcat atggcgtcga taagagtgat      1680
gcaatttcga atcaacatgt ttccattctt gaagattgga gtgacaatga tgctgaatat      1740
gtgaaagaca atggcgacaa tcaattgtca atggataata aattgcgttt gtcattaaaa      1800
tactcactca ctatgccagc agtcgatcaa tatggtaata aagaagtgg attagaacct      1860
ttttttgacaa atagtttagt tgatcgtaca atgattcga cagataatac cgcacaacca      1920
aattattctt tgttcgtgc acatgatagt gaagtacaaa cagttattgc tgaaattatt      1980
aaacaaagaa ttgatccgga ttctgatggc ttatcaccaa cgatggacca attaacagaa      2040
gcgtttaaaa tttataatgc tgatcagttg aaaacggata agaattcac acaatataac      2100
attccaagta cttatgccac aatactaacg aataaagata cagtgccacg tgtgtactat      2160
ggtgatatgt atacagatga tggtcaatac atggcaacaa agtcacttta ttacgatgca      2220
```

```
attgatactt tgctgaagtc tcgtatcaag tatgtttctg gcgggcaaac aatgtctatg    2280
aaatatatgc aaggtgatag tagtatggct gctgacagtt atagaggcat tttgacatca    2340
gttcgttatg gtaatggtgc catgactgct accgatgcag ggacaaatga aacacgtacg    2400
caaggtattg cagtaattga aagtaataac ccagatttga agttgagcag tacagatcaa    2460
gtagttgtag atatgggcat agcgcacaaa aaccaggctt atcgtcctgc tttgttaaca    2520
actaaagatg gcatagatac ttatgtatct gatagtgatg tctcacaaag cttaataaga    2580
tatacaaata gtaatgggca acttattttc aatagttcag atattgttgg tacagcaaat    2640
ccacaagttt ctggatactt ggctgtctgg gtacccgttg gtgcttcaga tactcaagat    2700
gcgcgaactg aaagtagtac agcaacaact gctgatggac aaacattaca ttcaaatgcc    2760
gcacttgatt ctcaagttat ttatgaaagt ttctctaact tccaatctac accaacaaca    2820
gaagctgaat atgctaatgt gcaaattgca aacaatactg atttatacaa gagttgggga    2880
attacgaact tcgagtttcc accacaatat cgttcaagta cggatagtag tttcttagat    2940
tcaattattc aaaatggtta tgcatttact gatcgttatg atcttggatt caatacacca    3000
acgaagtatg gtactgtaga tcaactccgt acagctatta agctttgca tgcgacaggt    3060 atcaaggcaa tggcagattg gtaccagac cagatttata atttgacagg taagaagtg     3120 gttgcggtac aacgtgtcaa caactcagga atctataatc aagattctgt aattaataaa    3180
acattatatg cttcacaaac cgttggtggc ggagaatatc aggcactata tggtggagag    3240
ttccttgatg aaatcaagaa attgtaccct tctctattcg aaaaaaatca aatttcaacc    3300
ggcgtaccaa tggatgctag tgaaaagata aagaatggt ccgctaagta ctttaacggt     3360
actaacattc aaggtcgtgg tgcttactat gtccttaagg actgggctac aaatgagtac    3420
ttcaaggtaa gcacttcaag caacagcagt gtatttttgc caaagcagtt gacgaatgaa    3480
gaatcaaaca ctggatttat ttcaactgat ggtgggatga catattattc tacaagtgga    3540
taccaggcaa aagatacatt catccaagat gacaaatcta attggtatta ctttgacaag    3600
aatggttata tgacatatgg tttccagaca gtcaatgata taattatta cttcttgcct     3660 aatggtattg aattacaaga tgctatctta gaagatagta aggaaatgt ttattatttc     3720 aatcaatatg gcaaacaagc tgttgatgga tactacatgt tggctaataa aacttggcgt    3780
tactttgaca aaaatggtgt tatggctaat gctggcttaa caaccgtgac tgttgatggg    3840
caggagcata tccaatactt tgataagaac ggtattcagg tcaaagggac ttccgtgaaa    3900
gatgcagacg gaaagctacg ctactttgac actgattctg gtgatatggt gacgaaccgc    3960
tttggtgaaa acacagatgg tacatggtca tactttggtg ctgacggtat cgctgtaact    4020
ggtgcacaga caattagtgg gcaaaaattg ttctttgatg ccgacggaca acagattaaa    4080
ggtaaggaag cgactgataa aaaaggcaaa gtgcattatt atgatgctaa ttctggtgaa    4140
atgatcacta tcgtttttga aaagttatca gatggatcat gggcgtactt taataaaaaa    4200
ggtaacatcg taaccggcgc acaagtcatt aatggtcaac atttgttctt tgaaagcaac    4260
ggtaaccaag ttaagggtcg tgaatacacg gctactgatg ggaagatgcg ctactatgat    4320
gcagattctg gtgatatggt gacgaatcgc tttgaacgaa tatcagacgg atcatgggca    4380
tattttggtg ctaatggtgt tgctgtaact ggggaacaaa atataaatgg acaacaactg    4440
tattttgatg ccaatggtca tcaagttaag ggagccgcag taacacaagc tgacggtagc    4500
caaaaatatt atgacgcaaa ttctggagag atgattaaaa gctaa                    4545
```

```
<210> SEQ ID NO 5
<211> LENGTH: 1514
<212> TYPE: PRT
<213> ORGANISM: Leuconostoc mesenteroides

<400> SEQUENCE: 5

Met Arg Asn Arg Asn Ala Thr Ser Val Phe Arg Lys Lys Met Tyr Lys
1               5                   10                  15

Ser Gly Lys Met Leu Val Ile Ala Gly Ser Val Ser Ile Ile Gly Val
            20                  25                  30

Thr Ser Phe Ile Gln Gln Ala Gln Ala Asp Val Ser Gln Asn Asn Gly
        35                  40                  45

Val Val Val Ala Thr Ala Val Asp Gln Ser Asn Leu Asp Ala Thr Thr
    50                  55                  60

Ser Asp Lys Ser Ile Thr Thr Asp Lys Ala Ala Thr Thr Ala Ala
65                  70                  75                  80

Thr Ser Thr Asp Asp Lys Ala Thr Thr Val Ala Thr Ser Thr Asp
                85                  90                  95

Asp Lys Asp Thr Thr Ala Ala Thr Ser Thr Asp Asp Lys Ala Thr
                100                 105                 110

Thr Thr Val Ala Thr Ser Thr Asp Asp Lys Ala Thr Thr Ala Ala
            115                 120                 125

Thr Ser Thr Asp Asp Lys Ala Ala Thr Ala Ala Thr Ser Thr Asp
        130                 135                 140

Asp Lys Ala Thr Thr Ala Ala Thr Ser Thr Asp Asp Lys Ala Ala
145                 150                 155                 160

Thr Thr Ala Asp Thr Ser Thr Asp Lys Ala Ala Thr Thr Ala Ala
                165                 170                 175

Thr Ser Thr Asp Asp Lys Ala Thr Thr Ala Ala Thr Ser Thr Asp
            180                 185                 190

Asp Lys Thr Ala Thr Thr Val Gly Thr Ser Asp Asn Asn Ser Ala
        195                 200                 205

Thr Ala Ser Asp Lys Asp Val Ser Ser Ala Gln Lys Ser Gln Thr
210                 215                 220

Ile Asp Asn Asn Ser Lys Thr Ala Asp Thr Thr Ala Ala Leu Glu Ala
225                 230                 235                 240

Ser Ser Lys Asn Leu Lys Thr Ile Asp Gly Lys Thr Tyr Tyr Asp
                245                 250                 255

Asp Asp Asp Gln Val Lys Lys Asn Phe Ala Thr Val Ile Asp Gly Lys
            260                 265                 270

Val Leu Tyr Phe Asp Lys Glu Thr Gly Ala Leu Ala Asp Thr Asn Asp
        275                 280                 285

Tyr Gln Phe Leu Glu Gly Leu Thr Ser Glu Asn Asn Thr Tyr Thr Glu
    290                 295                 300

His Asn Ala Ser Val Gly Thr Ser Ser Asp Ser Tyr Thr Asn Val Asp
305                 310                 315                 320

Gly Tyr Leu Thr Ala Asp Ser Trp Tyr Arg Pro Lys Asp Ile Leu Val
                325                 330                 335

Asn Gly Gln Asn Trp Glu Ser Ser Lys Asp Asp Leu Arg Pro Leu
            340                 345                 350

Leu Met Thr Trp Trp Pro Asp Lys Ala Thr Gln Val Asn Tyr Leu Asn
        355                 360                 365

Ala Met Lys Tyr Leu Asp Ala Thr Glu Thr Glu Thr Val Tyr Thr Ser
    370                 375                 380
```

-continued

Asp Asp Ser Gln Asp Ala Leu Asn Lys Ala Ala Gln Asn Ile Gln Val
385                 390                 395                 400

Lys Ile Glu Glu Lys Ile Ser Gln Glu Gly Gln Thr Gln Trp Leu Lys
            405                 410                 415

Asp Asp Ile Ser Lys Phe Val Asp Ser Gln Ser Asn Trp Asn Ile Ala
            420                 425                 430

Ser Glu Ser Lys Gly Thr Asp His Leu Gln Gly Gly Ala Leu Leu Tyr
            435                 440                 445

Val Asn Ser Asp Lys Thr Pro Asp Ala Asn Ser Asp Tyr Arg Leu Leu
450                 455                 460

Asn Arg Thr Pro Thr Asn Gln Thr Gly Thr Pro Leu Tyr Thr Thr Asp
465                 470                 475                 480

Pro Thr Gln Gly Gly Tyr Asp Phe Leu Leu Ala Asn Asp Val Asp Asn
            485                 490                 495

Ser Asn Pro Val Val Gln Ala Glu Gln Leu Asn Trp Met Tyr Tyr Leu
            500                 505                 510

Leu Asn Phe Gly Ser Ile Thr Asn Asn Asp Ala Asp Ala Asn Phe Asp
            515                 520                 525

Ser Ile Arg Val Asp Ala Val Asp Asn Val Asp Ala Asp Leu Leu Gln
530                 535                 540

Ile Ala Ala Asp Tyr Phe Lys Ala Ala Tyr Gly Val Asp Lys Ser Asp
545                 550                 555                 560

Ala Ile Ser Asn Gln His Val Ser Ile Leu Glu Asp Trp Ser Asp Asn
            565                 570                 575

Asp Ala Glu Tyr Val Lys Asp Asn Gly Asp Asn Gln Leu Ser Met Asp
            580                 585                 590

Asn Lys Leu Arg Leu Ser Leu Lys Tyr Ser Leu Thr Met Pro Ala Val
            595                 600                 605

Asp Gln Tyr Gly Asn Lys Arg Ser Gly Leu Glu Pro Phe Leu Thr Asn
            610                 615                 620

Ser Leu Val Asp Arg Thr Asn Asp Ser Thr Asp Asn Thr Ala Gln Pro
625                 630                 635                 640

Asn Tyr Ser Phe Val Arg Ala His Asp Ser Glu Val Gln Thr Val Ile
            645                 650                 655

Ala Glu Ile Ile Lys Gln Arg Ile Asp Pro Asp Ser Asp Gly Leu Ser
            660                 665                 670

Pro Thr Met Asp Gln Leu Thr Glu Ala Phe Lys Ile Tyr Asn Ala Asp
            675                 680                 685

Gln Leu Lys Thr Asp Lys Glu Phe Thr Gln Tyr Asn Ile Pro Ser Thr
690                 695                 700

Tyr Ala Thr Ile Leu Thr Asn Lys Asp Thr Val Pro Arg Val Tyr Tyr
705                 710                 715                 720

Gly Asp Met Tyr Thr Asp Asp Gly Gln Tyr Met Ala Thr Lys Ser Leu
            725                 730                 735

Tyr Tyr Asp Ala Ile Asp Thr Leu Leu Lys Ser Arg Ile Lys Tyr Val
            740                 745                 750

Ser Gly Gly Gln Thr Met Ser Met Lys Tyr Met Gln Gly Asp Ser Ser
            755                 760                 765

Met Ala Ala Asp Ser Tyr Arg Gly Ile Leu Thr Ser Val Arg Tyr Gly
            770                 775                 780

Asn Gly Ala Met Thr Ala Thr Asp Ala Gly Thr Asn Glu Thr Arg Thr
785                 790                 795                 800

Gln Gly Ile Ala Val Ile Glu Ser Asn Asn Pro Asp Leu Lys Leu Ser

-continued

Ser Thr Asp Gln Val Val Asp Met Gly Ile Ala His Lys Asn Gln
805                 810                 815
                820                 825                 830

Ala Tyr Arg Pro Ala Leu Leu Thr Thr Lys Asp Gly Ile Asp Thr Tyr
            835                 840                 845

Val Ser Asp Ser Asp Val Ser Gln Ser Leu Ile Arg Tyr Thr Asn Ser
850                 855                 860

Asn Gly Gln Leu Ile Phe Asn Ser Ser Asp Ile Val Gly Thr Ala Asn
865                 870                 875                 880

Pro Gln Val Ser Gly Tyr Leu Ala Val Trp Val Pro Val Gly Ala Ser
                885                 890                 895

Asp Thr Gln Asp Ala Arg Thr Glu Ser Ser Thr Ala Thr Thr Ala Asp
                900                 905                 910

Gly Gln Thr Leu His Ser Asn Ala Ala Leu Asp Ser Gln Val Ile Tyr
                915                 920                 925

Glu Ser Phe Ser Asn Phe Gln Ser Thr Pro Thr Thr Glu Ala Glu Tyr
        930                 935                 940

Ala Asn Val Gln Ile Ala Asn Asn Thr Asp Leu Tyr Lys Ser Trp Gly
945                 950                 955                 960

Ile Thr Asn Phe Glu Phe Pro Pro Gln Tyr Arg Ser Ser Thr Asp Ser
                965                 970                 975

Ser Phe Leu Asp Ser Ile Ile Gln Asn Gly Tyr Ala Phe Thr Asp Arg
            980                 985                 990

Tyr Asp Leu Gly Phe Asn Thr Pro  Thr Lys Tyr Gly Thr Val Asp Gln
                995                 1000                1005

Leu Arg  Thr Ala Ile Lys Ala  Leu His Ala Thr Gly  Ile Lys Ala
1010                1015                1020

Met Ala  Asp Trp Val Pro Asp  Gln Ile Tyr Asn Leu  Thr Gly Lys
1025                1030                1035

Glu Val  Val Ala Val Gln Arg  Val Asn Asn Ser Gly  Ile Tyr Asn
1040                1045                1050

Gln Asp  Ser Val Ile Asn Lys  Thr Leu Tyr Ala Ser  Gln Thr Val
1055                1060                1065

Gly Gly  Gly Glu Tyr Gln Ala  Leu Tyr Gly Gly Glu  Phe Leu Asp
1070                1075                1080

Glu Ile  Lys Lys Leu Tyr Pro  Ser Leu Phe Glu Lys  Asn Gln Ile
1085                1090                1095

Ser Thr  Gly Val Pro Met Asp  Ala Ser Glu Lys Ile  Lys Glu Trp
1100                1105                1110

Ser Ala  Lys Tyr Phe Asn Gly  Thr Asn Ile Gln Gly  Arg Gly Ala
1115                1120                1125

Tyr Tyr  Val Leu Lys Asp Trp  Ala Thr Asn Glu Tyr  Phe Lys Val
1130                1135                1140

Ser Thr  Ser Ser Asn Ser Ser  Val Phe Leu Pro Lys  Gln Leu Thr
1145                1150                1155

Asn Glu  Glu Ser Asn Thr Gly  Phe Ile Ser Thr Asp  Gly Gly Met
1160                1165                1170

Thr Tyr  Tyr Ser Thr Ser Gly  Tyr Gln Ala Lys Asp  Thr Phe Ile
1175                1180                1185

Gln Asp  Asp Lys Ser Asn Trp  Tyr Tyr Phe Asp Lys  Asn Gly Tyr
1190                1195                1200

Met Thr  Tyr Gly Phe Gln Thr  Val Asn Asp Asn Asn  Tyr Tyr Phe
1205                1210                1215

Leu Pro Asn Gly Ile Glu Leu Gln Asp Ala Ile Leu Glu Asp Ser
1220                 1225                 1230

Lys Gly Asn Val Tyr Tyr Phe Asn Gln Tyr Gly Lys Gln Ala Val
1235                 1240                 1245

Asp Gly Tyr Tyr Met Leu Ala Asn Lys Thr Trp Arg Tyr Phe Asp
1250                 1255                 1260

Lys Asn Gly Val Met Ala Asn Ala Gly Leu Thr Thr Val Thr Val
1265                 1270                 1275

Asp Gly Gln Glu His Ile Gln Tyr Phe Asp Lys Asn Gly Ile Gln
1280                 1285                 1290

Val Lys Gly Thr Ser Val Lys Asp Ala Asp Gly Lys Leu Arg Tyr
1295                 1300                 1305

Phe Asp Thr Asp Ser Gly Asp Met Val Thr Asn Arg Phe Gly Glu
1310                 1315                 1320

Asn Thr Asp Gly Thr Trp Ser Tyr Phe Gly Ala Asp Gly Ile Ala
1325                 1330                 1335

Val Thr Gly Ala Gln Thr Ile Ser Gly Gln Lys Leu Phe Phe Asp
1340                 1345                 1350

Ala Asp Gly Gln Gln Ile Lys Gly Lys Glu Ala Thr Asp Lys Lys
1355                 1360                 1365

Gly Lys Val His Tyr Tyr Asp Ala Asn Ser Gly Glu Met Ile Thr
1370                 1375                 1380

Asn Arg Phe Glu Lys Leu Ser Asp Gly Ser Trp Ala Tyr Phe Asn
1385                 1390                 1395

Lys Lys Gly Asn Ile Val Thr Gly Ala Gln Val Ile Asn Gly Gln
1400                 1405                 1410

His Leu Phe Phe Glu Ser Asn Gly Asn Gln Val Lys Gly Arg Glu
1415                 1420                 1425

Tyr Thr Ala Thr Asp Gly Lys Met Arg Tyr Tyr Asp Ala Asp Ser
1430                 1435                 1440

Gly Asp Met Val Thr Asn Arg Phe Glu Arg Ile Ser Asp Gly Ser
1445                 1450                 1455

Trp Ala Tyr Phe Gly Ala Asn Gly Val Ala Val Thr Gly Glu Gln
1460                 1465                 1470

Asn Ile Asn Gly Gln Gln Leu Tyr Phe Asp Ala Asn Gly His Gln
1475                 1480                 1485

Val Lys Gly Ala Ala Val Thr Gln Ala Asp Gly Ser Gln Lys Tyr
1490                 1495                 1500

Tyr Asp Ala Asn Ser Gly Glu Met Ile Lys Ser
1505                 1510

<210> SEQ ID NO 6
<211> LENGTH: 1473
<212> TYPE: PRT
<213> ORGANISM: Leuconostoc mesenteroides

<400> SEQUENCE: 6

Asp Val Ser Gln Asn Asn Gly Val Val Ala Thr Ala Val Asp Gln
1               5                   10                  15

Ser Asn Leu Asp Ala Thr Thr Ser Asp Lys Ser Ile Thr Thr Asp Asp
                20                  25                  30

Lys Ala Ala Thr Thr Ala Ala Thr Ser Thr Asp Asp Lys Ala Thr Thr
            35                  40                  45

Thr Val Ala Thr Ser Thr Asp Asp Lys Asp Thr Thr Thr Ala Ala Thr

```
            50                  55                  60
Ser Thr Asp Asp Lys Ala Thr Thr Val Ala Thr Ser Thr Asp Asp
65                  70                  75                  80

Lys Ala Thr Thr Thr Ala Ala Thr Ser Thr Asp Asp Lys Ala Ala Thr
                85                  90                  95

Thr Ala Ala Thr Ser Thr Asp Asp Lys Ala Ala Thr Thr Ala Ala Thr
                100                 105                 110

Ser Thr Asp Asp Lys Ala Ala Thr Ala Asp Thr Ser Thr Asp Asp
                115                 120                 125

Lys Ala Ala Thr Thr Ala Ala Thr Ser Thr Asp Asp Lys Ala Thr Thr
                130                 135                 140

Thr Ala Ala Thr Ser Thr Asp Asp Lys Thr Ala Thr Val Gly Thr
145                 150                 155                 160

Ser Asp Asn Asn Asn Ser Ala Thr Ala Ser Asp Lys Asp Val Ser Ser
                165                 170                 175

Ser Ala Gln Lys Ser Gln Thr Ile Asp Asn Asn Ser Lys Thr Ala Asp
                180                 185                 190

Thr Thr Ala Ala Leu Glu Ala Ser Ser Lys Asn Leu Lys Thr Ile Asp
                195                 200                 205

Gly Lys Thr Tyr Tyr Tyr Asp Asp Asp Gln Val Lys Lys Asn Phe
210                 215                 220

Ala Thr Val Ile Asp Gly Lys Val Leu Tyr Phe Asp Lys Glu Thr Gly
225                 230                 235                 240

Ala Leu Ala Asp Thr Asn Asp Tyr Gln Phe Leu Glu Gly Leu Thr Ser
                245                 250                 255

Glu Asn Asn Thr Tyr Thr Glu His Asn Ala Ser Val Gly Thr Ser Ser
                260                 265                 270

Asp Ser Tyr Thr Asn Val Asp Gly Tyr Leu Thr Ala Asp Ser Trp Tyr
                275                 280                 285

Arg Pro Lys Asp Ile Leu Val Asn Gly Gln Asn Trp Glu Ser Ser Lys
290                 295                 300

Asp Asp Asp Leu Arg Pro Leu Leu Met Thr Trp Trp Pro Asp Lys Ala
305                 310                 315                 320

Thr Gln Val Asn Tyr Leu Asn Ala Met Lys Tyr Leu Asp Ala Thr Glu
                325                 330                 335

Thr Glu Thr Val Tyr Thr Ser Asp Asp Ser Gln Asp Ala Leu Asn Lys
                340                 345                 350

Ala Ala Gln Asn Ile Gln Val Lys Ile Glu Glu Lys Ile Ser Gln Glu
                355                 360                 365

Gly Gln Thr Gln Trp Leu Lys Asp Asp Ile Ser Lys Phe Val Asp Ser
                370                 375                 380

Gln Ser Asn Trp Asn Ile Ala Ser Glu Ser Lys Gly Thr Asp His Leu
385                 390                 395                 400

Gln Gly Gly Ala Leu Leu Tyr Val Asn Ser Asp Lys Thr Pro Asp Ala
                405                 410                 415

Asn Ser Asp Tyr Arg Leu Leu Asn Arg Thr Pro Thr Asn Gln Thr Gly
                420                 425                 430

Thr Pro Leu Tyr Thr Thr Asp Pro Thr Gln Gly Gly Tyr Asp Phe Leu
                435                 440                 445

Leu Ala Asn Asp Val Asp Asn Ser Asn Pro Val Val Gln Ala Glu Gln
                450                 455                 460

Leu Asn Trp Met Tyr Tyr Leu Leu Asn Phe Gly Ser Ile Thr Asn Asn
465                 470                 475                 480
```

```
Asp Ala Asp Ala Asn Phe Asp Ser Ile Arg Val Asp Ala Val Asp Asn
            485                 490                 495
Val Asp Ala Asp Leu Leu Gln Ile Ala Ala Asp Tyr Phe Lys Ala Ala
            500                 505                 510
Tyr Gly Val Asp Lys Ser Asp Ala Ile Ser Asn Gln His Val Ser Ile
            515                 520                 525
Leu Glu Asp Trp Ser Asp Asn Asp Ala Glu Tyr Val Lys Asp Asn Gly
            530                 535                 540
Asp Asn Gln Leu Ser Met Asp Asn Lys Leu Arg Leu Ser Leu Lys Tyr
545                 550                 555                 560
Ser Leu Thr Met Pro Ala Val Asp Gln Tyr Gly Asn Lys Arg Ser Gly
            565                 570                 575
Leu Glu Pro Phe Leu Thr Asn Ser Leu Val Asp Arg Thr Asn Asp Ser
            580                 585                 590
Thr Asp Asn Thr Ala Gln Pro Asn Tyr Ser Phe Val Arg Ala His Asp
            595                 600                 605
Ser Glu Val Gln Thr Val Ile Ala Glu Ile Ile Lys Gln Arg Ile Asp
            610                 615                 620
Pro Asp Ser Asp Gly Leu Ser Pro Thr Met Asp Gln Leu Thr Glu Ala
625                 630                 635                 640
Phe Lys Ile Tyr Asn Ala Asp Gln Leu Lys Thr Asp Lys Glu Phe Thr
            645                 650                 655
Gln Tyr Asn Ile Pro Ser Thr Tyr Ala Thr Ile Leu Thr Asn Lys Asp
            660                 665                 670
Thr Val Pro Arg Val Tyr Tyr Gly Asp Met Tyr Thr Asp Asp Gly Gln
            675                 680                 685
Tyr Met Ala Thr Lys Ser Leu Tyr Tyr Asp Ala Ile Asp Thr Leu Leu
            690                 695                 700
Lys Ser Arg Ile Lys Tyr Val Ser Gly Gly Gln Thr Met Ser Met Lys
705                 710                 715                 720
Tyr Met Gln Gly Asp Ser Ser Met Ala Ala Asp Ser Tyr Arg Gly Ile
            725                 730                 735
Leu Thr Ser Val Arg Tyr Gly Asn Gly Ala Met Thr Ala Thr Asp Ala
            740                 745                 750
Gly Thr Asn Glu Thr Arg Thr Gln Gly Ile Ala Val Ile Glu Ser Asn
            755                 760                 765
Asn Pro Asp Leu Lys Leu Ser Ser Thr Asp Gln Val Val Asp Met
            770                 775                 780
Gly Ile Ala His Lys Asn Gln Ala Tyr Arg Pro Ala Leu Leu Thr Thr
785                 790                 795                 800
Lys Asp Gly Ile Asp Thr Tyr Val Ser Asp Ser Asp Val Ser Gln Ser
            805                 810                 815
Leu Ile Arg Tyr Thr Asn Ser Asn Gly Gln Leu Ile Phe Asn Ser Ser
            820                 825                 830
Asp Ile Val Gly Thr Ala Asn Pro Gln Val Ser Gly Tyr Leu Ala Val
            835                 840                 845
Trp Val Pro Val Gly Ala Ser Asp Thr Gln Asp Ala Arg Thr Glu Ser
            850                 855                 860
Ser Thr Ala Thr Thr Ala Asp Gly Gln Thr Leu His Ser Asn Ala Ala
865                 870                 875                 880
Leu Asp Ser Gln Val Ile Tyr Glu Ser Phe Ser Asn Phe Gln Ser Thr
            885                 890                 895
```

```
Pro Thr Thr Glu Ala Glu Tyr Ala Asn Val Gln Ile Ala Asn Asn Thr
        900                 905                 910

Asp Leu Tyr Lys Ser Trp Gly Ile Thr Asn Phe Glu Phe Pro Pro Gln
        915                 920                 925

Tyr Arg Ser Ser Thr Asp Ser Ser Phe Leu Asp Ser Ile Ile Gln Asn
        930                 935                 940

Gly Tyr Ala Phe Thr Asp Arg Tyr Asp Leu Gly Phe Asn Thr Pro Thr
945                 950                 955                 960

Lys Tyr Gly Thr Val Asp Gln Leu Arg Thr Ala Ile Lys Ala Leu His
            965                 970                 975

Ala Thr Gly Ile Lys Ala Met Ala Asp Trp Val Pro Asp Gln Ile Tyr
            980                 985                 990

Asn Leu Thr Gly Lys Glu Val Val Ala Val Gln Arg Val Asn Asn Ser
            995                 1000                1005

Gly Ile Tyr Asn Gln Asp Ser Val Ile Asn Lys Thr Leu Tyr Ala
        1010                1015                1020

Ser Gln Thr Val Gly Gly Glu Tyr Gln Ala Leu Tyr Gly Gly
    1025                1030                1035

Glu Phe Leu Asp Glu Ile Lys Lys Leu Tyr Pro Ser Leu Phe Glu
    1040                1045                1050

Lys Asn Gln Ile Ser Thr Gly Val Pro Met Asp Ala Ser Glu Lys
    1055                1060                1065

Ile Lys Glu Trp Ser Ala Lys Tyr Phe Asn Gly Thr Asn Ile Gln
    1070                1075                1080

Gly Arg Gly Ala Tyr Tyr Val Leu Lys Asp Trp Ala Thr Asn Glu
    1085                1090                1095

Tyr Phe Lys Val Ser Thr Ser Ser Asn Ser Ser Val Phe Leu Pro
    1100                1105                1110

Lys Gln Leu Thr Asn Glu Glu Ser Asn Thr Gly Phe Ile Ser Thr
    1115                1120                1125

Asp Gly Gly Met Thr Tyr Tyr Ser Thr Ser Gly Tyr Gln Ala Lys
    1130                1135                1140

Asp Thr Phe Ile Gln Asp Asp Lys Ser Asn Trp Tyr Tyr Phe Asp
    1145                1150                1155

Lys Asn Gly Tyr Met Thr Tyr Gly Phe Gln Thr Val Asn Asp Asn
    1160                1165                1170

Asn Tyr Tyr Phe Leu Pro Asn Gly Ile Glu Leu Gln Asp Ala Ile
    1175                1180                1185

Leu Glu Asp Ser Lys Gly Asn Val Tyr Tyr Phe Asn Gln Tyr Gly
    1190                1195                1200

Lys Gln Ala Val Asp Gly Tyr Tyr Met Leu Ala Asn Lys Thr Trp
    1205                1210                1215

Arg Tyr Phe Asp Lys Asn Gly Val Met Ala Asn Ala Gly Leu Thr
    1220                1225                1230

Thr Val Thr Val Asp Gly Gln Glu His Ile Gln Tyr Phe Asp Lys
    1235                1240                1245

Asn Gly Ile Gln Val Lys Gly Thr Ser Val Lys Asp Ala Asp Gly
    1250                1255                1260

Lys Leu Arg Tyr Phe Asp Thr Asp Ser Gly Asp Met Val Thr Asn
    1265                1270                1275

Arg Phe Gly Glu Asn Thr Asp Gly Thr Trp Ser Tyr Phe Gly Ala
    1280                1285                1290

Asp Gly Ile Ala Val Thr Gly Ala Gln Thr Ile Ser Gly Gln Lys
```

| | | | | | | | | | | |
|---|---|---|---|---|---|---|---|---|---|---|
| | | 1295 | | | 1300 | | | 1305 | | |
| Leu | Phe | Phe | Asp | Ala | Asp | Gly | Gln | Gln | Ile | Lys | Gly | Lys | Glu | Ala |
| | 1310 | | | | 1315 | | | | 1320 | |

Thr Asp Lys Lys Gly Lys Val His Tyr Tyr Asp Ala Asn Ser Gly
    1325                1330                1335

Glu Met Ile Thr Asn Arg Phe Glu Lys Leu Ser Asp Gly Ser Trp
    1340                1345                1350

Ala Tyr Phe Asn Lys Lys Gly Asn Ile Val Thr Gly Ala Gln Val
    1355                1360                1365

Ile Asn Gly Gln His Leu Phe Phe Glu Ser Asn Gly Asn Gln Val
    1370                1375                1380

Lys Gly Arg Glu Tyr Thr Ala Thr Asp Gly Lys Met Arg Tyr Tyr
    1385                1390                1395

Asp Ala Asp Ser Gly Asp Met Val Thr Asn Arg Phe Glu Arg Ile
    1400                1405                1410

Ser Asp Gly Ser Trp Ala Tyr Phe Gly Ala Asn Gly Val Ala Val
    1415                1420                1425

Thr Gly Glu Gln Asn Ile Asn Gly Gln Gln Leu Tyr Phe Asp Ala
    1430                1435                1440

Asn Gly His Gln Val Lys Gly Ala Ala Val Thr Gln Ala Asp Gly
    1445                1450                1455

Ser Gln Lys Tyr Tyr Asp Ala Asn Ser Gly Glu Met Ile Lys Ser
    1460                1465                1470

<210> SEQ ID NO 7
<211> LENGTH: 4584
<212> TYPE: DNA
<213> ORGANISM: Leuconostoc mesenteroides

<400> SEQUENCE: 7

```
atgccattta cagaaaaagt aatgcggaaa aagctttata agttgggaaa agttgggta      60
gttggtgggg tttgtgcttt tgcattaacc gcctcatttg ctttagcaac accaagtgtt    120
ttgggagaca gtagtgtacc tgatgtgagt gcgaataacg ttcaatctgc ttcagataat    180
acaacggata cgcagcagaa cactacggtt accgaagaaa tgataaaagt acagtctgca    240
gctactaatg ataatgtaac aacagctgca agcgacacaa cgcaatctgc tgataataat    300
gtgacagaaa acagtcaga tgatcatgca cttgataatg aaaaagtcga taacaaacaa    360
gatgaagtcg ctcaaaccaa tgttactagc aaagatgagg aatcagcagt tgcttcaact    420
gacactgatc ctgctgaaac gacaactgac gaaacacaac aagttagcgg caagtacgtt    480
gaaaaagacg gtagttggta ttattatttt gatgatggca aaaatgctaa aggtttatca    540
acgatagaca caatattca atattttgac gagagtggta acaagtcaa aggacagtat    600
gtcacaattg ataatcaaac atattatttt gataaggact caggtgatga gttaactggt    660
ctgcaaagca ttgatgggaa catagttgct tttaacgatg aagggcaaca aattttttaat    720
caatattacc aatctgaaaa tggtacaaca tactattttg atgataaagg catgctgct    780
accggtatta gaatatcga aggcaaaaat tattattttg ataatcttgg gcaactaaaa    840
aaaggcttct ctggtgtgat tgatggtcaa ataatgacat tgatcagga acagggcaa    900
gaagtttcta acacaacttc tgaaataaaa gaaggtttga cgacacaaaa cacggattat    960
agcgaacata tgcagcccca cggtacggat gctgaggact tgaaaatat tgacggctat   1020
ttaacagcta gttcatggta tcgtccaaca gatatttac gtaacggaac agactgggaa   1080
```

```
ccttctacag atacagattt cagaccaata ttgtcagtgt ggtggccaga taagaacacc      1140
caggtcaact attaaaatta catggctgat ttagggttta tcagtaatgc ggacagtttt      1200
gaaactgggg atagccaaag cttattaaat gaagcaagta actatgttca aaaatcaatt      1260
gaaatgaaaa ttagtgcgca acaaagtaca gagtggttaa aggatgcaat ggcggccttc      1320
attgtcacgc aaccacagtg gaatgaaact agtgaagata tgagcaatga ccatttacaa      1380
aatggcgcat taacttatgt caacagtcca ctgacacctg atgctaattc aaactttaga      1440
ctacttaatc ggacaccaac aaaccagact ggtgaacaag cgtataattt agataattca      1500
aaaggtggtt ttgaattgtt gttagccaat gacgttgata attcaaaccc tgtagtacaa      1560
gcagaacaat tgaattggtt atattattta atgaattttg gtacgattac ggccaacgac      1620
gcggatgcta attttgatgg tattcgtgta gatgcagtcg acaatgtgga tgctgatttg      1680
ttacaaattg ctgccgatta tttcaaacta gcttacggtg ttgatcaaaa tgatgctact      1740
gctaatcagc atctttcaat tttggaagat tggagtcaca atgatccttt gtatgtaaca      1800
gatcaaggaa gcaatcaatt aaccatggat gattatgtgc acacacaatt aatctggtct      1860
ctaacaaaat catctgacat acgaggtaca atgcagcgct tcgtggatta ttatatggtt      1920
gatcgatcta atgatagtac agaaaacgaa gccattccta attacagctt tgtacgtgca      1980
cacgacagcg aagtgcaaac ggttattgcc caaattgttt ccgatttgta tcctgatgtt      2040
gaaaatagtt tagcaccaac aacagaacaa ttggcagctg ctttcaaagt atacaatgaa      2100
gatgaaaaat tagcagacaa aaagtacaca caatataata tggctagtgc ttatgcgatg      2160
ttgctaacca ataaggatac tgttcctcgt gtctattatg cgatttata tacagatgat      2220 ggtcaatata tggcaacaaa gtcaccatac tatgatgcga ttaacacttt gctgaaggct      2280
agagtccaat atgttgctgg tggccaatcg atgtccgttg atagtaatga cgtgttaaca      2340
agtgttcgct atggtaaaga tgccatgacg gcttctgaca ctggaacatc tgagacgcgt      2400
actgaaggtg ttgggggtcat cgtcagcaac aacgcggaac tacaattaga ggatgggcat      2460
acagtcacat tgcacatggg ggcagctcat aagaaccaag cttatcgtgc tttgttatca      2520
acaactgcag atggattagc ttattatgat actgatgaaa atgcacctgt ggcgtacaca      2580
gatgctaacg gcgatttgat ttttacgaat gaatcaattt atggtgtaca aaatccacaa      2640
gtttctggtt acttggcagt ttgggttccg gtaggtgcgc aacaagatca agatgcacga      2700
acggcctctg atacaacaac aaacacgagt gataaagtgt tccattcaaa cgctgctctt      2760
gattctcaag tcatctacga aggtttctca aacttccaag catttgctac agacagcagt      2820
gaatatacaa acgtagtcat cgctcagaat gcggaccaat ttaagcaatg gggtgtgaca      2880
agcttccaat tggcaccaca atatcgttca agtacagata caagtttctt ggattcaatt      2940
attcaaaacg ggtatgcatt cacggatcgt tatgacttag gttatggcac accgacaaaa      3000
tatggaactg ctgatcagtt gcgcgatgct attaaagcct acatgctag cggtattcaa      3060 gccattgccg attgggtgcc ggaccaaatt tataatttgc cagagcaaga attagctact      3120
gtcacaagaa caaattcatt tggagatgac gatacagatt ctgatattga caatgcctta      3180
tatgttgtac aaagtcgtgg gggtggtcaa tatcaagaga tgtatggtgg tgccttctta      3240
gaagagttac aggcactcta tccatcccta tttaaagtga atcaaatctc aactggcgtt      3300
ccaattgatg gcagtgtaaa gattactgag tgggcggcta agtacttcaa tggctctaac      3360
atccaaggta aaggtgctgg atacgtattg aaagatatgg gttctaataa gtattttaag      3420
gtcgtttcga acactgaaga tggtgactac ttaccaaaac agttaactaa tgatctgtca      3480
```

```
gaaactggct ttacacacga tgataaagga atcatctatt atacattaag tggttatcgt    3540
gcccaaaatg catttattca agatgatgat aataactatt actatttga taaaacaggt     3600
catttagtaa caggtttgca aaagattaat aaccatacct acttcttctt acctaatggt    3660
atcgaactgg tcaagagctt cttacaaaac gaagatggta caattgttta tttcgataag    3720
aaaggtcatc aagttttga ccaatatata actgatcaaa atggaaatgc gtattacttt     3780
gatgatgctg tgtaatgct taaatcaggg cttgcaacga ttgatggaca tcaacagtat     3840
tttgatcaaa atggtgtgca ggttaaggat aagtttgtga ttggcactga tggttataag    3900
tattactttg aaccaggtag tggtaactta gctatcctac gttatgtgca aaacagtaag    3960
aatcaatggt tctatttga tggtaatggc catgctgtca ctggtttcca aacaattaat     4020
ggtaagaaac aatatttcta taatgatggt catcaaagta aaggtgaatt cattgatgca    4080
gacggtgata ctttctatac gagtgccact gatggtcgcc tagtaactgg tgttcagaag    4140
attaatggta ttacctatgc ttttgataac acaggaaatt tgatcacaaa tcagtattat    4200
caattagcag atggtaaata tatgttgtta gatgatagtg gtcgtgcgaa acagggttt     4260
gtattgcaag atggtgtact aagatacttc gatcaaaacg tgagcaagt gaaagatgct     4320
atcattgtgg atccagatac taacttgagt tattatttca atgcaacaca aggtgtcgct    4380
gtaaaaaatg attatttcga gtatcaaggt aattggtatt taacagatgc taattatcaa    4440
cttatcaaag gttttaaagc agttgacgac agcttacaac attttgatga agtcactggt    4500
gtacaaacaa aagatagtgc tttaataagt gctcagggta aggtttacca atttgataat    4560
aatggaaatg ctgtgtcagc ataa                                           4584
```

<210> SEQ ID NO 8
<211> LENGTH: 1527
<212> TYPE: PRT
<213> ORGANISM: Leuconostoc mesenteroides

<400> SEQUENCE: 8

```
Met Pro Phe Thr Glu Lys Val Met Arg Lys Lys Leu Tyr Lys Val Gly
1               5                   10                  15

Lys Ser Trp Val Val Gly Gly Val Cys Ala Phe Ala Leu Thr Ala Ser
            20                  25                  30

Phe Ala Leu Ala Thr Pro Ser Val Leu Gly Asp Ser Ser Val Pro Asp
        35                  40                  45

Val Ser Ala Asn Asn Val Gln Ser Ala Ser Asp Asn Thr Thr Asp Thr
    50                  55                  60

Gln Gln Asn Thr Thr Val Thr Glu Glu Asn Asp Lys Val Gln Ser Ala
65                  70                  75                  80

Ala Thr Asn Asp Asn Val Thr Thr Ala Ala Ser Asp Thr Thr Gln Ser
                85                  90                  95

Ala Asp Asn Asn Val Thr Glu Lys Gln Ser Asp His Ala Leu Asp
            100                 105                 110

Asn Glu Lys Val Asp Asn Lys Gln Asp Glu Val Ala Gln Thr Asn Val
        115                 120                 125

Thr Ser Lys Asp Glu Glu Ser Ala Val Ala Ser Thr Asp Thr Asp Pro
    130                 135                 140

Ala Glu Thr Thr Thr Asp Glu Thr Gln Gln Val Ser Gly Lys Tyr Val
145                 150                 155                 160

Glu Lys Asp Gly Ser Trp Tyr Tyr Tyr Phe Asp Asp Gly Lys Asn Ala
                165                 170                 175
```

```
Lys Gly Leu Ser Thr Ile Asp Asn Asn Ile Gln Tyr Phe Asp Glu Ser
            180                 185                 190

Gly Lys Gln Val Lys Gly Gln Tyr Val Thr Ile Asp Asn Gln Thr Tyr
            195                 200                 205

Tyr Phe Asp Lys Asp Ser Gly Asp Glu Leu Thr Gly Leu Gln Ser Ile
    210                 215                 220

Asp Gly Asn Ile Val Ala Phe Asn Asp Glu Gly Gln Gln Ile Phe Asn
225                 230                 235                 240

Gln Tyr Tyr Gln Ser Glu Asn Gly Thr Thr Tyr Tyr Phe Asp Asp Lys
                245                 250                 255

Gly His Ala Ala Thr Gly Ile Lys Asn Ile Glu Gly Lys Asn Tyr Tyr
                260                 265                 270

Phe Asp Asn Leu Gly Gln Leu Lys Lys Gly Phe Ser Gly Val Ile Asp
            275                 280                 285

Gly Gln Ile Met Thr Phe Asp Gln Glu Thr Gly Gln Glu Val Ser Asn
            290                 295                 300

Thr Thr Ser Glu Ile Lys Glu Gly Leu Thr Thr Gln Asn Thr Asp Tyr
305                 310                 315                 320

Ser Glu His Asn Ala Ala His Gly Thr Asp Ala Glu Asp Phe Glu Asn
                325                 330                 335

Ile Asp Gly Tyr Leu Thr Ala Ser Ser Trp Tyr Arg Pro Thr Asp Ile
                340                 345                 350

Leu Arg Asn Gly Thr Asp Trp Glu Pro Ser Thr Asp Thr Asp Phe Arg
            355                 360                 365

Pro Ile Leu Ser Val Trp Trp Pro Asp Lys Asn Thr Gln Val Asn Tyr
370                 375                 380

Leu Asn Tyr Met Ala Asp Leu Gly Phe Ile Ser Asn Ala Asp Ser Phe
385                 390                 395                 400

Glu Thr Gly Asp Ser Gln Ser Leu Leu Asn Glu Ala Ser Asn Tyr Val
                405                 410                 415

Gln Lys Ser Ile Glu Met Lys Ile Ser Ala Gln Gln Ser Thr Glu Trp
                420                 425                 430

Leu Lys Asp Ala Met Ala Ala Phe Ile Val Thr Gln Pro Gln Trp Asn
            435                 440                 445

Glu Thr Ser Glu Asp Met Ser Asn Asp His Leu Gln Asn Gly Ala Leu
            450                 455                 460

Thr Tyr Val Asn Ser Pro Leu Thr Pro Asp Ala Asn Ser Asn Phe Arg
465                 470                 475                 480

Leu Leu Asn Arg Thr Pro Thr Asn Gln Thr Gly Glu Gln Ala Tyr Asn
                485                 490                 495

Leu Asp Asn Ser Lys Gly Gly Phe Glu Leu Leu Leu Ala Asn Asp Val
                500                 505                 510

Asp Asn Ser Asn Pro Val Val Gln Ala Glu Gln Leu Asn Trp Leu Tyr
            515                 520                 525

Tyr Leu Met Asn Phe Gly Thr Ile Thr Ala Asn Asp Ala Asp Ala Asn
            530                 535                 540

Phe Asp Gly Ile Arg Val Asp Ala Val Asp Asn Val Asp Ala Asp Leu
545                 550                 555                 560

Leu Gln Ile Ala Ala Asp Tyr Phe Lys Leu Ala Tyr Gly Val Asp Gln
                565                 570                 575

Asn Asp Ala Thr Ala Asn Gln His Leu Ser Ile Leu Glu Asp Trp Ser
                580                 585                 590
```

-continued

```
His Asn Asp Pro Leu Tyr Val Thr Asp Gln Gly Ser Asn Gln Leu Thr
            595                 600                 605
Met Asp Asp Tyr Val His Thr Gln Leu Ile Trp Ser Leu Thr Lys Ser
610                 615                 620
Ser Asp Ile Arg Gly Thr Met Gln Arg Phe Val Asp Tyr Tyr Met Val
625                 630                 635                 640
Asp Arg Ser Asn Asp Ser Thr Glu Asn Glu Ala Ile Pro Asn Tyr Ser
                645                 650                 655
Phe Val Arg Ala His Asp Ser Glu Val Gln Thr Val Ile Ala Gln Ile
                660                 665                 670
Val Ser Asp Leu Tyr Pro Asp Val Glu Asn Ser Leu Ala Pro Thr Thr
            675                 680                 685
Glu Gln Leu Ala Ala Ala Phe Lys Val Tyr Asn Glu Asp Glu Lys Leu
            690                 695                 700
Ala Asp Lys Lys Tyr Thr Gln Tyr Asn Met Ala Ser Ala Tyr Ala Met
705                 710                 715                 720
Leu Leu Thr Asn Lys Asp Thr Val Pro Arg Val Tyr Tyr Gly Asp Leu
                725                 730                 735
Tyr Thr Asp Asp Gly Gln Tyr Met Ala Thr Lys Ser Pro Tyr Tyr Asp
                740                 745                 750
Ala Ile Asn Thr Leu Leu Lys Ala Arg Val Gln Tyr Val Ala Gly Gly
            755                 760                 765
Gln Ser Met Ser Val Asp Ser Asn Asp Val Leu Thr Ser Val Arg Tyr
            770                 775                 780
Gly Lys Asp Ala Met Thr Ala Ser Asp Thr Gly Thr Ser Glu Thr Arg
785                 790                 795                 800
Thr Glu Gly Val Gly Val Ile Val Ser Asn Asn Ala Glu Leu Gln Leu
                805                 810                 815
Glu Asp Gly His Thr Val Thr Leu His Met Gly Ala Ala His Lys Asn
                820                 825                 830
Gln Ala Tyr Arg Ala Leu Leu Ser Thr Thr Ala Asp Gly Leu Ala Tyr
            835                 840                 845
Tyr Asp Thr Asp Glu Asn Ala Pro Val Ala Tyr Thr Asp Ala Asn Gly
            850                 855                 860
Asp Leu Ile Phe Thr Asn Glu Ser Ile Tyr Gly Val Gln Asn Pro Gln
865                 870                 875                 880
Val Ser Gly Tyr Leu Ala Val Trp Val Pro Val Gly Ala Gln Gln Asp
                885                 890                 895
Gln Asp Ala Arg Thr Ala Ser Asp Thr Thr Asn Thr Ser Asp Lys
            900                 905                 910
Val Phe His Ser Asn Ala Ala Leu Asp Ser Gln Val Ile Tyr Glu Gly
            915                 920                 925
Phe Ser Asn Phe Gln Ala Phe Ala Thr Asp Ser Ser Glu Tyr Thr Asn
930                 935                 940
Val Val Ile Ala Gln Asn Ala Asp Gln Phe Lys Gln Trp Gly Val Thr
945                 950                 955                 960
Ser Phe Gln Leu Ala Pro Gln Tyr Arg Ser Ser Thr Asp Thr Ser Phe
                965                 970                 975
Leu Asp Ser Ile Ile Gln Asn Gly Tyr Ala Phe Thr Asp Arg Tyr Asp
                980                 985                 990
Leu Gly Tyr Gly Thr Pro Thr Lys  Tyr Gly Thr Ala Asp  Gln Leu Arg
            995                 1000                 1005
Asp Ala  Ile Lys Ala Leu His  Ala Ser Gly Ile Gln  Ala Ile Ala
```

```
            1010                1015                1020

Asp Trp Val Pro Asp Gln Ile Tyr Asn Leu Pro Glu Gln Glu Leu
            1025                1030                1035

Ala Thr Val Thr Arg Thr Asn Ser Phe Gly Asp Asp Thr Asp
        1040                1045                1050

Ser Asp Ile Asp Asn Ala Leu Tyr Val Val Gln Ser Arg Gly Gly
        1055                1060                1065

Gly Gln Tyr Gln Glu Met Tyr Gly Gly Ala Phe Leu Glu Glu Leu
        1070                1075                1080

Gln Ala Leu Tyr Pro Ser Leu Phe Lys Val Asn Gln Ile Ser Thr
        1085                1090                1095

Gly Val Pro Ile Asp Gly Ser Val Lys Ile Thr Glu Trp Ala Ala
        1100                1105                1110

Lys Tyr Phe Asn Gly Ser Asn Ile Gln Gly Lys Gly Ala Gly Tyr
        1115                1120                1125

Val Leu Lys Asp Met Gly Ser Asn Lys Tyr Phe Lys Val Val Ser
        1130                1135                1140

Asn Thr Glu Asp Gly Asp Tyr Leu Pro Lys Gln Leu Thr Asn Asp
        1145                1150                1155

Leu Ser Glu Thr Gly Phe Thr His Asp Asp Lys Gly Ile Ile Tyr
        1160                1165                1170

Tyr Thr Leu Ser Gly Tyr Arg Ala Gln Asn Ala Phe Ile Gln Asp
        1175                1180                1185

Asp Asp Asn Asn Tyr Tyr Phe Asp Lys Thr Gly His Leu Val
        1190                1195                1200

Thr Gly Leu Gln Lys Ile Asn Asn His Thr Tyr Phe Phe Leu Pro
        1205                1210                1215

Asn Gly Ile Glu Leu Val Lys Ser Phe Leu Gln Asn Glu Asp Gly
        1220                1225                1230

Thr Ile Val Tyr Phe Asp Lys Lys Gly His Gln Val Phe Asp Gln
        1235                1240                1245

Tyr Ile Thr Asp Gln Asn Gly Asn Ala Tyr Tyr Phe Asp Asp Ala
        1250                1255                1260

Gly Val Met Leu Lys Ser Gly Leu Ala Thr Ile Asp Gly His Gln
        1265                1270                1275

Gln Tyr Phe Asp Gln Asn Gly Val Gln Val Lys Asp Lys Phe Val
        1280                1285                1290

Ile Gly Thr Asp Gly Tyr Lys Tyr Tyr Phe Glu Pro Gly Ser Gly
        1295                1300                1305

Asn Leu Ala Ile Leu Arg Tyr Val Gln Asn Ser Lys Asn Gln Trp
        1310                1315                1320

Phe Tyr Phe Asp Gly Asn Gly His Ala Val Thr Gly Phe Gln Thr
        1325                1330                1335

Ile Asn Gly Lys Lys Gln Tyr Phe Tyr Asn Asp Gly His Gln Ser
        1340                1345                1350

Lys Gly Glu Phe Ile Asp Ala Asp Gly Asp Thr Phe Tyr Thr Ser
        1355                1360                1365

Ala Thr Asp Gly Arg Leu Val Thr Gly Val Gln Lys Ile Asn Gly
        1370                1375                1380

Ile Thr Tyr Ala Phe Asp Asn Thr Gly Asn Leu Ile Thr Asn Gln
        1385                1390                1395

Tyr Tyr Gln Leu Ala Asp Gly Lys Tyr Met Leu Leu Asp Asp Ser
        1400                1405                1410
```

```
Gly Arg Ala Lys Thr Gly Phe Val Leu Gln Asp Gly Val Leu Arg
1415                1420                1425

Tyr Phe Asp Gln Asn Gly Glu Gln Val Lys Asp Ala Ile Ile Val
    1430                1435                1440

Asp Pro Asp Thr Asn Leu Ser Tyr Tyr Phe Asn Ala Thr Gln Gly
1445                1450                1455

Val Ala Val Lys Asn Asp Tyr Phe Glu Tyr Gln Gly Asn Trp Tyr
1460                1465                1470

Leu Thr Asp Ala Asn Tyr Gln Leu Ile Lys Gly Phe Lys Ala Val
1475                1480                1485

Asp Asp Ser Leu Gln His Phe Asp Glu Val Thr Gly Val Gln Thr
1490                1495                1500

Lys Asp Ser Ala Leu Ile Ser Ala Gln Gly Lys Val Tyr Gln Phe
1505                1510                1515

Asp Asn Asn Gly Asn Ala Val Ser Ala
1520                1525

<210> SEQ ID NO 9
<211> LENGTH: 1485
<212> TYPE: PRT
<213> ORGANISM: Leuconostoc mesenteroides

<400> SEQUENCE: 9

Asp Ser Ser Val Pro Asp Val Ser Ala Asn Asn Val Gln Ser Ser
1               5                   10                  15

Asp Asn Thr Thr Asp Thr Gln Gln Asn Thr Thr Val Thr Glu Glu Asn
                20                  25                  30

Asp Lys Val Gln Ser Ala Ala Thr Asn Asp Asn Val Thr Thr Ala Ala
        35                  40                  45

Ser Asp Thr Thr Gln Ser Ala Asp Asn Asn Val Thr Glu Lys Gln Ser
50                  55                  60

Asp Asp His Ala Leu Asp Asn Glu Lys Val Asp Asn Lys Gln Asp Glu
65                  70                  75                  80

Val Ala Gln Thr Asn Val Thr Ser Lys Asp Glu Glu Ser Ala Val Ala
                85                  90                  95

Ser Thr Asp Thr Asp Pro Ala Glu Thr Thr Thr Asp Glu Thr Gln Gln
            100                 105                 110

Val Ser Gly Lys Tyr Val Glu Lys Asp Gly Ser Trp Tyr Tyr Tyr Phe
        115                 120                 125

Asp Asp Gly Lys Asn Ala Lys Gly Leu Ser Thr Ile Asp Asn Asn Ile
130                 135                 140

Gln Tyr Phe Asp Glu Ser Gly Lys Gln Val Lys Gly Gln Tyr Val Thr
145                 150                 155                 160

Ile Asp Asn Gln Thr Tyr Tyr Phe Asp Lys Asp Ser Gly Asp Glu Leu
                165                 170                 175

Thr Gly Leu Gln Ser Ile Asp Gly Asn Ile Val Ala Phe Asn Asp Glu
            180                 185                 190

Gly Gln Gln Ile Phe Asn Gln Tyr Tyr Gln Ser Glu Asn Gly Thr Thr
        195                 200                 205

Tyr Tyr Phe Asp Asp Lys Gly His Ala Ala Thr Gly Ile Lys Asn Ile
    210                 215                 220

Glu Gly Lys Asn Tyr Tyr Phe Asp Asn Leu Gly Gln Leu Lys Lys Gly
225                 230                 235                 240

Phe Ser Gly Val Ile Asp Gly Gln Ile Met Thr Phe Asp Gln Glu Thr
```

-continued

```
                245                 250                 255
Gly Gln Glu Val Ser Asn Thr Thr Ser Glu Ile Lys Glu Gly Leu Thr
                260                 265                 270

Thr Gln Asn Thr Asp Tyr Ser Glu His Asn Ala Ala His Gly Thr Asp
            275                 280                 285

Ala Glu Asp Phe Glu Asn Ile Asp Gly Tyr Leu Thr Ala Ser Ser Trp
        290                 295                 300

Tyr Arg Pro Thr Asp Ile Leu Arg Asn Gly Thr Asp Trp Glu Pro Ser
305                 310                 315                 320

Thr Asp Thr Asp Phe Arg Pro Ile Leu Ser Val Trp Trp Pro Asp Lys
                325                 330                 335

Asn Thr Gln Val Asn Tyr Leu Asn Tyr Met Ala Asp Leu Gly Phe Ile
            340                 345                 350

Ser Asn Ala Asp Ser Phe Glu Thr Gly Asp Ser Gln Ser Leu Leu Asn
        355                 360                 365

Glu Ala Ser Asn Tyr Val Gln Lys Ser Ile Glu Met Lys Ile Ser Ala
    370                 375                 380

Gln Gln Ser Thr Glu Trp Leu Lys Asp Ala Met Ala Ala Phe Ile Val
385                 390                 395                 400

Thr Gln Pro Gln Trp Asn Glu Thr Ser Glu Asp Met Ser Asn Asp His
                405                 410                 415

Leu Gln Asn Gly Ala Leu Thr Tyr Val Asn Ser Pro Leu Thr Pro Asp
            420                 425                 430

Ala Asn Ser Asn Phe Arg Leu Leu Asn Arg Thr Pro Thr Asn Gln Thr
        435                 440                 445

Gly Glu Gln Ala Tyr Asn Leu Asp Asn Ser Lys Gly Gly Phe Glu Leu
    450                 455                 460

Leu Leu Ala Asn Asp Val Asp Asn Ser Asn Pro Val Val Gln Ala Glu
465                 470                 475                 480

Gln Leu Asn Trp Leu Tyr Tyr Leu Met Asn Phe Gly Thr Ile Thr Ala
                485                 490                 495

Asn Asp Ala Asp Ala Asn Phe Asp Gly Ile Arg Val Asp Ala Val Asp
            500                 505                 510

Asn Val Asp Ala Asp Leu Leu Gln Ile Ala Ala Asp Tyr Phe Lys Leu
        515                 520                 525

Ala Tyr Gly Val Asp Gln Asn Asp Ala Thr Ala Asn Gln His Leu Ser
    530                 535                 540

Ile Leu Glu Asp Trp Ser His Asn Asp Pro Leu Tyr Val Thr Asp Gln
545                 550                 555                 560

Gly Ser Asn Gln Leu Thr Met Asp Asp Tyr Val His Thr Gln Leu Ile
                565                 570                 575

Trp Ser Leu Thr Lys Ser Ser Asp Ile Arg Gly Thr Met Gln Arg Phe
            580                 585                 590

Val Asp Tyr Tyr Met Val Asp Arg Ser Asn Asp Ser Thr Glu Asn Glu
        595                 600                 605

Ala Ile Pro Asn Tyr Ser Phe Val Arg Ala His Asp Ser Glu Val Gln
    610                 615                 620

Thr Val Ile Ala Gln Ile Val Ser Asp Leu Tyr Pro Asp Val Glu Asn
625                 630                 635                 640

Ser Leu Ala Pro Thr Thr Glu Gln Leu Ala Ala Ala Phe Lys Val Tyr
                645                 650                 655

Asn Glu Asp Glu Lys Leu Ala Asp Lys Lys Tyr Thr Gln Tyr Asn Met
            660                 665                 670
```

```
Ala Ser Ala Tyr Ala Met Leu Leu Thr Asn Lys Asp Thr Val Pro Arg
            675                 680                 685

Val Tyr Tyr Gly Asp Leu Tyr Thr Asp Asp Gly Gln Tyr Met Ala Thr
690             695                 700

Lys Ser Pro Tyr Tyr Asp Ala Ile Asn Thr Leu Leu Lys Ala Arg Val
705                 710                 715                 720

Gln Tyr Val Ala Gly Gly Gln Ser Met Ser Val Asp Ser Asn Asp Val
            725                 730                 735

Leu Thr Ser Val Arg Tyr Gly Lys Asp Ala Met Thr Ala Ser Asp Thr
            740                 745                 750

Gly Thr Ser Glu Thr Arg Thr Glu Gly Val Gly Val Ile Val Ser Asn
            755                 760                 765

Asn Ala Glu Leu Gln Leu Glu Asp Gly His Thr Val Thr Leu His Met
            770                 775                 780

Gly Ala Ala His Lys Asn Gln Ala Tyr Arg Ala Leu Leu Ser Thr Thr
785                 790                 795                 800

Ala Asp Gly Leu Ala Tyr Tyr Asp Thr Asp Glu Asn Ala Pro Val Ala
            805                 810                 815

Tyr Thr Asp Ala Asn Gly Asp Leu Ile Phe Thr Asn Glu Ser Ile Tyr
            820                 825                 830

Gly Val Gln Asn Pro Gln Val Ser Gly Tyr Leu Ala Val Trp Val Pro
            835                 840                 845

Val Gly Ala Gln Gln Asp Gln Asp Ala Arg Thr Ala Ser Asp Thr Thr
            850                 855                 860

Thr Asn Thr Ser Asp Lys Val Phe His Ser Asn Ala Ala Leu Asp Ser
865                 870                 875                 880

Gln Val Ile Tyr Glu Gly Phe Ser Asn Phe Gln Ala Phe Ala Thr Asp
            885                 890                 895

Ser Ser Glu Tyr Thr Asn Val Val Ile Ala Gln Asn Ala Asp Gln Phe
            900                 905                 910

Lys Gln Trp Gly Val Thr Ser Phe Gln Leu Ala Pro Gln Tyr Arg Ser
            915                 920                 925

Ser Thr Asp Thr Ser Phe Leu Asp Ser Ile Ile Gln Asn Gly Tyr Ala
            930                 935                 940

Phe Thr Asp Arg Tyr Asp Leu Gly Tyr Gly Thr Pro Thr Lys Tyr Gly
945                 950                 955                 960

Thr Ala Asp Gln Leu Arg Asp Ala Ile Lys Ala Leu His Ala Ser Gly
            965                 970                 975

Ile Gln Ala Ile Ala Asp Trp Val Pro Asp Gln Ile Tyr Asn Leu Pro
            980                 985                 990

Glu Gln Glu Leu Ala Thr Val Thr Arg Thr Asn Ser Phe Gly Asp Asp
            995                 1000                1005

Asp Thr Asp Ser Asp Ile Asp Asn Ala Leu Tyr Val Val Gln Ser
            1010                1015                1020

Arg Gly Gly Gly Gln Tyr Gln Glu Met Tyr Gly Gly Ala Phe Leu
            1025                1030                1035

Glu Glu Leu Gln Ala Leu Tyr Pro Ser Leu Phe Lys Val Asn Gln
            1040                1045                1050

Ile Ser Thr Gly Val Pro Ile Asp Gly Ser Val Lys Ile Thr Glu
            1055                1060                1065

Trp Ala Ala Lys Tyr Phe Asn Gly Ser Asn Ile Gln Gly Lys Gly
            1070                1075                1080
```

```
Ala Gly Tyr Val Leu Lys Asp Met Gly Ser Asn Lys Tyr Phe Lys
    1085                1090                1095

Val Val Ser Asn Thr Glu Asp Gly Asp Tyr Leu Pro Lys Gln Leu
    1100                1105                1110

Thr Asn Asp Leu Ser Glu Thr Gly Phe Thr His Asp Asp Lys Gly
    1115                1120                1125

Ile Ile Tyr Tyr Thr Leu Ser Gly Tyr Arg Ala Gln Asn Ala Phe
    1130                1135                1140

Ile Gln Asp Asp Asn Asn Tyr Tyr Tyr Phe Asp Lys Thr Gly
    1145                1150                1155

His Leu Val Thr Gly Leu Gln Lys Ile Asn Asn His Thr Tyr Phe
    1160                1165                1170

Phe Leu Pro Asn Gly Ile Glu Leu Val Lys Ser Phe Leu Gln Asn
    1175                1180                1185

Glu Asp Gly Thr Ile Val Tyr Phe Asp Lys Lys Gly His Gln Val
    1190                1195                1200

Phe Asp Gln Tyr Ile Thr Asp Gln Asn Gly Asn Ala Tyr Tyr Phe
    1205                1210                1215

Asp Asp Ala Gly Val Met Leu Lys Ser Gly Leu Ala Thr Ile Asp
    1220                1225                1230

Gly His Gln Gln Tyr Phe Asp Gln Asn Gly Val Gln Val Lys Asp
    1235                1240                1245

Lys Phe Val Ile Gly Thr Asp Gly Tyr Lys Tyr Tyr Phe Glu Pro
    1250                1255                1260

Gly Ser Gly Asn Leu Ala Ile Leu Arg Tyr Val Gln Asn Ser Lys
    1265                1270                1275

Asn Gln Trp Phe Tyr Phe Asp Gly Asn Gly His Ala Val Thr Gly
    1280                1285                1290

Phe Gln Thr Ile Asn Gly Lys Lys Gln Tyr Phe Tyr Asn Asp Gly
    1295                1300                1305

His Gln Ser Lys Gly Glu Phe Ile Asp Ala Asp Gly Asp Thr Phe
    1310                1315                1320

Tyr Thr Ser Ala Thr Asp Gly Arg Leu Val Thr Gly Val Gln Lys
    1325                1330                1335

Ile Asn Gly Ile Thr Tyr Ala Phe Asp Asn Thr Gly Asn Leu Ile
    1340                1345                1350

Thr Asn Gln Tyr Tyr Gln Leu Ala Asp Gly Lys Tyr Met Leu Leu
    1355                1360                1365

Asp Asp Ser Gly Arg Ala Lys Thr Gly Phe Val Leu Gln Asp Gly
    1370                1375                1380

Val Leu Arg Tyr Phe Asp Gln Asn Gly Glu Gln Val Lys Asp Ala
    1385                1390                1395

Ile Ile Val Asp Pro Asp Thr Asn Leu Ser Tyr Tyr Phe Asn Ala
    1400                1405                1410

Thr Gln Gly Val Ala Val Lys Asn Asp Tyr Phe Glu Tyr Gln Gly
    1415                1420                1425

Asn Trp Tyr Leu Thr Asp Ala Asn Tyr Gln Leu Ile Lys Gly Phe
    1430                1435                1440

Lys Ala Val Asp Asp Ser Leu Gln His Phe Asp Glu Val Thr Gly
    1445                1450                1455

Val Gln Thr Lys Asp Ser Ala Leu Ile Ser Ala Gln Gly Lys Val
    1460                1465                1470

Tyr Gln Phe Asp Asn Asn Gly Asn Ala Val Ser Ala
```

<210> SEQ ID NO 10
<211> LENGTH: 4773
<212> TYPE: DNA
<213> ORGANISM: Streptococcus sobrinus

<400> SEQUENCE: 10

| | | | | | |
|---|---|---|---|---|---|
| atggagaaga | atgtacgttt | taagatgcat | aaggtgaaaa | agagatgggt | aaccctctct | 60 |
| gtcgcatctg | ccaccatgtt | ggcatcagcc | cttggtgctt | cagtagctag | tgcggataca | 120 |
| gacactgcta | gtgatgatag | caaccaaacc | gtggtaactg | gtgaccagac | tactaacaat | 180 |
| caagccactg | accagacttc | tattgcagca | acagctacat | cagaacagtc | tgcttcaact | 240 |
| gatgcagcaa | cagatcaagc | atcagcagca | gagcaaactc | aaggaacaac | agctagcaca | 300 |
| gacacggcag | ctcaaacaac | cacaaatgct | aatgaagcta | agtgggttcc | gactgaaaat | 360 |
| gagaaccaag | ttttacaga | tgagatgtta | gcagaagcca | agaatgtggc | tactgctgaa | 420 |
| tctgattcaa | ttccatcaga | cttggctaaa | atgtcaaatg | ttaagcaggt | tgacggtaaa | 480 |
| tattattact | acgaccaaga | tggcaatgtt | aagaaaaact | ttgctgtcag | cgttggtgat | 540 |
| aagatttatt | actttgatga | aactggcgct | acaaggaca | ctagcaaggt | tgatgccgac | 600 |
| aagtccagtt | cagctgtaag | tcaaaatgca | acaatatttg | cagctaataa | ccgtgcctac | 660 |
| agcacctcag | ctaaaaattt | tgaagccgtt | gataactacc | tgcagctga | ctcttggtat | 720 |
| cgtccaaaat | caatcctgaa | agacggaaaa | acttggacag | aatctggcaa | agatgacttc | 780 |
| cgcccgcttc | tcatggcttg | gtggcctgat | accgaaacca | acgtaacta | cgttaattac | 840 |
| atgaacaagg | ttgttggtat | tgataagacc | tataccgctg | aaaccagcca | agctgattta | 900 |
| acggcagcag | cagaattggt | tcaagctcgt | attgaacaaa | aaattacaag | tgaaaataac | 960 |
| actaagtggc | tccgtgaggc | gatttctgcc | tttgtgaaaa | ctcagccgca | atggaatggt | 1020 |
| gaaagcgaaa | agccttacga | tgatcacttg | caaaatggtg | ctcttctctt | tgacaatcaa | 1080 |
| actgatttaa | caccagatac | gcaatcgaac | tatcgtttgc | tcaatcgcac | accaactaac | 1140 |
| caaactggtt | ccttggattc | tcgtttcacc | tataacccaa | atgacccact | gggcggctat | 1200 |
| gatttccttt | tagccaacga | tgttgataat | tccaatccag | tcgtgcaagc | ggaacaactc | 1260 |
| aactggctgc | actacctgct | caactttggc | tctatctatg | ccaatgatgc | agatgccaat | 1320 |
| tttgactcaa | tccgtgtaga | tgcggttgat | aatgttgatg | ctgaccttct | gcaaatctct | 1380 |
| agtgattacc | ttaaggcagc | ttacggtatc | gataaaaaca | caaaaatgc | taataaccac | 1440 |
| gtttctatcg | tagaagcatg | gagcgacaac | gatacccctt | atctccatga | tgatggcgac | 1500 |
| aacctcatga | acatggacaa | caagttccgt | tgtccatgc | tttggtcttt | agctaagcca | 1560 |
| accgatgttc | gttctggttt | gaatcctttg | atccacaaca | gtctggttga | ccgtgaagtg | 1620 |
| gatgaccgtg | aagttgaaac | cgttccaagt | tacagctttg | ctcgggctca | tgatagtgaa | 1680 |
| gttcaggata | tcattcgtga | tattattaag | gctgagatta | atccaaattc | atttggttat | 1740 |
| tcattcaccc | aagaagaaat | tgatcaagct | ttcaagattt | acaacgaaga | tctcaagaag | 1800 |
| actgataaaa | aatacactca | ctacaatgtg | ccgcttcctt | ataccttgct | tctgactaac | 1860 |
| aagggttcga | ttcctcgcgt | ctattatgga | gatatgttca | ccgatgatgg | tcaatacatg | 1920 |
| gccaacaaga | ctgtgaacta | cgatgctatc | gaatctctgc | tgaaagcccg | tatgaagtac | 1980 |
| gttgctggtg | gtcaggctat | gcagaattac | caaatcggta | atggcgaaat | cttgacttct | 2040 |
| gtccgttatg | gtaagggtgc | ccttaaacaa | agcgataagg | gtgatgcgac | aactcgtacg | 2100 |

-continued

```
tcaggtgtcg gcgttgttat gggaaaccaa cccaacttta gcttggatgg aaaggttgta    2160
gccctcaaca tgggtgctgc ccacgctaac caagaatacc gtgctcttat ggtatcaact    2220
aaagacggtg ttgcaaccta tgctacagat gctgatgcta gcaaggctgg tctggttaag    2280
cgcacagatg aaaatggtta cctctacttc ttgaacgacg atctcaaggg ggttgctaac    2340
cctcaggttt ctggtttcct tcaagtctgg gtaccagtgg gagcagcaga tgaccaagat    2400
attcgtgtag cagctagcga tacagcaagt accgatggaa aatcactcca tcaagatgct    2460
gccatggact ctcgcgtcat gtttgaaggt ttctctaact tccaatcttt tgcgacaaaa    2520
gaagaagagt ataccaatgt tgtcattgct aacaatgttg ataaatttgt ttcatgggga    2580
atcactgact ttgaaatggc tcctcagtat gtctcatcta ctgacggtca gttccttgat    2640
tctgtcattc aaaatggtta tgcctttacc gaccgttatg acttgggtat gtctaaagca    2700
aacaagtatg gtacagccga ccaattggtt aaggctatca aggctctcca tgctaagggc    2760
ctgaaggtta tggcagactg ggttccagac caaatgtaca ccttccctaa caagaagtg     2820 gtcactgtta ctcggacaga taagtttggc aaaccaatcg caggaagcca aattaatcac    2880
agtctctacg taacagatac aaaagagctct ggtgatgact atcaagctaa atacggcggt    2940
gccttccttg acgaattaaa ggaaaaatat ccagaactct tcaccaagaa gcaaatgtct    3000
actggtcagg cgattgatcc atctgttaag attaaacaat ggtctgctaa gtactttaat    3060
ggaagtaata ttcttggccg gggtgccgat tatgtcctca gcgaccaagt cagcaacaag    3120
tacttcaacg ttgccagcga tacactcttc ttaccaagca gcttactcgg caaggtcgta    3180
gagtctggta ttcgttatga tggtaagggt tatatttata actcaagtgc aactggtgac    3240
caagtcaaag caagcttcat taccgaagca ggcaatctat actacttcgg taaagacggt    3300
tatatggtga ctggcgctca aaccattaat ggtgctaact atttcttcct tgaaaatggt    3360
acggctcttc gcaacactat ttatacagat gctcaaggca atagccatta ctacgcaaat    3420
gacggtaaac gctatgaaaa tggttaccaa caatttggta atgactggcg ttacttcaag    3480
gacggtaaca tggctgttgg cttgacaact gttgatggca atgttcaata ctttgataaa    3540
gatggtgttc aagctaagga taagattatt gtcacccgtg atggtaaggt tcgttacttt    3600
gaccaacata tatggaaatgc tgtaaccaat accttcatcg ctgacaagac tggtcactgg    3660
tactatctag gtaaagatgg tgtcgctgtt accggtgctc aaaccgttgg gaaacaaaaa    3720
ctttactttg aagcaaacgg tcaacaagtt aagggtgact tcgtaacttc tgacgaaggt    3780
aaactttact tctacgatgt cgattcaggt gacatgtgga ctgatacctt cattgaagat    3840
aaggcaggca ttggttcta ccttggtaaa gatggtgcag ctgtgactgg tgctcaaact    3900
attcgtggcc aaaaacttta cttcaaggct aacggccaac aagtcaaggg agatatcgtc    3960
aagggtactg atggtaagat ccgttactac gacgctaaat ctggtgaaca agtcttcaac    4020
aagactgtta aggccgctga tgcaagacc tatgttatcg aaatgatgg tgttgcagtt     4080 gatccaagcg ttgtcaaagg acaaaccttc aaggatgctt caggtgctct tcgtttctat    4140
aacctcaaag gacaactggt aacaggcagc ggttggtatg aaactgcaaa tcacgattgg    4200
gtttatatcc aatctggtaa agccttgact ggggaacaga ccatcaatgg tcaacatctt    4260
tacttcaaga agatggacta tcaagtcaaa ggacaactgg taacaggaac tgatggtaag    4320
gttcgctatt atgatgcaaa ttcaggcgac caagccttca acaagtctgt aacagttaac    4380
ggtaagactt actacttcgg taatgatggc actgctcaaa cagcgggaaa ccctaaggga    4440
```

```
caaaccttca aagatggttc agatatccgc ttttacagca tggaaggcca attagtgact    4500
ggcagtggtt ggtactcaaa cgcacaaggt cagtggcttt atgtcaaaaa tggtaaagtc    4560
ttgacaggcc tgcaaacagt tggtagccaa cgtgtttact ttgacgaaaa tggtattcaa    4620
gctaaaggta aagcagtaag gacttccgac ggtaagatac gctacttcga tgaaaattca    4680
ggtagcatga ttaccaacca atggaaagag gttaacggtc gatattatta cttcggtaat    4740
gatggcgcag ctatctaccg tggctggaac taa                                 4773
```

<210> SEQ ID NO 11
<211> LENGTH: 1590
<212> TYPE: PRT
<213> ORGANISM: Streptococcus sobrinus

<400> SEQUENCE: 11

```
Met Glu Lys Asn Val Arg Phe Lys Met His Lys Val Lys Lys Arg Trp
1               5                   10                  15

Val Thr Leu Ser Val Ala Ser Ala Thr Met Leu Ala Ser Ala Leu Gly
            20                  25                  30

Ala Ser Val Ala Ser Ala Asp Thr Asp Thr Ala Ser Asp Asp Ser Asn
        35                  40                  45

Gln Thr Val Val Thr Gly Asp Gln Thr Thr Asn Asn Gln Ala Thr Asp
    50                  55                  60

Gln Thr Ser Ile Ala Ala Thr Ala Thr Ser Glu Gln Ser Ala Ser Thr
65                  70                  75                  80

Asp Ala Ala Thr Asp Gln Ala Ser Ala Ala Glu Gln Thr Gln Gly Thr
                85                  90                  95

Thr Ala Ser Thr Asp Thr Ala Ala Gln Thr Thr Thr Asn Ala Asn Glu
            100                 105                 110

Ala Lys Trp Val Pro Thr Glu Asn Glu Asn Gln Gly Phe Thr Asp Glu
        115                 120                 125

Met Leu Ala Glu Ala Lys Asn Val Ala Thr Ala Glu Ser Asp Ser Ile
    130                 135                 140

Pro Ser Asp Leu Ala Lys Met Ser Asn Val Lys Gln Val Asp Gly Lys
145                 150                 155                 160

Tyr Tyr Tyr Tyr Asp Gln Asp Gly Asn Val Lys Lys Asn Phe Ala Val
                165                 170                 175

Ser Val Gly Asp Lys Ile Tyr Tyr Phe Asp Glu Thr Gly Ala Tyr Lys
            180                 185                 190

Asp Thr Ser Lys Val Asp Ala Asp Lys Ser Ser Ala Val Ser Gln
        195                 200                 205

Asn Ala Thr Ile Phe Ala Ala Asn Arg Ala Tyr Ser Thr Ser Ala
    210                 215                 220

Lys Asn Phe Glu Ala Val Asp Asn Tyr Leu Thr Ala Asp Ser Trp Tyr
225                 230                 235                 240

Arg Pro Lys Ser Ile Leu Lys Asp Gly Lys Thr Trp Thr Glu Ser Gly
                245                 250                 255

Lys Asp Asp Phe Arg Pro Leu Leu Met Ala Trp Trp Pro Asp Thr Glu
            260                 265                 270

Thr Lys Arg Asn Tyr Val Asn Tyr Met Asn Lys Val Val Gly Ile Asp
        275                 280                 285

Lys Thr Tyr Thr Ala Glu Thr Ser Gln Ala Asp Leu Thr Ala Ala Ala
    290                 295                 300

Glu Leu Val Gln Ala Arg Ile Glu Gln Lys Ile Thr Ser Glu Asn Asn
305                 310                 315                 320
```

```
Thr Lys Trp Leu Arg Glu Ala Ile Ser Ala Phe Val Lys Thr Gln Pro
            325                 330                 335

Gln Trp Asn Gly Glu Ser Glu Lys Pro Tyr Asp Asp His Leu Gln Asn
            340                 345                 350

Gly Ala Leu Leu Phe Asp Asn Gln Thr Asp Leu Thr Pro Asp Thr Gln
            355                 360                 365

Ser Asn Tyr Arg Leu Leu Asn Arg Thr Pro Thr Asn Gln Thr Gly Ser
    370                 375                 380

Leu Asp Ser Arg Phe Thr Tyr Asn Pro Asn Asp Pro Leu Gly Gly Tyr
385                 390                 395                 400

Asp Phe Leu Leu Ala Asn Asp Val Asp Asn Ser Asn Pro Val Val Gln
                405                 410                 415

Ala Glu Gln Leu Asn Trp Leu His Tyr Leu Leu Asn Phe Gly Ser Ile
            420                 425                 430

Tyr Ala Asn Asp Ala Asp Ala Asn Phe Asp Ser Ile Arg Val Asp Ala
            435                 440                 445

Val Asp Asn Val Asp Ala Asp Leu Leu Gln Ile Ser Ser Asp Tyr Leu
    450                 455                 460

Lys Ala Ala Tyr Gly Ile Asp Lys Asn Lys Asn Ala Asn Asn His
465                 470                 475                 480

Val Ser Ile Val Glu Ala Trp Ser Asp Asn Asp Thr Pro Tyr Leu His
                485                 490                 495

Asp Asp Gly Asp Asn Leu Met Asn Met Asp Asn Lys Phe Arg Leu Ser
            500                 505                 510

Met Leu Trp Ser Leu Ala Lys Pro Thr Asp Val Arg Ser Gly Leu Asn
            515                 520                 525

Pro Leu Ile His Asn Ser Leu Val Asp Arg Glu Val Asp Asp Arg Glu
    530                 535                 540

Val Glu Thr Val Pro Ser Tyr Ser Phe Ala Arg Ala His Asp Ser Glu
545                 550                 555                 560

Val Gln Asp Ile Ile Arg Asp Ile Ile Lys Ala Glu Ile Asn Pro Asn
                565                 570                 575

Ser Phe Gly Tyr Ser Phe Thr Gln Glu Glu Ile Asp Gln Ala Phe Lys
            580                 585                 590

Ile Tyr Asn Glu Asp Leu Lys Lys Thr Asp Lys Lys Tyr Thr His Tyr
            595                 600                 605

Asn Val Pro Leu Ser Tyr Thr Leu Leu Leu Thr Asn Lys Gly Ser Ile
    610                 615                 620

Pro Arg Val Tyr Tyr Gly Asp Met Phe Thr Asp Gly Gln Tyr Met
625                 630                 635                 640

Ala Asn Lys Thr Val Asn Tyr Asp Ala Ile Glu Ser Leu Leu Lys Ala
                645                 650                 655

Arg Met Lys Tyr Val Ala Gly Gln Ala Met Gln Asn Tyr Gln Ile
            660                 665                 670

Gly Asn Gly Glu Ile Leu Thr Ser Val Arg Tyr Gly Lys Gly Ala Leu
            675                 680                 685

Lys Gln Ser Asp Lys Gly Asp Ala Thr Thr Arg Thr Ser Gly Val Gly
    690                 695                 700

Val Val Met Gly Asn Gln Pro Asn Phe Ser Leu Asp Gly Lys Val Val
705                 710                 715                 720

Ala Leu Asn Met Gly Ala Ala His Ala Asn Gln Glu Tyr Arg Ala Leu
                725                 730                 735
```

```
Met Val Ser Thr Lys Asp Gly Val Ala Thr Tyr Ala Thr Asp Ala Asp
                740                 745                 750

Ala Ser Lys Ala Gly Leu Val Lys Arg Thr Asp Glu Asn Gly Tyr Leu
            755                 760                 765

Tyr Phe Leu Asn Asp Asp Leu Lys Gly Val Ala Asn Pro Gln Val Ser
770                 775                 780

Gly Phe Leu Gln Val Trp Val Pro Val Gly Ala Ala Asp Asp Gln Asp
785                 790                 795                 800

Ile Arg Val Ala Ala Ser Asp Thr Ala Ser Thr Asp Gly Lys Ser Leu
                805                 810                 815

His Gln Asp Ala Ala Met Asp Ser Arg Val Met Phe Glu Gly Phe Ser
            820                 825                 830

Asn Phe Gln Ser Phe Ala Thr Lys Glu Glu Tyr Thr Asn Val Val
            835                 840                 845

Ile Ala Asn Asn Val Asp Lys Phe Val Ser Trp Gly Ile Thr Asp Phe
            850                 855                 860

Glu Met Ala Pro Gln Tyr Val Ser Ser Thr Asp Gly Gln Phe Leu Asp
865                 870                 875                 880

Ser Val Ile Gln Asn Gly Tyr Ala Phe Thr Asp Arg Tyr Asp Leu Gly
                885                 890                 895

Met Ser Lys Ala Asn Lys Tyr Gly Thr Ala Asp Gln Leu Val Lys Ala
            900                 905                 910

Ile Lys Ala Leu His Ala Lys Gly Leu Lys Val Met Ala Asp Trp Val
            915                 920                 925

Pro Asp Gln Met Tyr Thr Phe Pro Lys Gln Glu Val Val Thr Val Thr
            930                 935                 940

Arg Thr Asp Lys Phe Gly Lys Pro Ile Ala Gly Ser Gln Ile Asn His
945                 950                 955                 960

Ser Leu Tyr Val Thr Asp Thr Lys Ser Ser Gly Asp Tyr Gln Ala
                965                 970                 975

Lys Tyr Gly Gly Ala Phe Leu Asp Glu Leu Lys Glu Lys Tyr Pro Glu
            980                 985                 990

Leu Phe Thr Lys Lys Gln Met Ser Thr Gly Gln Ala Ile Asp Pro Ser
            995                 1000                1005

Val Lys Ile Lys Gln Trp Ser Ala Lys Tyr Phe Asn Gly Ser Asn
    1010                1015                1020

Ile Leu Gly Arg Gly Ala Asp Tyr Val Leu Ser Asp Gln Val Ser
    1025                1030                1035

Asn Lys Tyr Phe Asn Val Ala Ser Asp Thr Leu Phe Leu Pro Ser
    1040                1045                1050

Ser Leu Leu Gly Lys Val Val Glu Ser Gly Ile Arg Tyr Asp Gly
    1055                1060                1065

Lys Gly Tyr Ile Tyr Asn Ser Ser Ala Thr Gly Asp Gln Val Lys
    1070                1075                1080

Ala Ser Phe Ile Thr Glu Ala Gly Asn Leu Tyr Tyr Phe Gly Lys
    1085                1090                1095

Asp Gly Tyr Met Val Thr Gly Ala Gln Thr Ile Asn Gly Ala Asn
    1100                1105                1110

Tyr Phe Phe Leu Glu Asn Gly Thr Ala Leu Arg Asn Thr Ile Tyr
    1115                1120                1125

Thr Asp Ala Gln Gly Asn Ser His Tyr Tyr Ala Asn Asp Gly Lys
    1130                1135                1140

Arg Tyr Glu Asn Gly Tyr Gln Gln Phe Gly Asn Asp Trp Arg Tyr
```

```
              1145                 1150                 1155
Phe Lys Asp Gly Asn Met Ala Val Gly Leu Thr Thr Val Asp Gly
              1160                 1165                 1170
Asn Val Gln Tyr Phe Asp Lys Asp Gly Val Gln Ala Lys Asp Lys
              1175                 1180                 1185
Ile Ile Val Thr Arg Asp Gly Lys Val Arg Tyr Phe Asp Gln His
              1190                 1195                 1200
Asn Gly Asn Ala Val Thr Asn Thr Phe Ile Ala Asp Lys Thr Gly
              1205                 1210                 1215
His Trp Tyr Tyr Leu Gly Lys Asp Gly Val Ala Val Thr Gly Ala
              1220                 1225                 1230
Gln Thr Val Gly Lys Gln Lys Leu Tyr Phe Glu Ala Asn Gly Gln
              1235                 1240                 1245
Gln Val Lys Gly Asp Phe Val Thr Ser Asp Glu Gly Lys Leu Tyr
              1250                 1255                 1260
Phe Tyr Asp Val Asp Ser Gly Asp Met Trp Thr Asp Thr Phe Ile
              1265                 1270                 1275
Glu Asp Lys Ala Gly Asn Trp Phe Tyr Leu Gly Lys Asp Gly Ala
              1280                 1285                 1290
Ala Val Thr Gly Ala Gln Thr Ile Arg Gly Gln Lys Leu Tyr Phe
              1295                 1300                 1305
Lys Ala Asn Gly Gln Gln Val Lys Gly Asp Ile Val Lys Gly Thr
              1310                 1315                 1320
Asp Gly Lys Ile Arg Tyr Tyr Asp Ala Lys Ser Gly Glu Gln Val
              1325                 1330                 1335
Phe Asn Lys Thr Val Lys Ala Ala Asp Gly Lys Thr Tyr Val Ile
              1340                 1345                 1350
Gly Asn Asp Gly Val Ala Val Asp Pro Ser Val Val Lys Gly Gln
              1355                 1360                 1365
Thr Phe Lys Asp Ala Ser Gly Ala Leu Arg Phe Tyr Asn Leu Lys
              1370                 1375                 1380
Gly Gln Leu Val Thr Gly Ser Gly Trp Tyr Glu Thr Ala Asn His
              1385                 1390                 1395
Asp Trp Val Tyr Ile Gln Ser Gly Lys Ala Leu Thr Gly Glu Gln
              1400                 1405                 1410
Thr Ile Asn Gly Gln His Leu Tyr Phe Lys Lys Asp Gly His Gln
              1415                 1420                 1425
Val Lys Gly Gln Leu Val Thr Gly Thr Asp Gly Lys Val Arg Tyr
              1430                 1435                 1440
Tyr Asp Ala Asn Ser Gly Asp Gln Ala Phe Asn Lys Ser Val Thr
              1445                 1450                 1455
Val Asn Gly Lys Thr Tyr Tyr Phe Gly Asn Asp Gly Thr Ala Gln
              1460                 1465                 1470
Thr Ala Gly Asn Pro Lys Gly Gln Thr Phe Lys Asp Gly Ser Asp
              1475                 1480                 1485
Ile Arg Phe Tyr Ser Met Glu Gly Gln Leu Val Thr Gly Ser Gly
              1490                 1495                 1500
Trp Tyr Ser Asn Ala Gln Gly Gln Trp Leu Tyr Val Lys Asn Gly
              1505                 1510                 1515
Lys Val Leu Thr Gly Leu Gln Thr Val Gly Ser Gln Arg Val Tyr
              1520                 1525                 1530
Phe Asp Glu Asn Gly Ile Gln Ala Lys Gly Lys Ala Val Arg Thr
              1535                 1540                 1545
```

Ser Asp Gly Lys Ile Arg Tyr Phe Asp Glu Asn Ser Gly Ser Met
    1550                1555                1560

Ile Thr Asn Gln Trp Lys Glu Val Asn Gly Arg Tyr Tyr Tyr Phe
1565                1570                1575

Gly Asn Asp Gly Ala Ala Ile Tyr Arg Gly Trp Asn
    1580                1585                1590

<210> SEQ ID NO 12
<211> LENGTH: 1552
<212> TYPE: PRT
<213> ORGANISM: Streptococcus sobrinus

<400> SEQUENCE: 12

Asp Thr Asp Thr Ala Ser Asp Asp Ser Asn Gln Thr Val Val Thr Gly
1               5                   10                  15

Asp Gln Thr Thr Asn Asn Gln Ala Thr Asp Gln Thr Ser Ile Ala Ala
                20                  25                  30

Thr Ala Thr Ser Glu Gln Ser Ala Ser Thr Asp Ala Ala Thr Asp Gln
            35                  40                  45

Ala Ser Ala Ala Glu Gln Thr Gln Gly Thr Thr Ala Ser Thr Asp Thr
50                  55                  60

Ala Ala Gln Thr Thr Thr Asn Ala Asn Glu Ala Lys Trp Val Pro Thr
65                  70                  75                  80

Glu Asn Glu Asn Gln Gly Phe Thr Asp Glu Met Leu Ala Glu Ala Lys
                85                  90                  95

Asn Val Ala Thr Ala Glu Ser Asp Ser Ile Pro Ser Asp Leu Ala Lys
            100                 105                 110

Met Ser Asn Val Lys Gln Val Asp Gly Lys Tyr Tyr Tyr Tyr Asp Gln
        115                 120                 125

Asp Gly Asn Val Lys Lys Asn Phe Ala Val Ser Val Gly Asp Lys Ile
    130                 135                 140

Tyr Tyr Phe Asp Glu Thr Gly Ala Tyr Lys Asp Thr Ser Lys Val Asp
145                 150                 155                 160

Ala Asp Lys Ser Ser Ser Ala Val Ser Gln Asn Ala Thr Ile Phe Ala
                165                 170                 175

Ala Asn Asn Arg Ala Tyr Ser Thr Ser Ala Lys Asn Phe Glu Ala Val
            180                 185                 190

Asp Asn Tyr Leu Thr Ala Asp Ser Trp Tyr Arg Pro Lys Ser Ile Leu
        195                 200                 205

Lys Asp Gly Lys Thr Trp Thr Glu Ser Gly Lys Asp Asp Phe Arg Pro
    210                 215                 220

Leu Leu Met Ala Trp Trp Pro Asp Thr Glu Thr Lys Arg Asn Tyr Val
225                 230                 235                 240

Asn Tyr Met Asn Lys Val Val Gly Ile Asp Lys Thr Tyr Thr Ala Glu
                245                 250                 255

Thr Ser Gln Ala Asp Leu Thr Ala Ala Ala Glu Leu Val Gln Ala Arg
            260                 265                 270

Ile Glu Gln Lys Ile Thr Ser Glu Asn Asn Thr Lys Trp Leu Arg Glu
        275                 280                 285

Ala Ile Ser Ala Phe Val Lys Thr Gln Pro Gln Trp Asn Gly Glu Ser
    290                 295                 300

Glu Lys Pro Tyr Asp Asp His Leu Gln Asn Gly Ala Leu Leu Phe Asp
305                 310                 315                 320

Asn Gln Thr Asp Leu Thr Pro Asp Thr Gln Ser Asn Tyr Arg Leu Leu

```
                    325                 330                 335
Asn Arg Thr Pro Thr Asn Gln Thr Gly Ser Leu Asp Ser Arg Phe Thr
                340                 345                 350
Tyr Asn Pro Asn Asp Pro Leu Gly Gly Tyr Asp Phe Leu Leu Ala Asn
                355                 360                 365
Asp Val Asp Asn Ser Asn Pro Val Val Gln Ala Glu Gln Leu Asn Trp
            370                 375                 380
Leu His Tyr Leu Leu Asn Phe Gly Ser Ile Tyr Ala Asn Asp Ala Asp
385                 390                 395                 400
Ala Asn Phe Asp Ser Ile Arg Val Asp Ala Val Asp Asn Val Asp Ala
                405                 410                 415
Asp Leu Leu Gln Ile Ser Ser Asp Tyr Leu Lys Ala Ala Tyr Gly Ile
                420                 425                 430
Asp Lys Asn Asn Lys Asn Ala Asn Asn His Val Ser Ile Val Glu Ala
                435                 440                 445
Trp Ser Asp Asn Asp Thr Pro Tyr Leu His Asp Gly Asp Asn Leu
450                 455                 460
Met Asn Met Asp Asn Lys Phe Arg Leu Ser Met Leu Trp Ser Leu Ala
465                 470                 475                 480
Lys Pro Thr Asp Val Arg Ser Gly Leu Asn Pro Leu Ile His Asn Ser
                485                 490                 495
Leu Val Asp Arg Glu Val Asp Asp Arg Glu Val Glu Thr Val Pro Ser
                500                 505                 510
Tyr Ser Phe Ala Arg Ala His Asp Ser Glu Val Gln Asp Ile Ile Arg
                515                 520                 525
Asp Ile Ile Lys Ala Glu Ile Asn Pro Asn Ser Phe Gly Tyr Ser Phe
            530                 535                 540
Thr Gln Glu Glu Ile Asp Gln Ala Phe Lys Ile Tyr Asn Glu Asp Leu
545                 550                 555                 560
Lys Lys Thr Asp Lys Lys Tyr Thr His Tyr Asn Val Pro Leu Ser Tyr
                565                 570                 575
Thr Leu Leu Leu Thr Asn Lys Gly Ser Ile Pro Arg Val Tyr Tyr Gly
                580                 585                 590
Asp Met Phe Thr Asp Asp Gly Gln Tyr Met Ala Asn Lys Thr Val Asn
                595                 600                 605
Tyr Asp Ala Ile Glu Ser Leu Leu Lys Ala Arg Met Lys Tyr Val Ala
            610                 615                 620
Gly Gly Gln Ala Met Gln Asn Tyr Gln Ile Gly Asn Gly Glu Ile Leu
625                 630                 635                 640
Thr Ser Val Arg Tyr Gly Lys Gly Ala Leu Lys Gln Ser Asp Lys Gly
                645                 650                 655
Asp Ala Thr Thr Arg Thr Ser Gly Val Gly Val Met Gly Asn Gln
                660                 665                 670
Pro Asn Phe Ser Leu Asp Gly Lys Val Val Ala Leu Asn Met Gly Ala
                675                 680                 685
Ala His Ala Asn Gln Glu Tyr Arg Ala Leu Met Val Ser Thr Lys Asp
            690                 695                 700
Gly Val Ala Thr Tyr Ala Thr Asp Ala Asp Ala Ser Lys Ala Gly Leu
705                 710                 715                 720
Val Lys Arg Thr Asp Glu Asn Gly Tyr Leu Tyr Phe Leu Asn Asp Asp
                725                 730                 735
Leu Lys Gly Val Ala Asn Pro Gln Val Ser Gly Phe Leu Gln Val Trp
            740                 745                 750
```

```
Val Pro Val Gly Ala Ala Asp Asp Gln Asp Ile Arg Val Ala Ala Ser
        755                 760                 765

Asp Thr Ala Ser Thr Asp Gly Lys Ser Leu His Gln Asp Ala Ala Met
770                 775                 780

Asp Ser Arg Val Met Phe Glu Gly Phe Ser Asn Phe Gln Ser Phe Ala
785                 790                 795                 800

Thr Lys Glu Glu Glu Tyr Thr Asn Val Val Ile Ala Asn Asn Val Asp
                805                 810                 815

Lys Phe Val Ser Trp Gly Ile Thr Asp Phe Glu Met Ala Pro Gln Tyr
                820                 825                 830

Val Ser Ser Thr Asp Gly Gln Phe Leu Asp Ser Val Ile Gln Asn Gly
                835                 840                 845

Tyr Ala Phe Thr Asp Arg Tyr Asp Leu Gly Met Ser Lys Ala Asn Lys
850                 855                 860

Tyr Gly Thr Ala Asp Gln Leu Val Lys Ala Ile Lys Ala Leu His Ala
865                 870                 875                 880

Lys Gly Leu Lys Val Met Ala Asp Trp Val Pro Asp Gln Met Tyr Thr
                885                 890                 895

Phe Pro Lys Gln Glu Val Val Thr Val Thr Arg Thr Asp Lys Phe Gly
                900                 905                 910

Lys Pro Ile Ala Gly Ser Gln Ile Asn His Ser Leu Tyr Val Thr Asp
                915                 920                 925

Thr Lys Ser Ser Gly Asp Asp Tyr Gln Ala Lys Tyr Gly Gly Ala Phe
930                 935                 940

Leu Asp Glu Leu Lys Glu Lys Tyr Pro Glu Leu Phe Thr Lys Lys Gln
945                 950                 955                 960

Met Ser Thr Gly Gln Ala Ile Asp Pro Ser Val Lys Ile Lys Gln Trp
                965                 970                 975

Ser Ala Lys Tyr Phe Asn Gly Ser Asn Ile Leu Gly Arg Gly Ala Asp
                980                 985                 990

Tyr Val Leu Ser Asp Gln Val Ser Asn Lys Tyr Phe Asn Val Ala Ser
                995                 1000                1005

Asp Thr Leu Phe Leu Pro Ser Ser Leu Leu Gly Lys Val Val Glu
        1010                1015                1020

Ser Gly Ile Arg Tyr Asp Lys Gly Tyr Ile Tyr Asn Ser Ser
        1025                1030                1035

Ala Thr Gly Asp Gln Val Lys Ala Ser Phe Ile Thr Glu Ala Gly
        1040                1045                1050

Asn Leu Tyr Tyr Phe Gly Lys Asp Gly Tyr Met Val Thr Gly Ala
        1055                1060                1065

Gln Thr Ile Asn Gly Ala Asn Tyr Phe Phe Leu Glu Asn Gly Thr
        1070                1075                1080

Ala Leu Arg Asn Thr Ile Tyr Thr Asp Ala Gln Gly Asn Ser His
        1085                1090                1095

Tyr Tyr Ala Asn Asp Gly Lys Arg Tyr Glu Asn Gly Tyr Gln Gln
        1100                1105                1110

Phe Gly Asn Asp Trp Arg Tyr Phe Lys Asp Gly Asn Met Ala Val
        1115                1120                1125

Gly Leu Thr Thr Val Asp Gly Asn Val Gln Tyr Phe Asp Lys Asp
        1130                1135                1140

Gly Val Gln Ala Lys Asp Lys Ile Ile Val Thr Arg Asp Gly Lys
        1145                1150                1155
```

```
Val Arg Tyr Phe Asp Gln His Asn Gly Asn Ala Val Thr Asn Thr
1160                1165                1170

Phe Ile Ala Asp Lys Thr Gly His Trp Tyr Tyr Leu Gly Lys Asp
1175                1180                1185

Gly Val Ala Val Thr Gly Ala Gln Thr Val Gly Lys Gln Lys Leu
1190                1195                1200

Tyr Phe Glu Ala Asn Gly Gln Gln Val Lys Gly Asp Phe Val Thr
1205                1210                1215

Ser Asp Glu Gly Lys Leu Tyr Phe Tyr Asp Val Asp Ser Gly Asp
1220                1225                1230

Met Trp Thr Asp Thr Phe Ile Glu Asp Lys Ala Gly Asn Trp Phe
1235                1240                1245

Tyr Leu Gly Lys Asp Gly Ala Ala Val Thr Gly Ala Gln Thr Ile
1250                1255                1260

Arg Gly Gln Lys Leu Tyr Phe Lys Ala Asn Gly Gln Gln Val Lys
1265                1270                1275

Gly Asp Ile Val Lys Gly Thr Asp Gly Lys Ile Arg Tyr Tyr Asp
1280                1285                1290

Ala Lys Ser Gly Glu Gln Val Phe Asn Lys Thr Val Lys Ala Ala
1295                1300                1305

Asp Gly Lys Thr Tyr Val Ile Gly Asn Asp Gly Val Ala Val Asp
1310                1315                1320

Pro Ser Val Val Lys Gly Gln Thr Phe Lys Asp Ala Ser Gly Ala
1325                1330                1335

Leu Arg Phe Tyr Asn Leu Lys Gly Gln Leu Val Thr Gly Ser Gly
1340                1345                1350

Trp Tyr Glu Thr Ala Asn His Asp Trp Val Tyr Ile Gln Ser Gly
1355                1360                1365

Lys Ala Leu Thr Gly Glu Gln Thr Ile Asn Gly Gln His Leu Tyr
1370                1375                1380

Phe Lys Lys Asp Gly His Gln Val Lys Gly Gln Leu Val Thr Gly
1385                1390                1395

Thr Asp Gly Lys Val Arg Tyr Tyr Asp Ala Asn Ser Gly Asp Gln
1400                1405                1410

Ala Phe Asn Lys Ser Val Thr Val Asn Gly Lys Thr Tyr Tyr Phe
1415                1420                1425

Gly Asn Asp Gly Thr Ala Gln Thr Ala Gly Asn Pro Lys Gly Gln
1430                1435                1440

Thr Phe Lys Asp Gly Ser Asp Ile Arg Phe Tyr Ser Met Glu Gly
1445                1450                1455

Gln Leu Val Thr Gly Ser Gly Trp Tyr Ser Asn Ala Gln Gly Gln
1460                1465                1470

Trp Leu Tyr Val Lys Asn Gly Lys Val Leu Thr Gly Leu Gln Thr
1475                1480                1485

Val Gly Ser Gln Arg Val Tyr Phe Asp Glu Asn Gly Ile Gln Ala
1490                1495                1500

Lys Gly Lys Ala Val Arg Thr Ser Asp Gly Lys Ile Arg Tyr Phe
1505                1510                1515

Asp Glu Asn Ser Gly Ser Met Ile Thr Asn Gln Trp Lys Glu Val
1520                1525                1530

Asn Gly Arg Tyr Tyr Tyr Phe Gly Asn Asp Gly Ala Ala Ile Tyr
1535                1540                1545

Arg Gly Trp Asn
```

<210> SEQ ID NO 13
<211> LENGTH: 4452
<212> TYPE: DNA
<213> ORGANISM: Leuconostoc pseudomesenteroides

<400> SEQUENCE: 13

```
atgggagaga aagtcgtggc gagaaagaag ctttataagg cgaaaaaaag ttgggtggta      60
gctggtttga ctactgcctt tttgatggtg aatcaagcca gtgtaagcgc tgatcaaaat     120
gtaaatgata catcggtcac aacaacaacg caggatgtca caacagatca ggacactggt     180
attgacgcat ctgtaacgac gacagttagt ccaaatttgg atgatactca agttgataac     240
accaatattc agacgtcaac agatcaaaaa gatgattcaa aaggcaccac gcaaacagtt     300
gaaacggacg ttacaacgaa tagtcaatca acagacacaa cagcagtgac agctcaaacg     360
aatcaaacag aaacaataca aaatagtgat gcgacaactg aaacaggatt agtgacagtt     420
aataatcaag tcagatacgt taatcctgat ggcacagttt tgaaaggcgc atacaaaaca     480
attaatggta atacctatta ttttgatgat aatagtggtg acgcactgat aggaatacat     540
aaaattggag aatcaattaa gggatttggt cttactggtg tccaagtcaa aggagattac     600
ttaacggcag tcaacggtga caaatattac tttgattctg acggtaatac ggtgtctggc     660
gtgcagcaaa ttaatggcaa gacctattat tttgacagca ctggtaaatt aatgaagggc     720
tacacagcag tcttgaatgg tgtcgtaact ttcttcaata gcacaactgg tgaagcagat     780
aatactgatg cctcaaccat taaaactggc gttacaatcg acaactcgga ttacacagct     840
cataatgctg cctatgataa tacagccgcc agctttgata atatcaatgg ctatctgacg     900
gcagaaagtt ggtacagacc taagaaaata ttggaaaatg gtgagtcatg gcggccatct     960
actgctgagg ataaacgtcc cattttaatc acttggcaac cggatattgt gaccgaggtc    1020
aattatctca acatgatgtc tgcaaatggt ttgctctcga ttaacgcacc atttacaact    1080
gctagtgacc ttgccattat gaatgatgct gtcagagctg ttcaaaagaa tattgaaata    1140
cggattagcc aagaaaaatc aactgattgg ttaaaagcgt tgatgactca gtttattaat    1200
acacaaccgc agtggaatga ggtgagtgaa tcaccaagca atgatcacct acaaggcggt    1260
gcattaacgt atgtcaatag tccattgacg ccagatgcca attctaattt tcgtttgctt    1320
aatcggaccc cgactaatca atctggcaca acgcgttatg atactgacaa atctgaaggt    1380
ggttttgaat tattattagc taatgatgtt gataattcaa acccagtagt tcaagctgag    1440
caacttaact ggttgtacta tttaatgaat tttggctcaa ttacagctaa tgatccaacg    1500
gctaattttg atggtattag agttgatgct gttgataacg tagacgctga cttgttgcaa    1560
attgcatcgg attactttaa attagcgtat ggcactagtt tatctgatac aaatgctaac    1620
caacatttat caattttgga agattggtct gctaatgatg cggaatacat gtcaaaaacg    1680
ggtagtaatc aattgacaat ggacacgtat acgcagcaac aattactctt ttcattgaca    1740
aaacaagttg gtaatcgtgc tgacatgcga cgcttcctag aatactttat gattaatcgt    1800
gccaacgatt caaccgaaaa tattgcgaca ccaaattact catttgttcg tgcacatgac    1860
agtgaagttc aaacggtcat tgctacgata attaaagatt tacatcctga tgttgtgaat    1920
agtcttgcgc caactcaagc acaattagaa gaggcatttg ccgtgtataa cgctgatatg    1980
aatcgggtgg ataaacaata tacccaatac aaatatgcca agtgcttatgc catgcttttg    2040
accaataaag atacgattcc acgtgtatat tatggtgatt tatacacaga tgatggtgag    2100
```

```
tatatgggta cgcaaacacc ctattatgat gctatcgtta atctattgca gtctcgcgtt     2160
aaatatgttg caggtggaca atccatggcg gttgatcaac atgatatttt aacaagtgtg     2220
cgttatggca aaaatttggc tgacgctaat gcgacatcag atgatttaac cagtattaac     2280
tcaggcatag gtgttattgt ttctaataat cccaatcttt cgttggcgtc tggtgaaacc     2340
gtcgtgctcc atatgggcat tgcacacgct aatcaagttt atcgtgagat acttgagaca     2400
accgacaacg gtattgcaaa ataccgat attttaaaa caacagacag taatggtgac     2460
ttgattttca cagcttctga aattcatggg tatagtaatg ttcaagtatc aggcttttta     2520
tcagtttggg cgcctaaaga tgctacggat aatcaagatg tacgtactgc tgctagtgaa     2580
tcgacttcta gtgatggcaa tacgcttcat tcaaatgctg ccttagattc aacataatt     2640 tatgaaggct tttcaaactt tcaatccaca cctcagtcag aaagtgaatt tgcaaaggtc     2700
aaaatagctg ctaatgttaa tctgttcaaa tcttggggtg tcaccagttt tcaaatggca     2760
cctcaatatc gctcgagcac cgatacaagc ttttggatt ccattattca aaatggttat     2820
gccttcactg accgttacga tttgggattt gaaacaccaa cgaagtatgg gacggaccag     2880
caattgcgtg atgcaattaa agcattgcat gctaatggta tacaagcaat ggctgacttt     2940
gtgccagacc agatttataa tttgcctcaa acagaactgg tttctgtatc acgcaccgat     3000
agtcttggta atcagtcagc caattcaaat gcagccaatg tattgtatgt atctcataca     3060
gttggtggtg gtgaatatca aagcaagtat gggggcgaat ttttagcgct tattaagtct     3120
aaatatccaa gcttgtttaa aacaattcag gtttcgacag gactaccaat tgatgattca     3180
actaagatta aagagtggtc ggcaaaatac tttaatggtt caaatattca aggacgtggt     3240
tttggatatg tgctatctga tggtggcacg cagaattact ttaaagtgat ttcgaacagt     3300
acagatgatg actttttgcc taatcagctg actggacaac ccacaatgac aggctttgaa     3360
caaacaagta agggtattgt atattactct aagagtggta ttcaggctaa aaatcaattc     3420
gtcaaagatg atgtttctgg taattactac tatttcaata agaatggtct gatgacaatt     3480
ggcagtaaga cgatcaatgg taaaaactat atgttcttgc caacggcgt agagttacga     3540 ggatcctttt tacaaacggc ggatgggacc gtcaattact atgcgactaa tggggcacag     3600
gttaaggacg cctatgtgac tgacacagaa ggtaatagtt attactttga tggtgatggg     3660
gaaatggtaa cgggtgctta tacagttgat ggacatgcgc aatattttga tgtgaatggt     3720
gttcaaacca aggggctat tattacactt gacggtgtgc aacgctatta tcaagctggg     3780
aacggtaatt tggcaacgaa tcaatatgtc agttacaaca acagctggta ctatgccaac     3840
gccaagggcg agttagtgac tggtgttcaa agtattaatg gtaacgttca atattttgcc     3900
agcaatgggc aacaaattaa aggtcaaatt gttgtgactg gtaatcagaa aagttattac     3960
gatgcaaaca ctggaaatct tatcagaaat gatttttga caccggatca aggtaaaact     4020
tggtattatg ccgatcaaga tggtaatctt gtggtaggtg tacggaatat taatggacac     4080
aatcaatatt ttgatgataa tgggatacaa atcaaagacc aaatcatatc aaatgatggg     4140
caacaatatt attatcaagg tggtaatggt gatttagtca caaatcgata tatcagttac     4200
aatgatagtt ggtattacgc cgacgcaaca ggtgttcttg taacaggtca acaaattatc     4260
aacggtgaaa cgcaatactt taggacagat ggtcgccaag tcaagggcca aattattgct     4320
gatggtgata acagcattta ttacgacgca tattcaggca atttggttaa aaataatttt     4380
gtcacagtcg accaaggtaa aacttggtat tatgctgatc aagatgggaa cctctctttg     4440
```
gttgcccaat aa                                                            4452

<210> SEQ ID NO 14
<211> LENGTH: 1483
<212> TYPE: PRT
<213> ORGANISM: Leuconostoc pseudomesenteroides

<400> SEQUENCE: 14

Met Gly Glu Lys Val Val Ala Arg Lys Lys Leu Tyr Lys Ala Lys Lys
1               5                   10                  15

Ser Trp Val Val Ala Gly Leu Thr Thr Ala Phe Leu Met Val Asn Gln
            20                  25                  30

Ala Ser Val Ser Ala Asp Gln Asn Val Asn Asp Thr Ser Val Thr Thr
        35                  40                  45

Thr Thr Gln Asp Val Thr Thr Asp Gln Asp Thr Gly Ile Asp Ala Ser
    50                  55                  60

Val Thr Thr Thr Val Ser Pro Asn Leu Asp Asp Thr Gln Val Asp Asn
65                  70                  75                  80

Thr Asn Ile Gln Thr Ser Thr Asp Gln Lys Asp Ser Lys Gly Thr
            85                  90                  95

Thr Gln Thr Val Glu Thr Asp Val Thr Thr Asn Ser Gln Ser Thr Asp
            100                 105                 110

Thr Thr Ala Val Thr Ala Gln Thr Asn Gln Thr Glu Thr Ile Gln Asn
        115                 120                 125

Ser Asp Ala Thr Thr Glu Thr Gly Leu Val Thr Val Asn Asn Gln Val
130                 135                 140

Arg Tyr Val Asn Pro Asp Gly Thr Val Leu Lys Gly Ala Tyr Lys Thr
145                 150                 155                 160

Ile Asn Gly Asn Thr Tyr Tyr Phe Asp Asp Asn Ser Gly Asp Ala Leu
            165                 170                 175

Ile Gly Ile His Lys Ile Gly Glu Ser Ile Lys Gly Phe Gly Leu Thr
        180                 185                 190

Gly Val Gln Val Lys Gly Asp Tyr Leu Thr Ala Val Asn Gly Asp Lys
    195                 200                 205

Tyr Tyr Phe Asp Ser Asp Gly Asn Thr Val Ser Gly Val Gln Gln Ile
210                 215                 220

Asn Gly Lys Thr Tyr Tyr Phe Asp Ser Thr Gly Lys Leu Met Lys Gly
225                 230                 235                 240

Tyr Thr Ala Val Leu Asn Gly Val Val Thr Phe Phe Asn Ser Thr Thr
            245                 250                 255

Gly Glu Ala Asp Asn Thr Asp Ala Ser Thr Ile Lys Thr Gly Val Thr
        260                 265                 270

Ile Asp Asn Ser Asp Tyr Thr Ala His Asn Ala Ala Tyr Asp Asn Thr
    275                 280                 285

Ala Ala Ser Phe Asp Asn Ile Asn Gly Tyr Leu Thr Ala Glu Ser Trp
290                 295                 300

Tyr Arg Pro Lys Glu Ile Leu Glu Asn Gly Glu Ser Trp Arg Pro Ser
305                 310                 315                 320

Thr Ala Glu Asp Lys Arg Pro Ile Leu Ile Thr Trp Gln Pro Asp Ile
            325                 330                 335

Val Thr Glu Val Asn Tyr Leu Asn Met Met Ser Ala Asn Gly Leu Leu
        340                 345                 350

Ser Ile Asn Ala Pro Phe Thr Thr Ala Ser Asp Leu Ala Ile Met Asn
    355                 360                 365

```
Asp Ala Val Arg Ala Val Gln Lys Asn Ile Glu Ile Arg Ile Ser Gln
    370                 375                 380

Glu Lys Ser Thr Asp Trp Leu Lys Ala Leu Met Thr Gln Phe Ile Asn
385                 390                 395                 400

Thr Gln Pro Gln Trp Asn Glu Val Ser Glu Ser Pro Ser Asn Asp His
                405                 410                 415

Leu Gln Gly Gly Ala Leu Thr Tyr Val Asn Ser Pro Leu Thr Pro Asp
                420                 425                 430

Ala Asn Ser Asn Phe Arg Leu Leu Asn Arg Thr Pro Thr Asn Gln Ser
            435                 440                 445

Gly Thr Thr Arg Tyr Asp Thr Asp Lys Ser Glu Gly Gly Phe Glu Leu
    450                 455                 460

Leu Leu Ala Asn Asp Val Asp Asn Ser Asn Pro Val Val Gln Ala Glu
465                 470                 475                 480

Gln Leu Asn Trp Leu Tyr Tyr Leu Met Asn Phe Gly Ser Ile Thr Ala
                485                 490                 495

Asn Asp Pro Thr Ala Asn Phe Asp Gly Ile Arg Val Asp Ala Val Asp
                500                 505                 510

Asn Val Asp Ala Asp Leu Leu Gln Ile Ala Ser Asp Tyr Phe Lys Leu
            515                 520                 525

Ala Tyr Gly Thr Ser Leu Ser Asp Thr Asn Ala Asn Gln His Leu Ser
    530                 535                 540

Ile Leu Glu Asp Trp Ser Ala Asn Asp Ala Glu Tyr Met Ser Lys Thr
545                 550                 555                 560

Gly Ser Asn Gln Leu Thr Met Asp Thr Tyr Thr Gln Gln Leu Leu
                565                 570                 575

Phe Ser Leu Thr Lys Gln Val Gly Asn Arg Ala Asp Met Arg Arg Phe
                580                 585                 590

Leu Glu Tyr Phe Met Ile Asn Arg Ala Asn Asp Ser Thr Glu Asn Ile
            595                 600                 605

Ala Thr Pro Asn Tyr Ser Phe Val Arg Ala His Asp Ser Glu Val Gln
    610                 615                 620

Thr Val Ile Ala Thr Ile Ile Lys Asp Leu His Pro Asp Val Val Asn
625                 630                 635                 640

Ser Leu Ala Pro Thr Gln Ala Gln Leu Glu Glu Ala Phe Ala Val Tyr
                645                 650                 655

Asn Ala Asp Met Asn Arg Val Asp Lys Gln Tyr Thr Gln Tyr Asn Met
            660                 665                 670

Pro Ser Ala Tyr Ala Met Leu Leu Thr Asn Lys Asp Thr Ile Pro Arg
    675                 680                 685

Val Tyr Tyr Gly Asp Leu Tyr Thr Asp Asp Gly Glu Tyr Met Gly Thr
690                 695                 700

Gln Thr Pro Tyr Tyr Asp Ala Ile Val Asn Leu Leu Gln Ser Arg Val
705                 710                 715                 720

Lys Tyr Val Ala Gly Gly Gln Ser Met Ala Val Asp Gln His Asp Ile
                725                 730                 735

Leu Thr Ser Val Arg Tyr Gly Lys Asn Leu Ala Asp Ala Asn Ala Thr
            740                 745                 750

Ser Asp Asp Leu Thr Ser Ile Asn Ser Gly Ile Gly Val Ile Val Ser
    755                 760                 765

Asn Asn Pro Asn Leu Ser Leu Ala Ser Gly Glu Thr Val Val Leu His
770                 775                 780

Met Gly Ile Ala His Ala Asn Gln Val Tyr Arg Glu Ile Leu Glu Thr
```

```
            785                 790                 795                 800
        Thr Asp Asn Gly Ile Ala Asn Thr Asp Ile Phe Lys Thr Thr Asp
                        805                 810                 815

Ser Asn Gly Asp Leu Ile Phe Thr Ala Ser Glu Ile His Gly Tyr Ser
                        820                 825                 830

Asn Val Gln Val Ser Gly Phe Leu Ser Val Trp Ala Pro Lys Asp Ala
                        835                 840                 845

Thr Asp Asn Gln Asp Val Arg Thr Ala Ala Ser Glu Ser Thr Ser Ser
                850                 855                 860

Asp Gly Asn Thr Leu His Ser Asn Ala Ala Leu Asp Ser Asn Ile Ile
                865                 870                 875                 880

Tyr Glu Gly Phe Ser Asn Phe Gln Ser Thr Pro Gln Ser Glu Ser Glu
                        885                 890                 895

Phe Ala Lys Val Lys Ile Ala Ala Asn Val Asn Leu Phe Lys Ser Trp
                        900                 905                 910

Gly Val Thr Ser Phe Gln Met Ala Pro Gln Tyr Arg Ser Ser Thr Asp
                        915                 920                 925

Thr Ser Phe Leu Asp Ser Ile Ile Gln Asn Gly Tyr Ala Phe Thr Asp
                        930                 935                 940

Arg Tyr Asp Leu Gly Phe Glu Thr Pro Thr Lys Tyr Gly Thr Asp Gln
        945                 950                 955                 960

Gln Leu Arg Asp Ala Ile Lys Ala Leu His Ala Asn Gly Ile Gln Ala
                        965                 970                 975

Met Ala Asp Phe Val Pro Asp Gln Ile Tyr Asn Leu Pro Gln Thr Glu
                        980                 985                 990

Leu Val Ser Val Ser Arg Thr Asp  Ser Leu Gly Asn Gln  Ser Ala Asn
                        995                 1000                1005

Ser Asn  Ala Ala Asn Val Leu  Tyr Val Ser His Thr  Val Gly Gly
                        1010                1015                1020

Gly Glu  Tyr Gln Ser Lys Tyr  Gly Gly Glu Phe Leu  Ala Leu Ile
                        1025                1030                1035

Lys Ser  Lys Tyr Pro Ser Leu  Phe Lys Thr Ile Gln  Val Ser Thr
                        1040                1045                1050

Gly Leu  Pro Ile Asp Asp Ser  Thr Lys Ile Lys Glu  Trp Ser Ala
                        1055                1060                1065

Lys Tyr  Phe Asn Gly Ser Asn  Ile Gln Gly Arg Gly  Phe Gly Tyr
                        1070                1075                1080

Val Leu  Ser Asp Gly Gly Thr  Gln Asn Tyr Phe Lys  Val Ile Ser
                        1085                1090                1095

Asn Ser  Thr Asp Asp Asp Phe  Leu Pro Asn Gln Leu  Thr Gly Gln
                        1100                1105                1110

Pro Thr  Met Thr Gly Phe Glu  Gln Thr Ser Lys Gly  Ile Val Tyr
                        1115                1120                1125

Tyr Ser  Lys Ser Gly Ile Gln  Ala Lys Asn Gln Phe  Val Lys Asp
                        1130                1135                1140

Asp Val  Ser Gly Asn Tyr Tyr  Tyr Phe Asn Lys Asn  Gly Leu Met
                        1145                1150                1155

Thr Ile  Gly Ser Lys Thr Ile  Asn Gly Lys Asn Tyr  Met Phe Leu
                        1160                1165                1170

Pro Asn  Gly Val Glu Leu Arg  Gly Ser Phe Leu Gln  Thr Ala Asp
                        1175                1180                1185

Gly Thr  Val Asn Tyr Tyr Ala  Thr Asn Gly Ala Gln  Val Lys Asp
                        1190                1195                1200
```

```
Ala Tyr Val Thr Asp Thr Glu Gly Asn Ser Tyr Tyr Phe Asp Gly
    1205                1210                1215

Asp Gly Glu Met Val Thr Gly Ala Tyr Thr Val Asp Gly His Ala
    1220                1225                1230

Gln Tyr Phe Asp Val Asn Gly Val Gln Thr Lys Gly Ala Ile Ile
    1235                1240                1245

Thr Leu Asp Gly Val Gln Arg Tyr Tyr Gln Ala Gly Asn Gly Asn
    1250                1255                1260

Leu Ala Thr Asn Gln Tyr Val Ser Tyr Asn Asn Ser Trp Tyr Tyr
    1265                1270                1275

Ala Asn Ala Lys Gly Glu Leu Val Thr Gly Val Gln Ser Ile Asn
    1280                1285                1290

Gly Asn Val Gln Tyr Phe Ala Ser Asn Gly Gln Gln Ile Lys Gly
    1295                1300                1305

Gln Ile Val Val Thr Gly Asn Gln Lys Ser Tyr Tyr Asp Ala Asn
    1310                1315                1320

Thr Gly Asn Leu Ile Arg Asn Asp Phe Leu Thr Pro Asp Gln Gly
    1325                1330                1335

Lys Thr Trp Tyr Tyr Ala Asp Gln Asp Gly Asn Leu Val Val Gly
    1340                1345                1350

Val Arg Asn Ile Asn Gly His Asn Gln Tyr Phe Asp Asp Asn Gly
    1355                1360                1365

Ile Gln Ile Lys Asp Gln Ile Ile Ser Asn Asp Gly Gln Gln Tyr
    1370                1375                1380

Tyr Tyr Gln Gly Gly Asn Gly Asp Leu Val Thr Asn Arg Tyr Ile
    1385                1390                1395

Ser Tyr Asn Asp Ser Trp Tyr Tyr Ala Asp Ala Thr Gly Val Leu
    1400                1405                1410

Val Thr Gly Gln Gln Ile Ile Asn Gly Glu Thr Gln Tyr Phe Arg
    1415                1420                1425

Thr Asp Gly Arg Gln Val Lys Gly Gln Ile Ile Ala Asp Gly Asp
    1430                1435                1440

Lys Gln His Tyr Tyr Asp Ala Tyr Ser Gly Asn Leu Val Lys Asn
    1445                1450                1455

Asn Phe Val Thr Val Asp Gln Gly Lys Thr Trp Tyr Tyr Ala Asp
    1460                1465                1470

Gln Asp Gly Asn Leu Ser Leu Val Ala Gln
    1475                1480

<210> SEQ ID NO 15
<211> LENGTH: 1446
<212> TYPE: PRT
<213> ORGANISM: Leuconostoc pseudomesenteroides

<400> SEQUENCE: 15

Asp Gln Asn Val Asn Asp Thr Ser Val Thr Thr Thr Gln Asp Val
1               5                   10                  15

Thr Thr Asp Gln Asp Thr Gly Ile Asp Ala Ser Val Thr Thr Val
                20                  25                  30

Ser Pro Asn Leu Asp Asp Thr Gln Val Asp Asn Thr Asn Ile Gln Thr
                35                  40                  45

Ser Thr Asp Gln Lys Asp Ser Lys Gly Thr Thr Gln Thr Val Glu
        50                  55                  60

Thr Asp Val Thr Thr Asn Ser Gln Ser Thr Asp Thr Thr Ala Val Thr
```

-continued

```
                65                  70                  75                  80
Ala Gln Thr Asn Gln Thr Glu Thr Ile Gln Asn Ser Asp Ala Thr Thr
                    85                  90                  95

Glu Thr Gly Leu Val Thr Val Asn Asn Gln Val Arg Tyr Val Asn Pro
                100                 105                 110

Asp Gly Thr Val Leu Lys Gly Ala Tyr Lys Thr Ile Asn Gly Asn Thr
                115                 120                 125

Tyr Tyr Phe Asp Asp Asn Ser Gly Asp Ala Leu Ile Gly Ile His Lys
                130                 135                 140

Ile Gly Glu Ser Ile Lys Gly Phe Gly Leu Thr Gly Val Gln Val Lys
145                 150                 155                 160

Gly Asp Tyr Leu Thr Ala Val Asn Gly Asp Lys Tyr Tyr Phe Asp Ser
                165                 170                 175

Asp Gly Asn Thr Val Ser Gly Val Gln Gln Ile Asn Gly Lys Thr Tyr
                180                 185                 190

Tyr Phe Asp Ser Thr Gly Lys Leu Met Lys Gly Tyr Thr Ala Val Leu
                195                 200                 205

Asn Gly Val Val Thr Phe Phe Asn Ser Thr Thr Gly Glu Ala Asp Asn
                210                 215                 220

Thr Asp Ala Ser Thr Ile Lys Thr Gly Val Thr Ile Asp Asn Ser Asp
225                 230                 235                 240

Tyr Thr Ala His Asn Ala Ala Tyr Asp Asn Thr Ala Ala Ser Phe Asp
                245                 250                 255

Asn Ile Asn Gly Tyr Leu Thr Ala Glu Ser Trp Tyr Arg Pro Lys Glu
                260                 265                 270

Ile Leu Glu Asn Gly Glu Ser Trp Arg Pro Ser Thr Ala Glu Asp Lys
                275                 280                 285

Arg Pro Ile Leu Ile Thr Trp Gln Pro Asp Ile Val Thr Glu Val Asn
                290                 295                 300

Tyr Leu Asn Met Met Ser Ala Asn Gly Leu Leu Ser Ile Asn Ala Pro
305                 310                 315                 320

Phe Thr Thr Ala Ser Asp Leu Ala Ile Met Asn Asp Ala Val Arg Ala
                325                 330                 335

Val Gln Lys Asn Ile Glu Ile Arg Ile Ser Gln Glu Lys Ser Thr Asp
                340                 345                 350

Trp Leu Lys Ala Leu Met Thr Gln Phe Ile Asn Thr Gln Pro Gln Trp
                355                 360                 365

Asn Glu Val Ser Glu Ser Pro Ser Asn Asp His Leu Gln Gly Gly Ala
                370                 375                 380

Leu Thr Tyr Val Asn Ser Pro Leu Thr Pro Asp Ala Asn Ser Asn Phe
385                 390                 395                 400

Arg Leu Leu Asn Arg Thr Pro Thr Asn Gln Ser Gly Thr Thr Arg Tyr
                405                 410                 415

Asp Thr Asp Lys Ser Glu Gly Gly Phe Glu Leu Leu Leu Ala Asn Asp
                420                 425                 430

Val Asp Asn Ser Asn Pro Val Val Gln Ala Glu Gln Leu Asn Trp Leu
                435                 440                 445

Tyr Tyr Leu Met Asn Phe Gly Ser Ile Thr Ala Asn Asp Pro Thr Ala
                450                 455                 460

Asn Phe Asp Gly Ile Arg Val Asp Ala Val Asp Asn Val Asp Ala Asp
465                 470                 475                 480

Leu Leu Gln Ile Ala Ser Asp Tyr Phe Lys Leu Ala Tyr Gly Thr Ser
                485                 490                 495
```

```
Leu Ser Asp Thr Asn Ala Asn Gln His Leu Ser Ile Leu Glu Asp Trp
            500                 505                 510

Ser Ala Asn Asp Ala Glu Tyr Met Ser Lys Thr Gly Ser Asn Gln Leu
    515                 520                 525

Thr Met Asp Thr Tyr Thr Gln Gln Gln Leu Leu Phe Ser Leu Thr Lys
530                 535                 540

Gln Val Gly Asn Arg Ala Asp Met Arg Arg Phe Leu Glu Tyr Phe Met
545                 550                 555                 560

Ile Asn Arg Ala Asn Asp Ser Thr Glu Asn Ile Ala Thr Pro Asn Tyr
                565                 570                 575

Ser Phe Val Arg Ala His Asp Ser Glu Val Gln Thr Val Ile Ala Thr
            580                 585                 590

Ile Ile Lys Asp Leu His Pro Asp Val Val Asn Ser Leu Ala Pro Thr
        595                 600                 605

Gln Ala Gln Leu Glu Glu Ala Phe Ala Val Tyr Asn Ala Asp Met Asn
    610                 615                 620

Arg Val Asp Lys Gln Tyr Thr Gln Tyr Asn Met Pro Ser Ala Tyr Ala
625                 630                 635                 640

Met Leu Leu Thr Asn Lys Asp Thr Ile Pro Arg Val Tyr Tyr Gly Asp
                645                 650                 655

Leu Tyr Thr Asp Asp Gly Glu Tyr Met Gly Thr Gln Thr Pro Tyr Tyr
            660                 665                 670

Asp Ala Ile Val Asn Leu Leu Gln Ser Arg Val Lys Tyr Val Ala Gly
        675                 680                 685

Gly Gln Ser Met Ala Val Asp Gln His Asp Ile Leu Thr Ser Val Arg
    690                 695                 700

Tyr Gly Lys Asn Leu Ala Asp Ala Asn Ala Thr Ser Asp Asp Leu Thr
705                 710                 715                 720

Ser Ile Asn Ser Gly Ile Gly Val Ile Val Ser Asn Asn Pro Asn Leu
                725                 730                 735

Ser Leu Ala Ser Gly Glu Thr Val Val Leu His Met Gly Ile Ala His
            740                 745                 750

Ala Asn Gln Val Tyr Arg Glu Ile Leu Glu Thr Thr Asp Asn Gly Ile
        755                 760                 765

Ala Asn Asn Thr Asp Ile Phe Lys Thr Thr Asp Ser Asn Gly Asp Leu
    770                 775                 780

Ile Phe Thr Ala Ser Glu Ile His Gly Tyr Ser Asn Val Gln Val Ser
785                 790                 795                 800

Gly Phe Leu Ser Val Trp Ala Pro Lys Asp Ala Thr Asp Asn Gln Asp
                805                 810                 815

Val Arg Thr Ala Ala Ser Glu Ser Thr Ser Ser Asp Gly Asn Thr Leu
            820                 825                 830

His Ser Asn Ala Ala Leu Asp Ser Asn Ile Ile Tyr Glu Gly Phe Ser
        835                 840                 845

Asn Phe Gln Ser Thr Pro Gln Ser Glu Ser Glu Phe Ala Lys Val Lys
    850                 855                 860

Ile Ala Ala Asn Val Asn Leu Phe Lys Ser Trp Gly Val Thr Ser Phe
865                 870                 875                 880

Gln Met Ala Pro Gln Tyr Arg Ser Ser Thr Asp Thr Ser Phe Leu Asp
                885                 890                 895

Ser Ile Ile Gln Asn Gly Tyr Ala Phe Thr Asp Arg Tyr Asp Leu Gly
            900                 905                 910
```

```
Phe Glu Thr Pro Thr Lys Tyr Gly Thr Asp Gln Gln Leu Arg Asp Ala
        915                 920                 925

Ile Lys Ala Leu His Ala Asn Gly Ile Gln Ala Met Ala Asp Phe Val
        930                 935                 940

Pro Asp Gln Ile Tyr Asn Leu Pro Gln Thr Glu Leu Val Ser Val Ser
945                 950                 955                 960

Arg Thr Asp Ser Leu Gly Asn Gln Ser Ala Asn Ser Asn Ala Ala Asn
            965                 970                 975

Val Leu Tyr Val Ser His Thr Val Gly Gly Glu Tyr Gln Ser Lys
                980                 985                 990

Tyr Gly Gly Glu Phe Leu Ala Leu Ile Lys Ser Lys Tyr Pro Ser Leu
        995                 1000                1005

Phe Lys Thr Ile Gln Val Ser Thr Gly Leu Pro Ile Asp Asp Ser
    1010                1015                1020

Thr Lys Ile Lys Glu Trp Ser Ala Lys Tyr Phe Asn Gly Ser Asn
    1025                1030                1035

Ile Gln Gly Arg Gly Phe Gly Tyr Val Leu Ser Asp Gly Gly Thr
    1040                1045                1050

Gln Asn Tyr Phe Lys Val Ile Ser Asn Ser Thr Asp Asp Phe
    1055                1060                1065

Leu Pro Asn Gln Leu Thr Gly Gln Pro Thr Met Thr Gly Phe Glu
    1070                1075                1080

Gln Thr Ser Lys Gly Ile Val Tyr Tyr Ser Lys Ser Gly Ile Gln
    1085                1090                1095

Ala Lys Asn Gln Phe Val Lys Asp Asp Val Ser Gly Asn Tyr Tyr
    1100                1105                1110

Tyr Phe Asn Lys Asn Gly Leu Met Thr Ile Gly Ser Lys Thr Ile
    1115                1120                1125

Asn Gly Lys Asn Tyr Met Phe Leu Pro Asn Gly Val Glu Leu Arg
    1130                1135                1140

Gly Ser Phe Leu Gln Thr Ala Asp Gly Thr Val Asn Tyr Tyr Ala
    1145                1150                1155

Thr Asn Gly Ala Gln Val Lys Asp Ala Tyr Val Thr Asp Thr Glu
    1160                1165                1170

Gly Asn Ser Tyr Tyr Phe Asp Gly Asp Gly Glu Met Val Thr Gly
    1175                1180                1185

Ala Tyr Thr Val Asp Gly His Ala Gln Tyr Phe Asp Val Asn Gly
    1190                1195                1200

Val Gln Thr Lys Gly Ala Ile Ile Thr Leu Asp Gly Val Gln Arg
    1205                1210                1215

Tyr Tyr Gln Ala Gly Asn Gly Asn Leu Ala Thr Asn Gln Tyr Val
    1220                1225                1230

Ser Tyr Asn Asn Ser Trp Tyr Tyr Ala Asn Ala Lys Gly Glu Leu
    1235                1240                1245

Val Thr Gly Val Gln Ser Ile Asn Gly Asn Val Gln Tyr Phe Ala
    1250                1255                1260

Ser Asn Gly Gln Gln Ile Lys Gly Gln Ile Val Val Thr Gly Asn
    1265                1270                1275

Gln Lys Ser Tyr Tyr Asp Ala Asn Thr Gly Asn Leu Ile Arg Asn
    1280                1285                1290

Asp Phe Leu Thr Pro Asp Gln Gly Lys Thr Trp Tyr Tyr Ala Asp
    1295                1300                1305

Gln Asp Gly Asn Leu Val Val Gly Val Arg Asn Ile Asn Gly His
```

```
                      1310                1315                1320

Asn Gln Tyr Phe Asp Asp Asn Gly Ile Gln Ile Lys Asp Gln Ile
            1325                1330                1335

Ile Ser Asn Asp Gly Gln Gln Tyr Tyr Tyr Gln Gly Gly Asn Gly
        1340                1345                1350

Asp Leu Val Thr Asn Arg Tyr Ile Ser Tyr Asn Asp Ser Trp Tyr
    1355                1360                1365

Tyr Ala Asp Ala Thr Gly Val Leu Val Thr Gly Gln Gln Ile Ile
1370                1375                1380

Asn Gly Glu Thr Gln Tyr Phe Arg Thr Asp Gly Arg Gln Val Lys
        1385                1390                1395

Gly Gln Ile Ile Ala Asp Gly Asp Lys Gln His Tyr Tyr Asp Ala
    1400                1405                1410

Tyr Ser Gly Asn Leu Val Lys Asn Asn Phe Val Thr Val Asp Gln
1415                1420                1425

Gly Lys Thr Trp Tyr Tyr Ala Asp Gln Asp Gly Asn Leu Ser Leu
        1430                1435                1440

Val Ala Gln
    1445

<210> SEQ ID NO 16
<211> LENGTH: 24
<212> TYPE: PRT
<213> ORGANISM: Lactobacillus reuteri

<400> SEQUENCE: 16

Trp Asn Lys Asp Ser Glu Asn Val Asp Tyr Gly Gly Leu Gln Leu Gln
1               5                   10                  15

Gly Gly Phe Leu Lys Tyr Val Asn
            20

<210> SEQ ID NO 17
<211> LENGTH: 22
<212> TYPE: PRT
<213> ORGANISM: Leuconostoc mesenteroides

<400> SEQUENCE: 17

Trp Asn Ile Ala Ser Glu Ser Lys Gly Thr Asp His Leu Gln Gly Gly
1               5                   10                  15

Ala Leu Leu Tyr Val Asn
            20

<210> SEQ ID NO 18
<211> LENGTH: 22
<212> TYPE: PRT
<213> ORGANISM: Leuconostoc mesenteroides

<400> SEQUENCE: 18

Trp Asn Glu Thr Ser Glu Asp Met Ser Asn Asp His Leu Gln Asn Gly
1               5                   10                  15

Ala Leu Thr Tyr Val Asn
            20

<210> SEQ ID NO 19
<211> LENGTH: 22
<212> TYPE: PRT
<213> ORGANISM: Streptococcus sobrinus

<400> SEQUENCE: 19
```

```
Trp Asn Gly Glu Ser Glu Lys Pro Tyr Asp Asp His Leu Gln Asn Gly
1               5                   10                  15

Ala Leu Leu Phe Asp Asn
            20

<210> SEQ ID NO 20
<211> LENGTH: 22
<212> TYPE: PRT
<213> ORGANISM: Leuconostoc pseudomesenteroides

<400> SEQUENCE: 20

Trp Asn Glu Val Ser Glu Ser Pro Ser Asn Asp His Leu Gln Gly Gly
1               5                   10                  15

Ala Leu Thr Tyr Val Asn
            20

<210> SEQ ID NO 21
<211> LENGTH: 24
<212> TYPE: PRT
<213> ORGANISM: Leuconostoc citreum

<400> SEQUENCE: 21

Trp Asn Lys Gln Thr Glu Asp Glu Ala Phe Asp Gly Leu Trp Leu Gln
1               5                   10                  15

Gly Gly Phe Leu Ala Tyr Gln Asp
            20
```

MODIFIED ENZYMES FOR PRODUCING INCREASED ISOMELEZITOSE

CROSS-REFERENCE

The present application claims priority to U.S. Provisional Patent Application Ser. No. 62/500,104 filed May 2, 2017, the content of which is expressly incorporated herein by reference.

BACKGROUND OF THE INVENTION

Field of Invention

Certain lactic acid bacteria produce glycosyltransferases known as glucansucrases, which synthesize α-D-glucans via glucosyl transfer from sucrose. Herein is provided compositions and methods for the synthesis of isomelezitose in high yields by genetically engineered variants of glucansucrases. The methods and variant enzymes are amenable to large-scale production of isomelezitose for food, industrial and biomedical applications.

Background

Isomelezitose is a rare non-reducing trisaccharide composed of glucose and fructose, with the structure α-D-glucopyranosyl-(1→6)-β-D-fructofuranosyl-(2↔1)-α-D-glucopyranoside (Chiba et al., Agric. Biol. Chem., (1979) 43:775-9). It has been produced as a minor acceptor product in reactions of alternanusucrase (Côté et al., Biocatal. Biotransform (2008) 26:161-8) and dextransucrase (Shi et al., Food Chem., (2016) 190:226-36). There have been numerous attempts to improve the production of isomelezitose since it was first described as a minor transglycosylation product using α-glucosidase from brewer's yeast (Chiba et al., supra). Various α-glucosidase enzymes and whole-cell systems from Serratia plymuthica (Fujii et al., J. Japanese Soc. Food Sci. Tech., (1983) 30:339-44), Bacillus stearothermophilus (see, e.g., JP 2955589; JP App. 04-030771, JP 3427984 (1992)), and Protaminobacter rubrum (WO 1999022013) were able to produce isomelezitose, all at low yields in the range of 8-11%. Attempts to genetically modify an α-glucosidase from Bacillus sp. SAM1606 were successful in shifting transglycosylation from theanderose to predominantly isomelezitose, but yields were still around 7% and isomelezitose was quickly degraded by the same enzyme (Inohara-Ochiai et al., J. Biosci. Bioeng., (2000) 89:431-37; Okada et al., J. Molec. Catalysis B, Enzymatic, (2002) 16:265-74). In 2012, Görl et al. (J. ChemBioChem., (2012) 13:149-56) identified a sucrose isomerase from Protaminobacter rubrum that had significant sequence identity with the Bacillus sp. SAM1606 α-glucosidase and then significantly improved synthesis of isomelezitose by substitution of several different amino acid loci identified using alignments and docking studies. However, yields were still only 22% using approximately 0.3 M sucrose. Furthermore, the enzyme eventually shifts to synthesis of the byproduct isomaltulose, so this method relied on continuous isolation of the isomelezitose product via chromatography over silica gel.

The trisaccharide, isomelezitose, is not a substrate for salivary enzymes or bacteria of the upper gastrointestinal tract or small intestine, but is cleaved by bifidobacteria components of the colon microflora (WO 1999022013). This unusual sugar is part of the sweetness component of honey (Gomez Barez et al., Chromatographia, (1999) 50:461-9), but is noncariogenic, low calorie and suitable for diabetic foods (Görl et al., supra). Thus, if it can be produced in large enough quantities to make it economically feasible, it has potential applications in the production of vaccines, drugs, and nutritional food supplements.

The present disclosure addresses the low production of isomelezitose by bacterial enzymes. Several different amino acid substitutions of a key leucine residue (L441) in the wild-type DsrI enzyme from Leuconostoc mesenteroides NRRL-B-1118 (Côté and Skory, Appl. Microbiol. Biotechnol., (2012) 93:2387-94) were examined. Depending on the modification, product formation shifted between water-insoluble glucan, isomelezitose, and total oligosaccharides among L441 mutants and some previously studied T654 mutants (Côté and Skory, Appl. Microbiol. Biotechnol., (2014) 98:6651-8). Analogous modifications to other heterologously expressed glucansucrases were also analyzed and expressed extracellularly in Lactococcus lactis using a previously described technique (Skory and Côté, Appl. Microbiol. Biotechnol., (2015) 99:10001-10). As presented herein, genetically modified enzymes that can produce isomelezitose in high yields are provided.

SUMMARY OF THE INVENTION

Provided herein are multiple embodiments of the invention of this application. One embodiment provided is a modified glucansucrase enzyme comprising a domain B motif, wherein the leucine residue equivalent to L441 of the L. mesenteroides DsrI protein (SEQ ID NO:5) in the domain B motif is substituted with an amino acid other than leucine and wherein the modified enzyme produces at least twice as much isomelezitose from sucrose as compared to the unmodified glucansucrase enzyme. In some embodiments, the naturally-occurring leucine residue is replaced with a proline residue. In one embodiment, the modified enzyme is at least 90% identical to the full-length L. mesenteroides DsrI protein (SEQ ID NO:5) or that protein without the signal sequence (SEQ ID NO:6) where the leucine residue at position 441 (of SEQ ID NO:5) or position 400 (of SEQ ID NO:6) is substituted with an amino acid other than leucine, such as substituted with arginine, asparagine, aspartic acid, glutamine, glutamic acid, glycine, isoleucine, lysine, proline, serine, threonine, or valine. In another embodiment, the modified enzyme is at least 90% identical to the full-length L. mesenteroides DsrS protein (SEQ ID NO:8) or that protein without the signal sequence (SEQ ID NO:9), where the leucine residue at position 459 (of SEQ ID NO:8) or position 417 (of SEQ ID NO:9) is substituted with an amino acid other than leucine, such as being substituted with proline. In still another embodiment, the modified enzyme is at least 90% identical to the full-length L. citreum Asr protein (SEQ ID NO:2) or that protein without the signal sequence (SEQ ID NO:3), where the leucine residue at position 544 (of SEQ ID NO:2) or position 505 (of SEQ ID NO:3) is substituted with an amino acid other than leucine, such as being substituted with glutamic acid, proline, or serine. In yet another embodiment, the modified enzyme is at least 90% identical to the full-length S. sobrinus GtfI protein (SEQ ID NO:11) or that protein without the signal sequence (SEQ ID NO:12), where the leucine residue at position 350 (of SEQ ID NO:11) or position 312 (of SEQ ID NO:12) is substituted with an amino acid other than leucine, such as being substituted with arginine, glutamic acid, proline, or serine. In an additional embodiment, the modified enzyme is at least 90% identical to the full-length L. pseudomesenteroides GtfG protein (SEQ ID NO:14) or that protein without the signal sequence (SEQ ID NO:15), where the leucine residue at position 417 (of SEQ ID NO:14) or position 380 (of SEQ ID NO:15) is substituted with an amino acid other than leucine, such as being substituted with proline.

Also provided herein are DNA molecules encoding any of these modified proteins and host cells containing these DNA molecules.

In still another embodiment of the invention, the present application provides a method of producing isomelezitose comprising the steps of contacting any of the modified enzymes provided herein, alone or in combination, with a solution comprising a carbohydrate source, and allowing the modified enzyme(s) to convert at least a portion of the carbohydrate source to isomelezitose. In some embodiments, the modified enzyme is expressed in a recombinant host cell, from which the modified enzyme can be purified prior to contacting it with a carbohydrate source. In preferred embodiments, the carbohydrate source contains sucrose. The sucrose can be in aqueous solution and at a concentration of approximately 1.0M.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

FIG. 1 provides an alignment of sequences of conserved domain B motifs from the catalytic domain of various glucansucrases analyzed. The position of the key leucine residue is indicated (*). Conserved regions are shaded. Wild type sequences provided are, from top to bottom, the GTF180 enzyme domain B motif (SEQ ID NO: 16), the DsrI enzyme domain B motif (SEQ ID NO: 17), the DsrS enzyme domain B motif (SEQ ID NO: 18), the GtfI enzyme domain B motif (SEQ ID NO: 19), the GftG enzyme domain B motif (SEQ ID NO: 20), and the Asr enzyme domain B motif (SEQ ID NO: 20). DsrI and DsrS sequences are from *L. mesenteroides*, GtfI is from *S. sobrinus*, GtfG is from *L. pseudomesenteroides*, and Asr is from *L. citreum*.

DETAILED DESCRIPTION OF THE INVENTION

Figure 2:
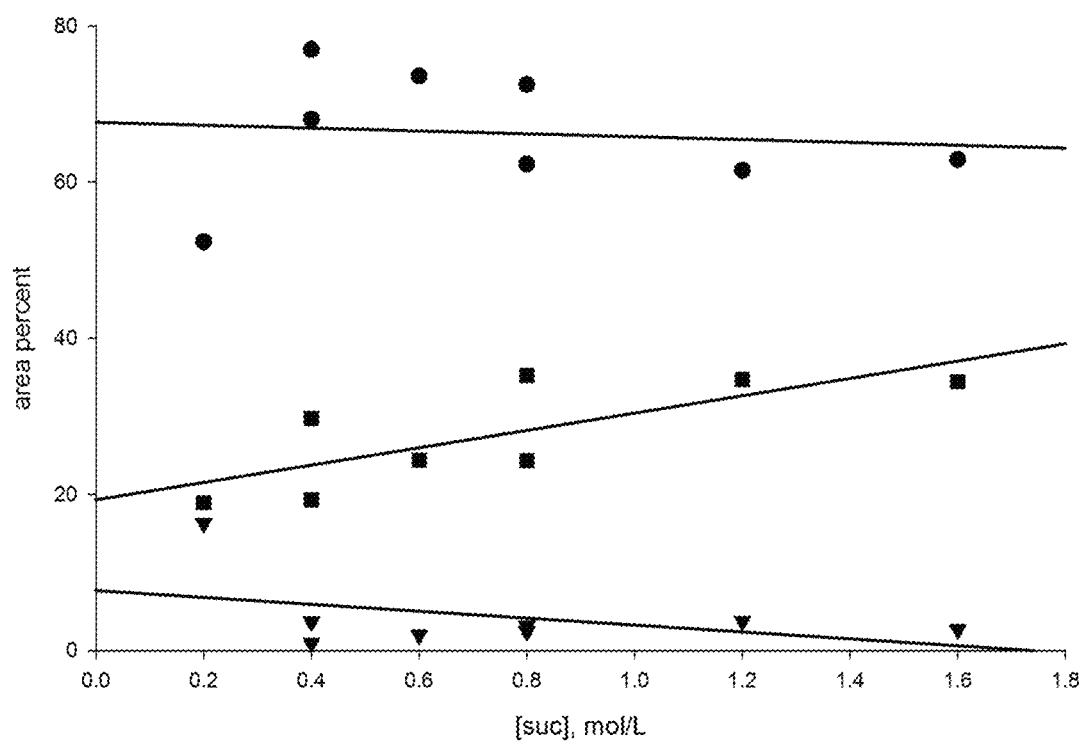
FIG. 2 provides a graph showing the effect of initial sucrose concentration on relative yields of fructose (•), isomelezitose (▼), and the disaccharides leucrose plus isomaltulose (■) by wild type *L. mesenteroides* B-1118 DsrI protein.

Provided herein are modified enzymes (glucansucrases) containing mutations in a highly conserved leucine residue within a conserved motif. These modified enzymes are capable of producing elevated levels of isomelezitose from sucrose as compared to unmodified (wild-type) enzymes. In some embodiments, such modified enzymes are exposed to sucrose solutions and allowed to produce isomelezitose. In preferred embodiments, the modified enzymes of the present invention are produced by recombinant cells and at least partially purified before exposure to sucrose solutions.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of fungal genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered host cells producing genetically modified glucansucrases from lactic acid bacteria, including *Leuconostoc mesenteroides*.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "equivalent amino acid", and grammatical variations thereof, refers to the same highly conserved amino acid residue in a conserved protein domain, regardless of its numerical position in a given amino acid sequence. For example, all leucine residues indicated by the asterisk and bold font in FIG. 1, are equivalent amino acids.

As described herein, a single amino acid residue substitution can be indicated as follows: the original amino acid residue (expressed as a single-letter abbreviation), followed by the position of the original amino acid residue (i.e., a numerical expression), followed by the new amino acid residue (expressed as a single-letter abbreviation) to be inserted in place of the original amino acid residue. For example, "L441G" means that the original leucine (L) residue at position 441 is to be replaced by the new glycine (G) residue. For multiple substitutions (e.g., double-substitutions, triple-substitutions, and quadruple-substitutions), the various substitutions are separated by either a slash (/) or by a space.

Modified enzymes of the present invention also include enzymes with high identity or homology to a reference sequence. For example, proteins having 80%, 81%, 82%, 83%, 84%, 85%, 86%, 87%, 88%, 89%, 90%, 91%, 92%, 93%, 94%, 95%, 96%, 97%, 98% or 99% identity to any of SEQ. ID. NOs: 2, 3, 5, 6, 8, 9, 11, 12, 14 or 15 are provided herein. As a practical matter, whether any particular amino acid sequence having a percentage identity to a given amino acid sequence can be determined conventionally using known computer programs to find the best segment of homology between two sequences. When using sequence alignment program to determine whether a particular sequence is, for instance, 96% identical to a reference sequence according to the present invention, the parameters are set, of course, such that the percentage of identity is calculated over the full length of the reference peptide sequence and that gaps in homology of up to 4% of the total number of amino acids in the reference sequence are allowed.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Recombinant host cells, in the present context, are those which have been genetically modified to contain an isolated nucleic molecule of the instant invention. The nucleic acid can be introduced by any means known to the art which is appropriate for the particular type of cell, including without limitation, transformation, transfection, lipofection, electroporation or any other methodology known by those skilled in the art.

In practicing some embodiments of the invention disclosed herein, it can be useful to modify the DNA of a strain of lactic acid bacteria, or another target organism that produces a glucansucrase to be modified. In many embodiments, such modification involves replacing an innate gene with an artificially modified version, such that a modified protein is produced when the modified gene is expressed. Alternately, isolated nucleic acids encoding any of the proteins of the present invention can be inserted into the genome of any desired host cell. Such modifications that result in the change of one or more amino acids from a wild-type sequence can be achieved using any technique known to those of skill in the art.

Alternately, expression plasmids containing a modified gene of interest can be introduced in a host from which the gene was not originally derived (e.g., expressing a *L. mesenteroides* gene in *Escherichia coli*). Where a recombinant nucleic acid is intended for expression, cloning, or replication of a particular sequence, DNA constructs prepared for introduction into a prokaryotic or eukaryotic host can comprise a replication system (i.e. vector) recognized by the host, including the intended DNA fragment encoding the desired polypeptide, and can also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

Vectors and other nucleic acids introduced into a host cell will likely contain a selectable marker, that is, a gene encoding a protein necessary for the survival or growth of a host cell transformed with the nucleic acid. Although such a marker gene can be carried on another polynucleotide sequence co-introduced into the host cell, it is most often contained on the transforming nucleic acid. Only those host cells into which the marker gene has been introduced will survive and/or grow under selective conditions. Typical selection genes encode proteins that (a) confer resistance to antibiotics or other toxic substances, e.g., hygromycin, ampicillin, neomycin, methotrexate, etc.; (b) complement auxotrophic deficiencies; or (c) supply critical nutrients not available from complex media. The choice of the proper selectable marker will depend on the host cell and appropriate markers for different hosts are well known in the art.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) *Current Protocols in Molecular Biology*, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Hybridization-based screening of genetically altered strains typically utilizes homologous nucleic acid probes with homology to a target nucleic acid to be detected. The extent of homology between a probe and a target nucleic acid can be varied according to the particular application. Homology (level of sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, word-length=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov. Additional tools, such as Lipman-Pearson alignment can also be utilized. (Pearson & Lipman, Proc. Nat'l. Acad. Sci. U.S.A., (1988) 85:2444-8).

Glucansucrases

Glucansucrases (from Glycoside-Hydrolase (GH)-family 70 (EC. 2.4.1.5)) are extracellular enzymes produced by lactic acid bacteria of the genera *Leuconostoc*, *Streptococcus*, or *Lactobacillus* (Monsan et al., Int'l. Dairy J., (2001) 11:675-85). Glucansucrases are a type of glucosyltransferase that catalyzes the transfer of D-glucopyranosyl units from sucrose to form α-glucan chains. These enzymes are capable of catalyzing the synthesis of several different polymeric α-glucosidic linkages that affect molecular mass, branching, and solubility of the polysaccharide. In general, α-glucans containing mostly α(1→6) linkages are water-soluble (e.g., dextran), while those made primarily of α(1→3) linkages are water-insoluble. The enzymes of the GH-family 70 are diverse, being able to synthesize all the types of glucosidic linkages, namely α-1,2; α-1,3; α-1,4; or α-1,6 glucosidic bonds. Thus, depending on the enzyme specificity, a wide range of glucans can be produced, varying in terms of size, structure, degree of branches and spatial arrangements.

Despite these divergent capabilities, enzymes of the GH-family 70 have highly conserved components. They are characterized by having the same general structure consisting of a signal sequence, a variable region at the N-terminus, a conserved catalytic domain, and a C-terminal domain typically comprised of a series of homologous repeating units (Moulis et al., J. Biol. Chem., (2006) 281:31254-67). The catalytic domain is predicted to be organized in a $(\beta/\alpha)_8$-barrel (MacGregor et al., FEBS Lett. (1996) 378: 263-6).

One such conserved motif ("domain B") in these enzymes is demonstrated in FIG. 1. Crystal structure analysis of GTF180 demonstrates that domain B is part of the active site of the catalytic domain and shapes the binding groove near the acceptor binding site (Vujicic-Zagar et al., Proc. Nat'l. Acad. Sci. U.S.A., (2010) 107:21406-11). Protein sequence alignment of domain B regions from various glucansucrases demonstrate that leucine is highly conserved in the amino acid positions corresponding with L940 *L. reuteri* GTF180, L441 for *L. mesenteroides* DsrI, L459 for *L. mesenteroides* DsrS, L350 for *S. sobrinus* GtfI, L544 for *L. citreum* Asr, and L417 for *L. pseudomesenteroides*. Thus, each of these leucine residues are the equivalent of each other.

As demonstrated herein via the various exemplary glucansucrases modified as described, this leucine residue (i.e., the equivalent leucine to L441 from SEQ ID NO:5), can be modified to improve production of isomelezitose. This leucine residue can be identified in most glucansucrases as the second amino acid position in the following protein motif ("domain B" motif) presented in PROSITE pattern format: [HQW]-L-Q-[NG]-G-[FAY]-[LV]-X-[YF]-X-[ND]. A few exceptions among this diverse enzyme group that lack an equivalent leucine residue at this position include reuteran-producing glucansucrase (e.g., reuteransucrase GtfA from *L. reuteri* (Kralj, et al., Appl. Environ. Microbiol., (2002) 68:4283-91) and the catalytic domain 2 of α(1→2) synthesizing glucansucrases (e.g., DsrE from *L. mesenteroides* (Bozonnet, et al., J. Bacteriol., (2002)184:5753-61), which contain a phenylalanine in this position.

Table 1 provides wild-type nucleic acid and amino acid sequences of the various glucansucrases mutated and analyzed as described herein.

TABLE 1

Sequences of wild-type enzymes

| Type | Sequence | SEQ ID NO: |
|---|---|---|
| asr coding sequence (*L. citreum*) | ATGAAACAACAAGAAACAGTTACCCGTAAAAAACTTTATAAATCCGG TAAGGTTTGGGTTGCAGCAGCTACTGCATTTGCGGTATTGGGGGTTTC AACTGTAACAACAGTCCATGCGGATACAAATTCGAATGTCGCTGTTA AGCAAATAAATAATACAGGAACCAATGATTCTGGCGAAAAAAAGGT ACCGGTTCCATCAACTAATAATGATAGTTTGAAGCAAGGAACAGATG GTTTTTGGTATGATTCAGACGGCAATCGTGTCGATCAGAAGACCAATC AGATTCTGCTTACTGCGGAACAACTTAAAAAAAATAACGAAAAAAAT TTATCAGTAATCAGTGATGATACATCAAAAAAAGATGATGAAAATAT TTCTAAGCAGACCAAAATTGCTAATCAACAAACAGTAGATACTGCTA AAGGCCTGACTACCAGTAATTTATCTGATCCCATCACTGGGGGTCACT ATGAAAATCACAATGGCTACTTTGTTTATATAGATGCTTCAGGAAAAC AAGTAACAGGTTTGCAAAATATTGATGGTAATTTACAATATTTTGATG ACAATGGATATCAAGTCAAGGGATCCTTCCGAGATGTCAACGGCAAG CATATCTATTTTGATTCAGTAACAGGGAAAGCTAGTTCAAATGTTGAT ATTGTTAACGGTAAAGCTCAAGGATATGATGCGCAAGGCAACCAATT AAAGAAAAGTTATGTCGCCGATAGTTCTGGGCAAACTTACTATTTTGA TGGTAATGGCCAACCGTTAATCGGCTTGCAAACAATTGATGGGAACC TACAATATTTTAACCAACAAGGGGTTCAAATAAAGGGTGGTTTCCAA GATGTTAACAATAAACGTATTTATTTTGCACCAAACACAGGTAATGCC GTTGCCAATACTGAAATAATTAACGGTAAATTACAGGGGCGTGACGC AAATGGTAACCAGGTAAAGAATGCATTTAGTAAAGATGTTGCAGGAA ATACATTTTATTTTGACGCAAACGGTGTGATGTTAACAGGGTTGCAAA CTATTTCAGGAAAGACATATTATCTTGATGAACAAGGACACCTGAGA AAAAATTACGCGGGAACATTCAATAATCAGTTTATGTACTTCGATGCT GATACAGGTGCGGGTAAAACAGCGATTGAATATCAATTTGATCAAGG ATTGGTATCACAAAGTAATGAAAATACTCCTCACAATGCCGCAAAGT CTTATGATAAAAGTAGTTTTGAAAATGTTGATGGTTACTTAACAGCAG ATACATGGTATCGTCCAACCGATATTTTAAAAAATGGAGATACTTGG ACGGCATCTACCGAAACTGATATGCGTCCGCTTTTAATGACATGGTGG CCTGACAAACAAACACAAGCAAATTACTTGAATTTTATGTCTAGTAA AGGACTTGGTATAACGACCACTTATACAGCAGCTACGTCACAAAAAA CACTAAATGACGCAGCCTTTGTTATTCAAACAGCAATTGAACAACAA ATATCTTTGAAAAAAAGTACTGAGTGGTTACGTGATGCAATTGATAGT TTTGTGAAGACGCAAGCTAATTGGAATAAGCAAACAGAAGATGAAGC TTTCGATGGTTTGCAGTGGCTTCAAGGGGGATTCCTAGCTTATCAAGA TGATTCACATCGGACGCCGAATACTGATTCAGGAAATAACAGAAAAC TAGGACGTCAACCAATTAATATCGATGGTTCGAAAGATACAACTGAT GGTAAAGGCTCTGAATTCTTATTAGCTAACGATATTGACAACTCAAAT CCGATTGTTCAAGCTGAGCAATTAAACTGGCTACACTATTTAATGAAT TTTGGTAGTATTACAGGTAATAATGACAATGCGAATTTTGATGGCATT CGTGTAGATGCTGTTGATAATGTTGATGCTGATTTACTAAAAATAGCT GGCGATTATTTTAAAGCTCTATATGGTACAGATAAAAGCGACGCCAA TGCCAATAAGCATTTGTCTATTTTAGAAGACTGGAACGGTAAAGATCC TCAGTATGTTAATCAACAGGGCAATGCGCAATTAACAATGGATTACA CAGTTACTTCACAGTTTGGCAATTCTCTAACACATGGCGCCAACAACA GGAGTAACATGTGGTATTTCTTAGATACTGGCTATTATCTTAATGGAG ATCTTAATAAGAAGATAGTAGATAAGAACCGTCCAAATTCTGGCACT TTGGTTAACAGAATTGCTAATTCAGGTGATACAAAAGTTATTCCAAAT TATAGTTTTGTTAGAGCACATGATTACGATGCTCAAGATCCAATTAGA AAAGCCATGATTGATCATGGTATTATTAAAAACATGCAGGATACTTTC ACTTTTGACCAACTGGCTCAGGGAATGGAATTCTACTATAAAGATCA AGAGAATCCGTCTGGTTTCAAAAAGTATAACGATTATAACTTACCTAG TGCTTATGCAATGTTGTTGACTAATAAGGATACTGTACCTCGTGTCTA TTATGGAGATATGTACCTCGAAGGCGGGCAATATATGGAAAAAGGGA CGATTTACAATCCTGTCATTTCAGCGTTGCTCAAAGCTAGAATAAAAT ATGTTTCTGGTGGGCAAACAATGGCTACCGATAGTTCTGAAAAGAC CTTAAAGATGGCGAAACTGATTTGTTAACAAGTGTTCGATTTGGTAAA GGAATTATGACATCAGATCAAACCACAACACAAGACAATAGCCAAGA TTATAAAAATCGAGGCATCGGTGTCATTGTTGGTAATAACCCTGACCT TAAGTTGAACAATGATAAGACCATTACCTTGCATATGGGAAAGGCGC ATAAGAATCAACTTTACCGTGCCTTAGTATTATCAAATGACTCAGGAA TTGATGTTTATGATAGTGATGATAAAGCACCAACTTTGAGAACAAAT GACAACGGTGACTTGATTTTCCATAAGACAAATACGTTTGTGAAGCA AGATGGAACTATTATAAATTACGAAATGAAGGGATCATTAAATGCTT TAATTTCAGGTTATTAGGTGTCTGGGTGCCAGTTGGAGCTAGTGATT CACAAGATGCTCGTACAGTGGCAACTGAGTCATCATCAAGTAATGAT GGTTCTGTATTCCATTCAAATGCTGCATTAGATTCTAATGTTATATATG AAGGCTTTTCAAACTTTCAAGCGATGCCGACTTCTCCTGAGCAAAGTA | 1 |

TABLE 1-continued

Sequences of wild-type enzymes

| Type | Sequence | SEQ ID NO: |
|---|---|---|
| | CAAATGTTGTTATTGCAACAAAGGCTAACTTATTTAAAGAATTAGGTA<br>TTACTAGTTTTGAGTTAGCACCTCAATATAGGTCTAGTGGTGACACTA<br>ATTACGGTGGCATGTCATTCTTAGATTCTTTCTTAAATAATGGTTATGC<br>ATTTACCGATAGATATGATTTAGGCTTTAACAAAGCAGACGGGAATC<br>CTAACCCAACAAAGTATGGAACAGATCAAGATTTACGTAATGCAATA<br>GAGGCATTACACAAAAACGGCATGCAGGCTATAGCTGATTGGGTTCC<br>TGACCAAATATATGCTTTACCAGGAAAGGAAGTTGTTACCGCTACTA<br>GAGTAGACGAACGGGGAAATCAACTAAAAGACACAGATTTTGTCAAC<br>TTACTCTATGTTGCTAATACTAAAAGTAGTGGTGTGGATTATCAGGCA<br>AAGTATGGCGGCGAATTTTTAGATAAATTAAGAGAAGAGTACCCATC<br>GTTATTCAAACAGAACCAAGTATCGACAGGTCAGCCAATTGATGCTT<br>CTACAAAAATTAAGCAATGGTCAGCTAAATATATGAATGGGACCAAT<br>ATTTTACATCGAGGTGCTTATTATGTTTTGAAAGACTGGGCTACTAAC<br>CAGTATTTTAACATTGCAAAAACGAATGAAGTATTTTTGCCACTACAG<br>TTGCAGAATAAAGATGCGCAAACTGGTTTCATTAGTGATGCCTCCGGT<br>GTAAAATATTACTCAATTAGTGGTTATCAAGCAAAAGATACTTTTATT<br>GAAGATGGTAATGGGAATTGGTATTACTTTGATAAAGATGGTTACAT<br>GGTGCGTTCGCAGCAAGGAGAAATCCTATAAGAACAGTCGAAACTA<br>GTGTCAACACACGAAACGGTAATTATTACTTTATGCCAAATGGTGTCG<br>AGTTGCGCAAAGGCTTTGGAACGGATAATAGTGGTAATGTCTATTATT<br>TTGATGATCAAGGTAAGATGGTGAGAGATAAATACATTAACGATGAT<br>GCTAATAATTTTTATCACTTAAATGTTGATGGGACTATGTCTCGAGGA<br>CTATTTAAATTTGATTCTGATACTCTACAGTATTTTGCTAGTAATGGTG<br>TCCAAATAAAAGATAGTTATGCGAAGGATAGTAAAGGCAATAAATAT<br>TATTTTGACTCAGCTACAGGAAATAACGATACTGGGAAAGCCCAAAC<br>TTGGGATGGTAATGGCTACTATATTACTATTGATTCTGATGCGAACAA<br>TACAATTGGGGTTAACACAGACTACACTGCCTACATCACTAGCTCGCT<br>GCGCGAAGATGGCTTATTTGCTAACGCACCTTACGGTGTTGTAACAAA<br>AGACCAAAATGGTAACGATCTTAAGTGGCAGTATATTAACCATACGA<br>AACAGTACGAAGGGCAACAAGTGCAAGTCACGCGTCAATACACAGA<br>CAGTAAGGGAGTCAGCTGGAACTTAATTACCTTTGCTGGTGGTGATTT<br>ACAAGGACAAAGGCTTTGGGTGGATAGTCGTGCGTTAACTATGACAC<br>CATTTAAAACGATGAACCAAATAAGCTTCATTAGTTATGCTAACCGCA<br>ATGATGGGTTGTTTTTGAATGCGCCATACCAAGTCAAGGGGTATCAAT<br>TAGCTGGGATGTCCAACCAATCAAGGGCCAACAAGTGACCATTGCT<br>GGGGTGGCGAACGTTTCTGGAAAAGACTGGAGTCTGATTAGTTTTAA<br>TGGGACACAGTACTGGATTGATAGTCAGGCATTGAATACCAATTTCA<br>CACATGACATGAACCAAAAGGTCTTTGTCAATACAACTAGTAATCTTG<br>ATGGGTTATTCTTAAATGCGCCATACCGTCAACCGGGTTATAAGTTAG<br>CCGGTTTGGCTAAAAATTACAACAACCAAACGGTTACTGTTAGTCAA<br>CAGTACTTTGATGATCAAGGCACGGTCTGGAGTCAGGTTGTCCTTGGG<br>GGTCAGACGGTCTGGGTTGATAACCATGCATTGGCACAGATGCAAGT<br>TAGTGATACAGACCAACAGCTCTATGTGAATAGCAATGGTCGGAATG<br>ATGGGTTATTCTTGAATGCGCCATATCGTGGTCAAGGGTCACAACTGA<br>TAGGCATGACGGCAGATTATAATGGGCAACATGTACAAGTGACCAAG<br>CAAGGGCAAGATGCCTATGGTGCACAATGGCGTCTTATTACGCTAAA<br>TAATCAACAGGTCTGGGTTGATAGTCGCGCTTTGAGCACAACAATCAT<br>GCAAGCCATGAATGATAAATGTATGTAAATAGCAGCCAACGGACAG<br>ATGGCTTGTGGTTAAACGCACCTTATACGATGAGTGGGGCTAAATGG<br>GCTGGTGATACACGTTCAGCTAATGGGCGCTATGTCCATATTTCAAAA<br>GCTTATTCAAACGAAGTCGGCAATACATATTACTTGACGAATTTGAAT<br>GGTCAAAGCACATGGATTGACAAGCGGGCGTTTACTGTGACCTTCGA<br>TCAGGTGGTGGCATTAAATGCAACGATTGTGGCACGCCAACGACCAG<br>ATGGGATGTTTAAGACAGCACCATATGGTGAAGCGGGGCGCAGTTT<br>GTCGATTATGTGACAAACTATAACCAGCAAACCGTGCCAGTAACAAA<br>GCAACATTCAGATGCTCAGGGGAATCAATGGTACTTAGCGACAGTGA<br>ATGGGACACAATACTGGATTGATCAACGGTCATTTTCACCAGTAGTA<br>ACGAAGGTGGTTGATTATCAAGCTAAGATTGTGCCACGGACAACACG<br>TGATGGTGTGTTTAGTGGCGCACCCTATGGGGAAGTGAATGCTAAGC<br>TAGTTAACATGGCAACTGCGTATCAAAATCAAGTTGTCCATGCGACA<br>GGGGAATATACGAATGCTTCAGGGATCACATGGAGTCAGTTCGCGTT<br>AAGCGGGCAAGAAGCAAGCTATGGATTGATAAGCGTGCTTTGCAAG<br>CTTAA | |
| Asr protein<br>(L. citreum) | MKQQETVTRKKLYKSGKVWVAAATAFAVLGVSTVTTVHADTNSNV<br>AVKQINNTGTNDSGEKKVPVPSTNNDSLKQGTDGFWYDSDGNRVDQKT<br>NQILLTAEQLKKNNEKNLSVISDDTSKKDDENISKQTKIANQQTVDTAKG<br>LTTSNLSDPITGGHYENHNGYFVYIDASGKQVTGLQNIDGNLQYFDDNG<br>YQVKGSFRDVNGKHIYFDSVTGKASSNVDIVNGKAQGYDAQGNQLKKS<br>YVADSSGQTYYFDGNGQPLIGLQTIDGNLQYFNQQGVQIKGGFQDVNNK<br>RIYFAPNTGNAVANTEIINGKLQGRDANGNQVKNAFSKDVAGNTFYFDA<br>NGVMLTGLQTISGKTYYLDEQGHLRKNYAGTFNNQFMYPDADTGAGKT<br>AIEYQFDQGLVSQSNENTPHNAAKSYDKSSFENVDGYLTADTWYRPTDI<br>LKNGDTWTASTETDMRPLLMTWWPDKQTQANYLNFMSSKGLGITTTYT<br>AATSQKTLNDAAFVIQTAIEQQISLKKSTEWLRDAIDSFVKTQANWNKQ | 2 |

TABLE 1-continued

Sequences of wild-type enzymes

| Type | Sequence | SEQ ID NO: |
|---|---|---|
| | TEDEAFDGLQWLQGGFLAYQDDSHRTPNTDSGNNRKLGRQPINIDGSKD TTDGKGSEFLLANDIDNSNPIVQAEQLNWHYLMNFGSITGNNDNANFD GIRVDAVDNVDADLLKIAGDYFKALYGTDKSDANANKHLSILEDWNGK DPQYVNQQGNAQLTMDYTVTSQFGNSLTHGANNRSNMWYFLDTGYYL NGDLNKKIVDKNRPNSGTLVNRIANSGDTKVIPNYSFVRAHDYDAQDPI RKAMIDHGIIKNMQDTFTFDQLAQGMEFYYKDQENPSGFKKYNDYNLPS AYAMLLTNKDTVPRVYYGDMYLEGGQYMEKGTIYNPVISALLKARIKY VSGGQTMATDSSGKDLKDGETDLLTSVRFGKGIMTSDQTTTQDNSQDY KNRGIGVIVGNNPDLKLNNDKTITLHMGKAHKNQLYRALVLSNDSGIDV YDSDDKAPTLRTNDNGDLIFHKTNTFVKQDGTIINYEMKGSLNALISYL GVWVPVGASDSQDARTVATESSSSNDGSVFHSNAALDSNVIYEGFSNFQ AMPTSPEQSTNVVIATKANLFKELGITSFELAPQYRSSGDTNYGGMSFLD SFLNNGYAFTDRYDLGFNKADGNPNPTKYGTDQDLRNAIEALHKNGMQ AIADWVPDQIYALPGKEVVTATRVDERGNQLKDTDFVNLLYVANTKSS GVDYQAKYGGEFLDKLREEYPSLFKQNQVSTGQPIDASTKIKQWSAKY MNGTNILHRGAYYVLKDWATNQYFNIAKTNEVFLPLQLQNKDAQTGFIS DASGVKYYSISGYQAKDTFIEDGNGNWYYFDKDGYMVRSQQGENPIRT VETSVNTRNGNYYFMPNGVELRKGFGTDNSGNVYYFDDQGKMVRDKY INDDANNFYHLNVDGTMSRGLFKFDSDTLQYFASNGVQIKDSYAKDSKG NKYYFDSATGNNDTGKAQTWDGNGYYITIDSDANNTIGVNTDYTAYITS SLREDGLFANAPYGVVTKDQNGNDLKWQYINHTKQYEGQQVQVTRQY TDSKGVSWNLITFAGGDLQGQRLWVDSRALTMTPFKTMNQISFISYANR NDGLFLNAPYQVKGYQLAGMSNQYKGQQVTIAGVANVSGKDWSLISFN GTQYWIDSQALNTNFTHDMNQKVFVNTTSNLDGLFLNAPYRQPGYKLA GLAKNYNNQTVTVSQQYFDDQGTVWSQVVLGGQTVWVDNHALAQMQ VSDTDQQLYVNSNGRNDGLFLNAPYRGQGSQLIGMTADYNGQHVQVT KQGQDAYGAQWRLITLNNQQVWVDSRALSTTIMQAMNDNMYVNSSQR TDGLWLNAPYTMSGAKWAGDTRSANGRYVHISKAYSNEVGNTYYLTN LNGQSTWIDKRAFTVTFDQVVALNATIVARQRPDGMFKTAPYGEAGAQ FVDYVTNYNQQTVPVTKQHSDAQGNQWYLATVNGTQYWIDQRSFSPV VTKVVDYQAKIVPRTTRDGVFSGAPYGEVNAKLVNMATAYQNQVVHA TGEYTNASGITWSQFALSGQEDKLWIDKRALQA | |
| Asr mature protein (L. citreum) | DTNSNVAVKQINNTGTNDSGEKKVPVPSTNNDSLKQGTDGFWYDSDGN RVDQKTNQILLTAEQLKKNNEKNLSVISDDTSKKDDENISKQTKIANQQT VDTAKGLTTSNLSDPITGGHYENHNGYFVYIDASGKQVTGLQNIDGNLQ YFDDNGYQVKGSFRDVNGKHIYFDSVTGKASSNVDIVNGKAQGYDAQG NQLKKSYVADSSGQTYYFDGNGQPLIGLQTIDGNLQYFNQQGVQIKGGF QDVNNKRIYFAPNTGNAVANTEIINGKLQGRDANGNQVKNAFSKDVAG NTFYFDANGVMLTGLQTISGKTYYLDEQGHLRKNYAGTFNNQFMYFDA DTGAGKTAIEYQFDQGLVSQSNENTPHNAAKSYDKSSFENVDGYLTADT WYRPTDILKNGDTWTASTETDMRPLLMTWWPDKQTQANYLNFMSSKG LGITTTYTAATSQKTLNDAAFVIQTAIEQQISLKKSTEWLRDAIDSFVKTQ ANWNKQTEDEAFDGLQWLQGGFLAYQDDSHRTPNTDSGNNRKLGRQPI NIDGSKDTTDGKGSEFLLANDIDNSNPIVQAEQLNWLHYLMNFGSITGNN DNANFDGIRVDAVDNVDADLLKIAGDYFKALYGTDKSDANANKHLSIL EDWNGKDPQYVNQQGNAQLTMDYTVTSQFGNSLTHGANNRSNMWYF LDTGYYLNGDLNKKIVDKNRPNSGTLVNRIANSGDTKVIPNYSFVRAHD YDAQDPIRKAMIDHGIIKNMQDTFTFDQLAQGMEFYYKDQENPSGFKKY NDYNLPSAYAMLLTNKDTVPRVYYGDMYLEGGQYMEKGTIYNPVISAL LKARIKYVSGGQTMATDSSGKDLKDGETDLLTSVRFGKGIMTSDQTTTQ DNSQDYKNRGIGVIVGNNPDLKLNNDKTITLHMGKAHKNQLYRALVLS NDSGIDVYDSDDKAPTLRTNDNGDLIFHKTNTFVKQDGTIINYEMKGSLN ALISYLGVWVPVGASDSQDARTVATESSSSNDGSVFHSNAALDSNVIY EGFSNFQAMPTSPEQSTNVVIATKANLFKELGITSFELAPQYRSSGDTNYG GMSFLDSFLNNGYAFTDRYDLGFNKADGNPNPTKYGTDQDLRNAIEAL HKNGMQAIADWVPDQIYALPGKEVVTATRVDERGNQLKDTDFVNLLYV ANTKSSGVDYQAKYGGEFLDKLREEYPSLFKQNQVSTGQPIDASTKIKQ WSAKYMNGTNILHRGAYYVLKDWATNQYFNIAKTNEVFLPLQLQNKD AQTGFISDASGVKYYSISGYQAKDTFIEDGNGNWYYFDKDGYMVRSQQ GENPIRTVETSVNTRNGNYYFMPNGVELRKGFGTDNSGNVYYFDDQGK MVRDKYINDDANNFYHLNVDGTMSRGLFKFDSDTLQYFASNGVQIKDS YAKDSKGNKYYFDSATGNNDTGKAQTWDGNGYYITIDSDANNTIGVNT DYTAYITSSLREDGLFANAPYGVVTKDQNGNDLKWQYINHTKQYEGQQ VQVTRQYTDSKGVSWNLITFAGGDLQGQRLWVDSRALTMTPFKTMNQI SFISYANRNDGLFLNAPYQVKGYQLAGMSNQYKGQQVTIAGVANVSGK DWSLISFNGTQYWIDSQALNTNFTHDMNQKVFVNTTSNLDGLFLNAPYR QPGYKLAGLAKNYNNQTVTVSQQYFDDQGTVWSQVVLGGQTVWVDN HALAQMQVSDTDQQLYVNSNGRNDGLFLNAPYRGQGSQLIGMTADYN GQHVQVTKQGQDAYGAQWRLITLNNQQVWVDSRALSTTIMQAMNDN MYVNSSQRTDGLWLNAPYTMSGAKWAGDTRSANGRYVHISKAYSNEV GNTYYLTNLNGQSTWIDKRAFTVTFDQVVALNATIVARQRPDGMFKTA PYGEAGAQFVDYVTNYNQQTVPVTKQHSDAQGNQWYLATVNGTQYWI DQRSFSPVVTKVVDYQAKIVPRTTRDGVFSGAPYGEVNAKLVNMATAY QNQVVHATGEYTNASGITWSQFALSGQEDKLWIDKRALQA | 3 |

TABLE 1-continued

Sequences of wild-type enzymes

| Type | Sequence | SEQ ID NO: |
|---|---|---|
| dsrI coding sequence (*L. mesenteroides*) | ATGAGAAATAGAAATGCAACAAGCGTTTTCCGGAAAAAGATGTATAA ATCTGGGAAAATGTTAGTCATTGCAGGGAGTGTTTCAATAATTGGTGT TACCAGTTTTATTCAACAAGCACAAGCTGATGTTTCACAAAACAATGG GGTAGTAGTGGCCACGGCAGTCGATCAATCGAATTTGGATGCGACTA CGTCTGACAAATCAATCACAACAGATGATAAAGCTGCAACAACAGCA GCTACATCAACAGATGATAAGGCTACAACAACAGTAGCTACATCAAC AGATGATAAGGATACAACAACAGCAGCTACATCAACAGATGATAAG GCTACAACAACAGTAGCTACATCAACAGATGATAAGGCTACAACAAC AGCAGCTACATCAACAGATGATAAAGCTGCAACAACAGCAGCTACAT CAACGGATGATAAAGCTGCAACAACAGCAGCTACATCAACGGATGAT AAAGCTGCAACAACAGCAGATACATCAACAGATGATAAAGCTGCAAC AACAGCAGCTACATCAACAGATGATAAGGCTACAACAACAGCAGCTA CATCAACAGATGATAAAACAGCAACAACAGTCGGCACATCTGATAAT AACAATTCAGCTACAGCGAGCGATAAAGATGTAAGTTCATCGGCACA AAAAAGTCAAACGATTGATAACAATTCGAAGACGGCCGATACTACTG CAGCATTAGAAGCTAGTTCAAAGAATCTGAAAACGATTGATGGCAAA ACATATTATTACGACGATGATGATCAAGTAAAAAAGAACTTTGCTAC CGTAATTGATGGTAAGGTACTTTATTTTGATAAAGAGACTGGCGCATT AGCTGATACAAATGACTATCAATTTTTAGAAGGATTGACTAGTGAAA ATAATACTTATACGGAGCATAATGCCTCAGTTGGTACATCTTCTGATA GTTATACAAACGTTGACGGGTACCTAACAGCCGACAGTTGGTACAGG CCTAAGGACATATTAGTCAACGGTCAAAACTGGGAATCATCAAAGGA TGACGATTTACGACCATTGTTAATGACTTGGTGGCCAGATAAGGCAA CACAAGTAAACTATTTGAATGCGATGAAGTATTTAGATGCCACTGAA ACGGAAACTGTTTATACTTCAGATGACAGTCAAGACGCTTTGAACAA AGCAGCACAGAACATTCAAGTGAAAATTGAAGAAAAAATTAGTCAA GAAGGCCAAACACAATGGCTAAAGGATGATATTTCAAAATTTGTTGA TAGCCAATCAAATTGGAATATTGCTAGTGAATCAAAAGGAACTGATC ATTTGCAAGGTGGTGCATTGTTGTATGTCAATAGTGATAAAACACCAG ATGCCAATTCTGATTATCGATTACTTAATCGCACACCAACAAATCAAA CAGGCACGCCTTTGTATACGACAGATCCAACTCAAGGTGGTTATGACT TCCTCTTGGCCAATGATGTGGATAATTCAAACCCAGTTGTTCAAGCAG AACAACTAAATTGGATGTATTACTTGTTAAACTTTGGATCAATTACTA ATAACGATGCAGATGCTAACTTTGATAGTATTCGAGTAGATGCTGTTG ATAACGTTGATGCCGACTTATTGCAAATTGCAGCTGATTATTTCAAGG CAGCATATGGCGTCGATAAGAGTGATGCAATTTCGAATCAACATGTTT CCATTCTTGAAGATTGGAGTGACAATGATGCTGAATATGTGAAAGAC AATGGCGACAATCAATTGTCAATGGATAATAAATTGCGTTTGTCATTA AAATACTCACTCACTATGCCAGCAGTCGATCAATATGGTAATAAAAG AAGTGGATTAGAACCTTTTTTGACAAATAGTTTAGTTGATCGTACAAA TGATTCGACAGATAATACCGCACAACCAAATTATTCTTTTGTTCGTGC ACATGATAGTGAAGTACAAACAGTTATTGCTGAAATTATTAAACAAA GAATTGATCCGGATTCTGATGGCTTATCACCAACGATGGACCAATTAA CAGAAGCGTTTAAAATTTATAATGCTGATCAGTTGAAAACGGATAAA GAATTCACACAATATAACATTCCAAGTACTTATGCCACAATACTAACG AATAAAGATACAGTGCCACGTGTGTACTATGGTGATATGTATACAGA TGATGGTCAATACATGGCAACAAAGTCACTTTATTACGATGCAATTGA TACTTTGCTGAAGTCTCGTATCAAGTATGTTTCTGGCGGGCAAACAAT GTCTATGAAATATATGCAAGGTGATAGTAGTATGGCTGCTGACAGTT ATAGAGGCATTTTGACATCAGTTCGTTATGGTAATGGTGCCATGACTG CTACCGATGCAGGGACAAATGAAACACGTACGCAAGGTATTGCAGTA ATTGAAAGTAATAACCCAGATTTGAAGTTGAGCAGTACAGATCAAGT AGTTGTAGATATGGGCATAGCGCACAAAAACCAGGCTTATCGTCCTG CTTTGTTAACAACTAAAGATGGCATAGATACTTATGTATCTGATAGTG ATGTCTCACAAAGCTTAATAAGATATACAAATAGTAATGGGCAACTT ATTTTCAATAGTTCAGATATTGTTGGTACAGCAAATCCACAAGTTTCT GGATACTTGGCTGTCTGGGTACCCGTTGGTGCTTCAGATACTCAAGAT GCGCGAACTGAAAGTAGTACAGCAACAACTGCTGATGGACAAACATT ACATTCAAATGCCGCACTTGATTCTCAAGTTATTTATGAAAGTTTCTC TAACTTCCAATCTACACCAACAACAGAAGCTGAATATGCTAATGTGC AAATTGCAAACAATACTGATTTATACAAGAGTTGGGGAATTACGAAC TTCGAGTTTCCACCACAATATCGTTCAAGTACGGATAGTAGTTTCTTA GATTCAATTATTCAAATGGTTATGCATTTACTGATCGTTATGATCTT GGATTCAATACACCAACGAAGTATGGTACTGTAGATCAACTCCGTAC AGCTATTAAAGCTTTGCATGCGACAGGTATCAAGGCAATGGCAGATT GGGTACCAGACCAGATTTATAATTTGCAGGTAAAGAAGTGGTTGCG GTACAACGTGTCAACAACTCAGGAATCTATAATCAAGATTCTGTAATT AATAAAACATTATATGCTTCACAAACCGTTGGTGGCGGAGAATATCA GGCACTATATGGTGGAGAGTTCCTTGATGAAATCAAGAAATTGTACC CTTCTCTATTCGAAAAAAATCAAATTTCAACCGGCGTACCAATGGATG CTAGTGAAAAGATAAAGAATGGTCCGCTAAGTACTTTAACGGTACT AACATTCAAGGTCGTGGTGCTTACTATGTCCTTAAGGACTGGGCTACA AATGAGTACTTCAAGGTAAGCACTTCAAGCAACAGCAGTGTATTTTTG CCAAAGCAGTTGACGAATGAAGAATCAAACACTGGATTTATTTCAAC | 4 |

TABLE 1-continued

Sequences of wild-type enzymes

| Type | Sequence | SEQ ID NO: |
|---|---|---|
| | TGATGGTGGGATGACATATTATTCTACAAGTGGATACCAGGCAAAAG<br>ATACATTCATCCAAGATGACAAATCTAATTGGTATTACTTTGACAAGA<br>ATGGTTATATGACATATGGTTTCCAGACAGTCAATGATAATAATTATT<br>ACTTCTTGCCTAATGGTATTGAATTACAAGATGCTATCTTAGAAGATA<br>GTAAAGGAAATGTTTATTATTTCAATCAATATGGCAAACAAGCTGTTG<br>ATGGATACTACATGTTGGCTAATAAAACTTGGCGTTACTTTGACAAAA<br>ATGGTGTTATGGCTAATGCTGGCTTAACAACCGTGACTGTTGATGGGC<br>AGGAGCATATCCAATACTTTGATAAGAACGGTATTCAGGTCAAAGGG<br>ACTTCCGTGAAAGATGCAGACGGAAAGCTACGCTACTTTGACACTGA<br>TTCTGGTGATATGGTGACGAACCGCTTTGGTGAAAACACAGATGGTA<br>CATGGTCATACTTTGGTGCTGACGGTATCGCTGTAACTGGTGCACAGA<br>CAATTAGTGGGCAAAAATTGTTCTTTGATGCCGACGGACAACAGATT<br>AAAGGTAAGGAAGCGACTGATAAAAAAGGCAAAGTGCATTATTATG<br>ATGCTAATTCTGGTGAAATGATCACTAATCGTTTTGAAAAGTTATCAG<br>ATGGATCATGGGCGTACTTTAATAAAAAAGGTAACATCGTAACCGGC<br>GCACAAGTCATTAATGGTCAACATTTGTTCTTTGAAAGCAACGGTAAC<br>CAAGTTAAGGGTCGTGAATACACGGCTACTGATGGGAAGATGCGCTA<br>CTATGATGCAGATTCTGGTGATATGGTGACGAATCGCTTTGAACGAAT<br>ATCAGACGGATCATGGGCATATTTTGGTGCTAATGGTGTTGCTGTAAC<br>TGGGGAACAAAATATAAATGGACAACAACTGTATTTTGATGCCAATG<br>GTCATCAAGTTAAGGGAGCCGCAGTAACACAAGCTGACGGTAGCCAA<br>AAATATTATGACGCAAATTCTGGAGAGATGATTAAAAGCTAA | |
| DsrI protein (L. mesenteroides) | MRNRNATSVFRKKMYKSGKMLVIAGSVSIIGVTSFIQQAQADVSQNN<br>GVVVATAVDQSNLDATTSDKSITTDDKAATTAATSTDDKATTTVATSTD<br>DKDTTTAATSTDDKATTTVATSTDDKATTTAATSTDDKAATTAATSTDD<br>KAATTAATSTDDKAATTADTSTDDKAATTAATSTDDKATTTAATSTDD<br>KTATTVGTSDNNSATASDKDVSSSAQKSQTIDNNSKTADTTAALEASS<br>KNLKTIDGKTYYYDDDDQVKKNFATVIDGKVLYFDKETGALADTNDYQ<br>FLEGLTSENNTYTEHNASVGTSSDSYTNVDGYLTADSWYRPKDILVNGQ<br>NWESSKDDDLRPLLMTWWPDKATQVNYLNAMKYLDATETEVYTSDD<br>SQDALNKAAQNIQVKIEEKISQEGQTQWLKDDISKFVDSQSNWNIASESK<br>GTDHLQGGALLYVNSDKTPDANSDYRLLNRTPTNQTGTPLYTTDPTQGG<br>YDFLLANDVDNSNPVVQAEQLNWMYYLLNFGSITNNDADANFDSIRVD<br>AVDNVDADLLQIAADYFKAAYGVDKSDAISNQHVSILEDWSDNDAEYV<br>KDNGDNQLSMDNKLRLSLKYSLTMPAVDQYGNKRSGLEPFLTNSLVDR<br>TNDSTDNTAQPNYSFVRAHDSEVQTVIAEIIKQRIDPDSDGLSPTMDQLTE<br>AFKIYNADQLKTDKEFTQYNIPSTYATILTNKDTVPRVYYGDMYTDDGQ<br>YMATKSLYYDAIDTLLKSRIKYVSGGQTMSMKYMQGDSSMAADSYRGI<br>LTSVRYGNGAMTATDAGTNETRTQGIAVIESNNPDLKLSSTDQVVVDMG<br>IAHKNQAYRPALLTTKDGIDTYVSDSDVSQSLIRYTNSNGQLIFNSSDIVG<br>TANPQVSGYLAVWVPVGASDTQDARTESSTATTADGQTLHSNAALDSQ<br>VIYESFSNFQSTPTTEAEYANVQIANNTDLYKSWGITNFEFPPQYRSSTDS<br>SFLDSIIQNGYAFTDRYDLGFNTPTKYGTVDQLRTAIKALHATGIKAMAD<br>WVPDQIYNLTGKEVVAVQRVNNSGIYNQDSVINKTLYASQTVGGGEYQ<br>ALYGGEFLDEIKKLYPSLFEKNQISTGVPMDASEKIKEWSAKYFNGTNIQ<br>GRGAYYVLKDWATNEYFKVSTSSNSSVFLPKQLTNEESNTGFISTDGGM<br>TYYSTSGYQAKDTFIQDDKSNWYYFDKNGYMTYGFQTVNDNNYYFLPN<br>GIELQDAILEDSKGNVYYFNQYGKQAVDGYYMLANKTWRYFDKNGVM<br>ANAGLTTVTVDGQEHIQYFDKNGIQVKGTSVKDADGKLRYFDTDSGDM<br>VTNRFGENTDGTWSYFGADGIAVTGAQTISGQKLFFDADGQQIKGKEAT<br>DKKGKVHYYDANSGEMITNRFEKLSDGSWAYFNKKGNIVTGAQVINGQ<br>HLFFESNGNQVKGREYTATDGKMRYYDADSGDMVTNRFERISDGSWAY<br>FGANGVAVTGEQNINGQQLYFDANGHQVKGAAVTQADGSQKYYDANS<br>GEMIKS | 5 |
| DsrI mature protein (L. mesenteroides) | DVSQNNGVVVATAVDQSNLDATTSDKSITTDDKAATTAATSTDDKATT<br>TVATSTDDKDTTTAATSTDDKATTTVATSTDDKATTTAATSTDDKAATT<br>AATSTDDKAATTAATSTDDKAATTADTSTDDKAATTAATSTDDKATTT<br>AATSTDDKTATTVGTSDNNSATASDKDVSSSAQKSQTIDNNSKTADTT<br>AALEASSKNLKTIDGKTYYYDDDDQVKKNFATVIDGKVLYFDKETGAL<br>ADTNDYQFLEGLTSENNTYTEHNASVGTSSDSYTNVDGYLTADSWYRP<br>KDILVNGQNWESSKDDDLRPLLMTWWPDKATQVNYLNAMKYLDATET<br>ETVYTSDDSQDALNKAAQNIQVKIEEKISQEGQTQWLKDDISKFVDSQSN<br>WNIASESKGTDHLQGGALLYVNSDKTPDANSDYRLLNRTPTNQTGTPLY<br>TTDPTQGGYDFLLANDVDNSNPVVQAEQLNWMYYLLNFGSITNNDADA<br>NFDSIRVDAVDNVDADLLQIAADYFKAAYGVDKSDAISNQHVSILEDWS<br>DNDAEYVKDNGDNQLSMDNKLRLSLKYSLTMPAVDQYGNKRSGLEPFL<br>TNSLVDRTNDSTDNTAQPNYSFVRAHDSEVQTVIAEIIKQRIDPDSDGLSP<br>TMDQLTEAFKIYNADQLKTDKEFTQYNIPSTYATILTNKDTVPRVYYGD<br>MYTDDGQYMATKSLYYDAIDTLLKSRIKYVSGGQTMSMKYMQGDSSM<br>AADSYRGILTSVRYGNGAMTATDAGTNETRTQGIAVIESNNPDLKLSSTD<br>QVVVDMGIAHKNQAYRPALLTTKDGIDTYVSDSDVSQSLIRYTNSNGQL<br>IFNSSDIVGTANPQVSGYLAVWVPVGASDTQDARTESSTATTADGQTLH<br>SNAALDSQVIYESFSNFQSTPTTEAEYANVQIANNTDLYKSWGITNFEFPP | 6 |

TABLE 1-continued

Sequences of wild-type enzymes

| Type | Sequence | SEQ ID NO: |
|------|----------|------------|
| | QYRSSTDSSFLDSIIQNGYAFTDRYDLGFNTPTKYGTVDQLRTAIKALHA<br>TGIKAMADWVPDQIYNLTGKEVVAVQRVNNSGIYNQDSVINKTLYASQ<br>TVGGGEYQALYGGEFLDEIKKLYPSLFEKNQISTGVPMDASEKIKEWSAK<br>YFNGTNIQGRGAYYVLKDWATNEYFKVSTSSNSSVFLPKQLTNEESNTG<br>FISTDGGMTYYSTSGYQAKDTFIQDDKSNWYYFDKNGYMTYGFQTVND<br>NNYYFLPNGIELQDAILEDSKGNVYYFNQYGKQAVDGYYMLANKTWR<br>YFDKNGVMANAGLTTVTVDGQEHIQYFDKNGIQVKGTSVKDADGKLR<br>YFDTDSGDMVTNRFGENTDGTWSYFGADGIAVTGAQTISGQKLFFDAD<br>GQQIKGKEATDKKGKVHYYDANSGEMITNRFEKLSDGSWAYFNKKGNI<br>VTGAQVINGQHLFFESNGNQVKGREYTATDGKMRYYDADSGDMVTNR<br>FERISDGSWAYFGANGVAVTGEQNINGQQLYFDANGHQVKGAAVTQAD<br>GSQKYYDANSGEMIKS | |
| dsrS coding sequence (L. mesenteroides) | ATGCCATTTACAGAAAAAGTAATGCGGAAAAAGCTTTATAAAGTTGG<br>GAAAAGTTGGGTAGTTGGTGGGGTTTGTGCTTTTGCATTAACCGCCTC<br>ATTTGCTTTAGCAACACCAAGTGTTTTGGGAGACAGTAGTGTACCTGA<br>TGTGAGTGCGAATAACGTTCAATCTGCTTCAGATAATACAACGGATA<br>CGCAGCAGAACACTACGGTTACCGAAGAAAATGATAAAGTACAGTCT<br>GCAGCTACTAATGATAATGTAACAACAGCTGCAAGCGACACAACGCA<br>ATCTGCTGATAATAATGTGACAGAAAAACAGTCAGATGATCATGCAC<br>TTGATAATGAAAAAGTCGATAACAAACAAGATGAAGTCGCTCAAACC<br>AATGTTACTAGCAAAGATGAGGAATCAGCAGTTGCTTCAACTGACAC<br>TGATCCTGCTGAAACGACAACTGACGAAACACAACAAGTTAGCGGCA<br>AGTACGTTGAAAAAGACGGTAGTTGGTATTATTATTTTGATGATGGCA<br>AAAATGCTAAAGGTTTATCAACGATAGACAACAATATTCAATATTTTG<br>ACGAGAGTGGTAAACAAGTCAAAGGACAGTATGTCACAATTGATAAT<br>CAAACATATTATTTTGATAAGGACTCAGGTGATGAGTTAACTGGTCTG<br>CAAAGCATTGATGGGAACATAGTTGCTTTTAACGATGAAGGGCAACA<br>AATTTTTAATCAATATTACCAATCTGAAAATGGTACAACATACTATTT<br>TGATGATAAAGGACATGCTGCTACCGGTATTAAGAATATCGAAGGCA<br>AAAATTATTATTTTGATAATCTTGGCAACTAAAAAAAGGCTTCTCTG<br>GTGTGATTGATGGTCAAATAATGACATTTGATCAGGAAACAGGGCAA<br>GAAGTTTCTAACACAACTTCTGAAATAAAAGAAGGTTTGACGACACA<br>AAACACGGATTATAGCGAACATAATGCAGCCCACGGTACGGATGCTG<br>AGGACTTTGAAAATATTGACGGCTATTTAACAGCTAGTTCATGGTATC<br>GTCCAACAGATATTTTACGTAACGGAACAGACTGGGAACCTTCTACA<br>GATACAGATTTCAGACCAATATTGTCAGTGTGGTGGCCAGATAAGAA<br>CACCCAGGTCAACTATTTAAATTACATGGCTGATTTAGGGTTTATCAG<br>TAATGCGGACAGTTTTGAAACTGGGGATAGCCAAAGCTTATTAAATG<br>AAGCAAGTAACTATGTTCAAAAATCAATTGAAATGAAAATTAGTGCG<br>CAACAAAGTACAGAGTGGTTAAAGGATGCAATGGCGGCCTTCATTGT<br>CACGCAACCACAGTGGAATGAAACTAGTGAAGATATGAGCAATGACC<br>ATTTACAAAATGGCGCATTAACTTATGTCAACAGTCCACTGACACCTG<br>ATGCTAATTCAAACTTTAGACTACTTAATCGGACACCAACAAACCAG<br>ACTGGTGAACAAGCGTATAATTTAGATAATTCAAAAGGTGGTTTTGA<br>ATTGTTGTTAGCCAATGACGTTGATAATTCAAACCCTGTAGTACAAGC<br>AGAACAATTGAATTGGTTATATTATTTAATGAATTTTGGTACGATTAC<br>GGCCAACGACGCGGATGCTAATTTTGATGGTATTCGTGTAGATGCAGT<br>CGACAATGTGGATGCTGATTTGTTACAAATTGCTGCCGATTATTTCAA<br>ACTAGTTACGTGTTGATCAAAATGATGCTACTGCTAATCAGCATCT<br>TTCAATTTTGGAAGATTGGAGTCACAATGATCCTTTGTATGTAACAGA<br>TCAAGGAAGCAATCAATTAACCATGGATGATTATGTGCACACACAAT<br>TAATCTGGTCTCTAACAAAATCATCTGACATACGAGGTACAATGCAG<br>CGCTTCGTGGATTATTATATGGTTGATCGATCTAATGATAGTACAGAA<br>AACGAAGCCATTCCTAATTACAGCTTTGTACGTGCACACGACAGCGA<br>AGTGCAAACGGTTATTGCCCAAATTGTTTCCGATTTGTATCCTGATGT<br>TGAAAATAGTTTAGCACCAACAACAGAACAATTGGCAGCTGCTTTCA<br>AAGTATACAATGAAGATGAAAAATTAGCAGACAAAAAGTACACACA<br>ATATAATATGGCTAGTGCTTATGCGATGTTGCTAACCAATAAGGATAC<br>TGTTCCTCGTGTCTATTATGGCGATTTATATACAGATGATGGTCAATA<br>TATGGCAACAAAGTCACCATACTATGATGCGATTAACACTTTGCTGAA<br>GGCTAGAGTCCAATATGTTGCTGGTGGCCAATCGATGTCCGTTGATAG<br>TAATGACGTGTTAACAAGTGTTCGCTATGGTAAAGATGCCATGACGG<br>CTTCTGACACTGGAACATCTGAGACGCGTACTGAAGGTGTTGGGGTC<br>ATCGTCAGCAACAACGCGGAACTACAATTAGAGGATGGGCATACAGT<br>CACATTGCACATGGGGCAGCTCATAAGAACCAAGCTTATCGTGCTTT<br>GTTATCAACAACTGCAGATGGATTAGCTTATTATGATACTGATGAAAA<br>TGCACCTGTGGCGTACACAGATGCTAACGGCGATTTGATTTTTACGAA<br>TGAATCAATTTATGGTGTACAAAATCCACAAGTTTCTGGTTACTTGGC<br>AGTTTGGGTTCCGGTAGGTGCGCAACAAGATCAAGATGCACGACGG<br>CCTCTGATACAACAACAAACACGAGTGATAAAGTGTTCCATTCAAAC<br>GCTGCTCTTGATTCTCAAGTCATCTACGAAGGTTTCTCAAACTTCCAA<br>GCATTTGCTACAGACAGCAGTGAATATACAAACGTAGTCATCGCTCA<br>GAATGCGGACCAATTTAAGCAATGGGGTGTGACAAGCTTCCAATTGG<br>CACCACAATATCGTTCAAGTACAGATACAAGTTTCTTGGATTCAATTA | 7 |

TABLE 1-continued

Sequences of wild-type enzymes

| Type | Sequence | SEQ ID NO: |
|---|---|---|
| | TTCAAAACGGGTATGCATTCACGGATCGTTATGACTTAGGTTATGGCA<br>CACCGACAAAATATGGAACTGCTGATCAGTTGCGCGATGCTATTAAA<br>GCCTTACATGCTAGCGGTATTCAAGCCATTGCCGATTGGGTGCCGGAC<br>CAAATTTATAATTTGCCAGAGCAAGAATTAGCTACTGTCACAAGAAC<br>AAATTCATTTGGAGATGACGATACAGATTCTGATATTGACAATGCCTT<br>ATATGTTGTACAAAGTCGTGGGGGTGGTCAATATCAAGAGATGTATG<br>GTGGTGCCTTCTTAGAAGAGTTACAGGCACTCTATCCATCCCTATTTA<br>AAGTGAATCAAATCTCAACTGGCGTTCCAATTGATGGCAGTGTAAAG<br>ATTACTGAGTGGGCGGCTAAGTACTTCAATGGCTCTAACATCCAAGGT<br>AAAGGTGCTGGATACGTATTGAAAGATATGGGTTCTAATAAGTATTTT<br>AAGGTCGTTTCGAACACTGAAGATGGTGACTACTTACCAAACAGTT<br>AACTAATGATCTGTCAGAAACTGGCTTTACACACGATGATAAAGGAA<br>TCATCTATTATACATTAAGTGGTTATCGTGCCCAAAATGCATTTATTC<br>AAGATGATGATAATAACTATTACTATTTTGATAAAACAGGTCATTTAG<br>TAACAGGTTTGCAAAAGATTAATAACCATACCTACTTCTTCTTACCTA<br>ATGGTATCGAACTGGTCAAGAGCTTCTTACAAAACGAAGATGGTACA<br>ATTGTTTATTTCGATAAGAAAGGTCATCAAGTTTTTGACCAATATATA<br>ACTGATCAAAATGGAAATGCGTATTACTTTGATGATGCTGGTGTAATG<br>CTTAAATCAGGGCTTGCAACGATTGATGGACATCAACAGTATTTTGAT<br>CAAAATGGTGTGCAGGTTAAGGATAAGTTTGTGATTGGCACTGATGG<br>TTATAAGTATTACTTTGAACCAGGTAGTGGTAACTTAGCTATCCTACG<br>TTATGTGCAAAACAGTAAGAATCAATGGTTCTATTTTGATGGTAATGG<br>CCATGCTGTCACTGGTTTCCAAACAATTAATGGTAAGAAACAATATTT<br>CTATAATGATGGTCATCAAAGTAAAGGTGAATTCATTGATGCAGACG<br>GTGATACTTTCTATACGAGTGCCACTGATGGTCGCCTAGTAACTGGTG<br>TTCAGAAGATTAATGGTATTACCTATGCTTTTGATAACACAGGAAATT<br>TGATCACAAATCAGTATTATCAATTAGCAGATGGTAAATATATGTTGT<br>TAGATGATAGTGGTCGTGCGAAAACAGGGTTTGTATTGCAAGATGGT<br>GTACTAAGATACTTCGATCAAAACGGTGAGCAAGTGAAAGATGCTAT<br>CATTGTGGATCCAGATACTAACTTGAGTTATTATTTCAATGCAACACA<br>AGGTGTCGCTGTAAAAAATGATTATTTCGAGTATCAAGGTAATTGGTA<br>TTTAACAGATGCTAATTATCAACTTATCAAAGGTTTTAAAGCAGTTGA<br>CGACAGCTTACAACATTTTGATGAAGTCACTGGTGTACAAACAAAAG<br>ATAGTGCTTTAATAAGTGCTCAGGGTAAGGTTTACCAATTTGATAATA<br>ATGGAAATGCTGTGTCAGCATAA | |
| DsrS protein<br>(L.<br>mesenteroides) | MPFTEKVMRKKLYKVGKSWVVGGVCAFALTASFALATPSVLGDSSV<br>PDVSANNVQSASDNTTDTQQNTTVTEENDKVQSAATNDNVTTAASDTT<br>QSADNNVTEKQSDDHALDNEKVDNKQDEVAQTNVTSKDEESAVASTDT<br>DPAETTTDETQQVSGKYVEKDGSWYYYFDDGKNAKGLSTIDNNIQYFD<br>ESGKQVKGQYVTIDNQTYYFDKDSGDELTGLQSIDGNIVAFNDEGQQIFN<br>QYYQSENGTTYYFDDKGHAATGIKNIEGKNYYFDNLGQLKKGFSGVIDG<br>QIMTFDQETGQEVSNTTSEIKEGLTTQNTDYSEHNAAHGTDAEDFENIDG<br>YLTASSWYRPTDILRNGTDWEPSTDTDFRPILSVWWPDKNTQVNYLNY<br>MADLGFISNADSFETGDSQSLLNEASNYVQKSIEMKISAQQSTEWLKDA<br>MAAFIVTQPQWNETSEDMSNDHLQNGALTYVNSPLTPDANSNFRLLNRT<br>PTNQTGEQAYNLDNSKGGFELLLANDVDNSNPVVQAEQLNWLYYLMN<br>FGTITANDADANFDGIRVDAVDNVDADLLQIAADYFKLAYGVDQNDAT<br>ANQHLSILEDWSHNDPLYVTDQGSNQLTMDDYVHTQLIWSLTKSSDIRG<br>TMQRFVDYYMVDRSNDSTENEAIPNYSFVRAHDSEVQTVIAQIVSDLYP<br>DVENSLAPTTEQLAAAFKVYNEDEKLADKKYTQYNMASAYAMLLTNK<br>DTVPRVYYGDLYTDDGQYMATKSPYYDAINTLLKARVQYVAGGQSMS<br>VDSNDVLTSVRYGKDAMTASDTGTSETRTEGVGVIVSNNAELQLEDGHT<br>VTLHMGAAHKNQAYRALLSTTADGLAYYDTDENAPVAYTDANGDLIFT<br>NESIYGVQNPQVSGYLAVWVPVGAQQDQDARTASDTTTNTSDKVFHSN<br>AALDSQVIYEGFSNFQAFATDSSEYTNVVIAQNADQFKQWGVTSFQLAP<br>QYRSSTDTSFLDSIIQNGYAFTDRYDLGYGTPTKYGTADQLRDAIKALHA<br>SGIQAIADWVPDQIYNLPEQELATVTRTNSFGDDDTDSDIDNALYVVQSR<br>GGGQYQEMYGGAFLEELQALYPSLFKVNQISTGVPIDGSVKITEWAAKY<br>FNGSNIQGKGAGYVLKDMGSNKYFKVVSNTEDGDYLPKQLTNDLSETG<br>FTHDDKGIIYYTLSGYRAQNAFIQDDDNNYYYFDKTGHLVTGLQKINNH<br>TYFFLPNGIELVKSFLQNEDGTIVYFDKKGHQVFDQYITDQNGNAYYFD<br>DAGVMLKSGLATIDGHQQYFDQNGVQVKDKFVIGTDGYKYYFEPGSGN<br>LAILRYVQNSKNQWFYFDGNGHAVTGFQTINGKKQYFYNDGHQSKGEFI<br>DADGDTFYTSATDGRLVTGVQKINGITYAFDNTGNLITNQYYQLADGKY<br>MLLDDSGRAKTGFVLQDGVLRYFDQNGEQVKDAIIVDPDTNLSYYFNAT<br>QGVAVKNDYFEYQGNWYLTDANYQLIKGFKAVDDSLQHFDEVTGVQT<br>KDSALISAQGKVYQFDNNGNAVSA | 8 |
| DsrS mature<br>protein (L.<br>mesenteroides) | DSSVPDVSANNVQSASDNTTDTQQNTTVTEENDKVQSAATNDNVTTAA<br>SDTTQSADNNVTEKQSDDHALDNEKVDNKQDEVAQTNVTSKDEESAVA<br>STDTDPAETTTDETQQVSGKYVEKDGSWYYYFDDGKNAKGLSTIDNNIQ<br>YFDESGKQVKGQYVTIDNQTYYFDKDSGDELTGLQSIDGNIVAFNDEGQ<br>QIFNQYYQSENGTTYYFDDKGHAATGIKNIEGKNYYFDNLGQLKKGFSG<br>VIDGQIMTFDQETGQEVSNTTSEIKEGLTTQNTDYSEHNAAHGTDAEDFE | 9 |

TABLE 1-continued

Sequences of wild-type enzymes

| Type | Sequence | SEQ ID NO: |
|---|---|---|
| | NIDGYLTASSWYRPTDILRNGTDWEPSTDTDFRPILSVWWPDKNTQVNY LNYMADLGFISNADSFETGDSQSLLNEASNYVQKSIEMKISAQQSTEWLK DAMAAFIVTQPQWNETSEDMSNDHLQNGALTYVNSPLTPDANSNFRLL NRTPTNQTGEQAYNLDNSKGGFELLLANDVDNSNPVVQAEQLNWLYYL MNFGTITANDADANFDGIRVDAVDNVDADLLQIAADYFKLAYGVDQND ATANQHLSILEDWSHNDPLYVTDQGSNQLTMDDYVHTQLIWSLTKSSDI RGTMQRFVDYYMVDRSNDSTENEAIPNYSFVRAHDSEVQTVIAQIVSDL YPDVENSLAPTTEQLAAAFKVYNEDEKLADKKYTQYNMASAYAMLLT NKDTVPRVYYGDLYTDDGQYMATKSPYYDAINTLLKARVQYVAGGQS MSVDSNDVLTSVRYGKDAMTASDTGTSETRTEGVGVIVSNNAELQLED GHTVTLHMGAAHKNQAYRALLSTTADGLAYYDTDENAPVAYTDANGD LIFTNESIYGVQNPQVSGYLAVWVPVGAQQDQDARTASDTTTNTSDKVF HSNAALDSQVIYEGFSNFQAFATDSSEYTNVVIAQNADQFKQWGVTSFQ LAPQYRSSTDTSFLDSIIQNGYAFTDRYDLGYGTPTKYGTADQLRDAIKA LHASGIQAIADWVPDQIYNLPEQELATVTRTNSFGDDDTDSDIDNALYVV QSRGGGQYQEMYGGAFLEELQALYPSLFKVNQISTGVPIDGSVKITEWA AKYFNGSNIQGKGAGYVLKDMGSNKYFKVVSNTEDGDYLPKQLTNDLS ETGFTHDDKGIIYYTLSGYRAQNAFIQDDDNNYYYFDKTGHLVTGLQKI NNHTYFFLPNGIELVKSFLQNEDGTIVYFDKKGHQVFDQYITDQNGNAY YFDDAGVMLKSGLATIDGHQQYFDQNGVQVKDKFVIGTDGYKYYFEPG SGNLAILRYVQNSKNQWFYFDGNGHAVTGFQTINGKKQYFYNDGHQSK GEFIDADGDTFYTSATDGRLVTGVQKINGITYAFDNTGNLITNQYYQLAD GKYMLLDDSGRAKTGFVLQDGVLRYFDQNGEQVKDAIIVDPDTNLSYY FNATQGVAVKNDYFEYQGNWYLTDANYQLIKGFKAVDDSLQHFDEVT GVQTKDSALISAQGKVYQFDNNGNAVSA | |
| gtfI coding sequence (*S. sobrinus*) | ATGGAGAAGAATGTACGTTTTAAGATGCATAAGGTGAAAAAGAGATG GGTAACCCTCTCTGTCGCATCTGCCACCATGTTGGCATCAGCCCTTGG TGCTTCAGTAGCTAGTGCGGATACAGACACTGCTAGTGATAGCA ACCAAACCGTGGTAACTGGTGACCAGACTACTAACAATCAAGCCACT GACCCAGACTTCTATTGCAGCAACAGCTACATCAGAACAGTCTGCTTCA ACTGATGCAGCAACAGATCAAGCATCAGCAGCAGAGCAAACTCAAG GAACAACAGCTAGCACAGACACGGCAGCTCAAACAACCACAAATGCT AATGAAGCTAAGTGGGTTCCGACTGAAAATGAGAACCAAGGTTTTAC AGATGAGATGTTAGCAGAAGCCAAGAATGTGGCTACTGCTGAATCTG ATTCAATTCCATCAGACTTGGCTAAAATGTCAAATGTTAAGCAGGTTG ACGGTAAATATTATTACTACGACCAAGATGGCAATGTTAAGAAAAAC TTTGCTGTCAGCGTTGGTGATAAGATTTATTACTTTGATGAAACTGGC GCTTACAAGGACACTAGCAAGGTTGATGCCGACAAGTCCAGTTCAGC TGTAAGTCAAAATGCAACAATATTTGCAGCTAATAACCGTGCCTACA GCACCTCAGCTAAAAATTTTGAAGCCGTTGATAACTACCTGACAGCTG ACTCTTGGTATCGTCCAAAATCAATCCTGAAAGACGGAAAAACTTGG ACAGAATCTGGCAAAGATGACTTCCGCCCGCTTCTCATGGCTTGGTGG CCTGATACCGAAACCAAACGTAACTACGTTAATTACATGAACAAGGT TGTTGGTATTGATAAGACCTATACCGCTGAAACCAGCCAAGCTGATTT AACGGCAGCAGCAGAATTGGTTCAAGCTCGTATTGAACAAAAAATTA CAAGTGAAAATAACACTAAGTGGCTCCGTGAGGCGATTTCTGCCTTTG TGAAAACTCAGCCGCAATGGAATGGTGAAAGCGAAAAGCCTTACGAT GATCACTTGCAAAATGGTGCTCTTCTCTTTGACAATCAAACTGATTTA ACACCAGATACGCAATCGAACTATCGTTTGCTCAATCGCACACCAACT AACCAAACTGGTTCCTTGGATTCTCGTTTCACCTATAACCCAAATGAC CCACTGGGCGGCTATGATTTCCTTTTAGCCAACGATGTTGATAATTCC AATCCAGTCGTGCAAGCGGAACAACTCAACTGGCTGCACTACCTGCT CAACTTTGGCTCTATCTATGCCAATGATGCAGATGCCAATTTTGACTC AATCCGTGTAGATGCGGTTGATAATGTTGATGCTGACCTTCTGCAAAT CTCTAGTGATTACCTTAAGGCAGCTTACGGTATCGATAAAAACAACA AAAATGCTAATAACCACGTTTCTATCGTAGAAGCATGGAGCGACAAC GATACCCCTTATCTCCATGATGATGGCGACAACCTCATGAACATGGAC AACAAGTTCCGTTTGTCCATGCTTTGGTCTTTAGCTAAGCCAACCGAT GTTCGTTCTGGTTTGAATCCTTTGATCCACAACAGTCTGGTTGACCGT GAAGTGGATGACCGTGAAGTGAAACCGTTCCAAGTTACAGCTTTGC TCGGGCTCATGATAGTGAAGTTCAGGATATCATTCGTGATATTATTAA GGCTGAGATTAATCCAAATTCATTTGGTTATTCATTCACCCAAGAAGA AATTGATCAAGCTTTCAAGATTTACAACGAAGATCTCAAGAAGACTG ATAAAAAATACACTCACTACAATGTGCCGCTTTCTTATACCTTGCTTC TGACTAACAAGGGTTCGATTCCTCGCGTCTATTATGGAGATATGTTCA CCGATGATGGTCAATACATGGCCAACAAGACTGTGAACTACGATGCT ATCGAATCTCTGCTGAAAGCCCGTATGAAGTACGTTGCTGGTGGTCAG GCTATGCAGAATTACCAAATCGGTAATGGCGAAATCTTGACTTCTGTC CGTTATGGTAAGGGTGCCCTTAAACAAAGCGATAAGGGTGACGAC AACTCGTACGTCAGGTGTCGGCGTTGTTATGGGAAACCAACCCAACTT TAGCTTGGATGGAAAGGTTGTAGCCCTCAACATGGGTGCTGCCCACG CTAACCAAGAATACCGTGCTCTTATGGTATCAACTAAAGACGGTGTTG CAACCTATGCTACAGATGCTGATGCTAGCAAGGCTGGTCTGGTTAAG CGCACAGATGAAAATGGTTACCTCTACTTCTTGAACGACGATCTCAAG | 10 |

TABLE 1-continued

Sequences of wild-type enzymes

| Type | Sequence | SEQ ID NO: |
|---|---|---|
| | GGGGTTGCTAACCCTCAGGTTTCTGGTTTCCTTCAAGTCTGGGTACCA<br>GTGGGAGCAGCAGATGACCAAGATATTCGTGTAGCAGCTAGCGATAC<br>AGCAAGTACCGATGGAAAATCACTCCATCAAGATGCTGCCATGGACT<br>CTCGCGTCATGTTTGAAGGTTTCTCTAACTTCCAATCTTTTGCGACAA<br>AAGAAGAAGAGTATACCAATGTTGTCATTGCTAACAATGTTGATAAA<br>TTTGTTTCATGGGGAATCACTGACTTTGAAATGGCTCCTCAGTATGTC<br>TCATCTACTGACGGTCAGTTCCTTGATTCTGTCATTCAAAATGGTTAT<br>GCCTTTACCGACCGTTATGACTTGGGTATGTCTAAAGCAAACAAGTAT<br>GGTACAGCCGACCAATTGGTTAAGGCTATCAAGGCTCTCCATGCTAA<br>GGGCCTGAAGGTTATGGCAGACTGGGTTCCAGACCAAATGTACACCT<br>TCCCTAAACAAGAAGTGGTCACTGTTACTCGGACAGATAAGTTTGGC<br>AAACCAATCGCAGGAAGCCAAATTAATCACAGTCTCTACGTAACAGA<br>TACAAAGAGCTCTGGTGATGACTATCAAGCTAAATACGGCGGTGCCT<br>TCCTTGACGAATTAAAGGAAAAATATCCAGAACTCTTCACCAAGAAG<br>CAAATGTCTACTGGTCAGGCGATTGATCCATCTGTTAAGATTAAACAA<br>TGGTCTGCTAAGTACTTTAATGAAGTAATATTCTTGGCCGGGGTGCC<br>GATTATGTCCTCAGCGACCAAGTCAGCAACAAGTACTTCAACGTTGCC<br>AGCGATACACTCTTCTTACCAAGCAGCTTACTCGGCAAGGTCGTAGA<br>GTCTGGTATTCGTTATGATGGTAAGGGTTATATTTATAACTCAAGTGC<br>AACTGGTGACCAAGTCAAAGCAAGCTTCATTACCGAAGCAGGCAATC<br>TATACTACTTCGGTAAAGACGGTTATATGGTGACTGGCGCTCAAACCA<br>TTAATGGTGCTAACTATTCTTCCTTGAAAATGGTACGGCTCTTCGCA<br>ACACTATTTATACAGATGCTCAAGGCAATAGCCATTACTACGCAAAT<br>GACGGTAAACGCTATGAAAATGGTTACCAACAATTTGGTAATGACTG<br>GCGTTACTTCAAGGACGGTAACATGGCTGTTGGCTTGACAACTGTTGA<br>TGGCAATGTTCAATACTTTGATAAAGATGGTGTTCAAGCTAAGGATA<br>AGATTATTGTCACCCGTGATGGTAAGGTTCGTTACTTTGACCAACATA<br>ATGGAAATGCTGTAACCAATACCTTCATCGCTGACAAGACTGGTCACT<br>GGTACTATCTAGGTAAAGATGGTGTCGCTGTTACCGGTGCTCAAACCG<br>TTGGGAAACAAAAACTTTACTTTGAAGCAAACGGTCAACAAGTTAAG<br>GGTGACTTCGTAACTTCTGACGAAGGTAAACTTTACTTCTACGATGTC<br>GATTCAGGTGACATGTGGACTGATACCTTCATTGAAGATAAGGCAGG<br>CAATTGGTTCTACCTTGGTAAAGATGGTGCAGCTGTGACTGGTGCTCA<br>AACTATTCGTGGCCAAAAACTTTACTTCAAGGCTAACGGCCAACAAG<br>TCAAGGGAGATATCGTCAAGGGTACTGATGGTAAGATCCGTTACTAC<br>GACGCTAAATCTGGTGAACAAGTCTTCAACAAGACTGTTAAGGCCGC<br>TGATGGCAAGACCTATGTTATCGGAAATGATGGTGTTGCAGTTGATCC<br>AAGCGTTGTCAAAGGACAAACCTTCAAGGATGCTTCAGGTGCTCTTC<br>GTTTCTATAACCTCAAAGGACAACTGGTAACAGGCAGCGGTTGGTAT<br>GAAACTGCAAATCACGATTGGGTTTATATCCAATCTGGTAAAGCCTTG<br>ACTGGGGAACAGACCCATCAATGGTCAACATCTTTACTTCAAGAAAGA<br>TGGACATCAAGTCAAAGGACAACTGGTAACAGGAACTGATGGTAAGG<br>TTCGCTATTATGATGCAAATTCAGGCGACCAAGCCTTCAACAAGTCTG<br>TAACAGTTAACGGTAAGACTTACTACTTCGGTAATGATGGCACTGCTC<br>AAACAGCGGGAAACCCTAAGGGACAAACCTTCAAAGATGGTTCAGAT<br>ATCCGCTTTTACAGCATGGAAGGCCAATTAGTGACTGGCAGTGGTTG<br>GTACTCAAACGCACAAGGTCAGTGGCTTTATGTCAAAAATGGTAAAG<br>TCTTGACAGGCCTGCAAACAGTTGGTAGCCAACGTGTTTACTTTGACG<br>AAAATGGTATTCAAGCTAAAGGTAAAGCAGTAAGGACTTCCGACGGT<br>AAGATACGCTACTTCGATGAAAATTCAGGTAGCATGATTACCAACCA<br>ATGGAAAGAGGTTAACGGTCGATATTATTACTTCGGTAATGATGGCG<br>CAGCTATCTACCGTGGCTGGAACTAA | |
| Gtfl protein<br>(S. sobrinus) | MEKNVRFKMHKVKKRWVTLSVASATMLASALGASVASADTDTASD<br>DSNQTVVTGDQTTNNQATDQTSIAATATSEQSASTDAATDQASAAEQTQ<br>GTTASTDTAAQTTTNANEAKWVPTENENQGFTDEMLAEAKNVATAESD<br>SIPSDLAKMSNVKQVDGKYYYYDQDGNVKKNFAVSVGDKIYYFDETGA<br>YKDTSKVDADKSSSAVSQNATIFAANNRAYSTSAKNFEAVDNYLTADS<br>WYRPKSILKDGKTWTESGKDDFRPLLMAWWPDTETKRNYVNYMNKVV<br>GIDKTYTAETSQADLTAAAELVQARIEQKITSENNTKWLREAISAFVKTQ<br>PQWNGESEKPYDDHLQNGALLFDNQTDLTPDTQSNYRLLNRTPTNQTGS<br>LDSRFTYNPNDPLGGYDFLLANDVDNSNPVVQAEQLNWLHYLLNFGSIY<br>ANDADANFDSIRVDAVDNVDADLLQISSDYLKAAYGIDKNNKNANNHV<br>SIVEAWSDNDTPYLHDDGDNLMNMDNKFRLSMLWSLAKPTDVRSGLNPLI<br>HNSLVDREVDDREVETVPSYSFARAHDSEVQDIIRDIIKAEINPNSFGYS<br>FTQEEIDQAFKIYNEDLKKTDKKYTHYNVPLSYTLLLTNKGSIPRVYYGD<br>MFTDDGQYMANKTVNYDAIESLLKARMKYVAGGQAMQNYQIGNGEIL<br>TSVRYGKGALKQSDKGDATTRTSGVGVVMGNQPNFSLDGKVVALNMG<br>AAHANQEYRALMVSTKDGVATYATDADASKAGLVKRTDENGYLYFLN<br>DDLKGVANPQVSGFLQVWVPVGAADDQDIRVAASDTASTDGKSLHQD<br>AAMDSRVMFEGFSNFQSFATKEEEYTNVVIANNVDKFVSWGITDFEMAP<br>QYVSSTDGQFLDSVIQNGYAFTDRYDLGMSKANKYGTADQLVKAIKAL<br>HAKGLKVMADWVPDQMYTFPKQEVVTVTRTDKFGKPIAGSQINHSLYV<br>TDTKSSGDDYQAKYGGAFLDELKEKYPELFTKKQMSTGQAIDPSVKIKQ<br>WSAKYFNGSNILGRGADYVLSDQVSNKYFNVASDTLFLPSSLLGKVVES | 11 |

TABLE 1-continued

Sequences of wild-type enzymes

| Type | Sequence | SEQ ID NO: |
|---|---|---|
| | GIRYDGKGYIYNSSATGDQVKASFITEAGNLYYFGKDGYMVTGAQTING ANYFFLENGTALRNTIYTDAQGNSHYYANDGKRYENGYQQFGNDWRY FKDGNMAVGLTTVDGNVQYFDKDGVQAKDKIIVTRDGKVRYFDQHNG NAVTNTFIADKTGHWYYLGKDGVAVTGAQTVGKQKLYFEANGQQVKG DFVTSDEGKLYFYDVDSGDMWTDTFIEDKAGNWFYLGKDGAAVTGAQ TIRGQKLYFKANGQQVKGDIVKGTDGKIRYYDAKSGEQVFNKTVKAAD GKTYVIGNDGVAVDPSVVKGQTFKDASGALRFYNLKGQLVTGSGWYET ANHDWVYIQSGKALTGEQTINGQHLYFKKDGHQVKGQLVTGTDGKVR YYDANSGDQAFNKSVTVNGKTYYFGNDGTAQTAGNPKGQTFKDGSDIR FYSMEGQLVTGSGWYSNAQGQWLYVKNGKVLTGLQTVGSQRVYFDEN GIQAKGKAVRTSDGKIRYFDENSGSMITNQWKEVNGRYYYFGNDGAAI YRGWN | |
| GtfI mature protein (S. sobrinus) | DTDTASDDSNQTVVTGDQTTNNQATDQTSIAATATSEQSASTDAATDQA SAAEQTQGTTASTDTAAQTTTNANEAKWVPTENENQGFTDEMLAEAKN VATAESDSIPSDLAKMSNVKQVDGKYYYYDQDGNVKKNFAVSVGDKIY YFDETGAYKDTSKVDADKSSSAVSQNATIFAANNRAYSTSAKNFEAVDN YLTADSWYRPKSILKDGKTWTESGKDDFRPLLMAWWPDTETKRNYVN YMNKVVGIDKTYTAETSQADLTAAAELVQARIEQKITSENNTKWLREAI SAPFVKTQPQWNGESEKPYDDHLQNGALLFDNQTDLTPDTQSNYRLLNR TPTNQTGSLDSRFTYNPNDPLGGYDFLLANDVDNSNPVVQAEQLNWLH YLLNFGSIYANDADANFDSIRVDAVDNVDADLLQISSDYLKAAYGIDKN NKNANNHVSIVEAWSDNDTPYLHDDGDNLMNMDNKFRLSMLWSLAKP TDVRSGLNPLIHNSLVDREVDDREVETVPSYSFARAHDSEVQDIIRDIIKA EINPNSFGYSFTQEEIDQAFKIYNEDLKKTDKKYTHYNVPLSYTLLLTNK GSIPRVYYGDMFTDDGQYMANKTVNYDAIESLLKARMKYVAGGQAMQ NYQIGNEILTSVRYGKGALKQSDKGDATTRTSGVGVVMGNQPNFSLD GKVVALNMGAAHANQEYRALMVSTKDGVATYATDADASKAGLVKRT DENGYLYFLNDDLKGVANPQVSGFLQVWVPVGAADDQDIRVAASDTAS TDGKSLHQDAAMDSRVMFEGFSNFQSFATKEEEYTNVVIANNVDKFVS WGITDFEMAPQYVSSTDGQFLDSVIQNGYAFTDRYDLGMSKANKYGTA DQLVKAIKALHAKGLKVMADWVPDQMYTFPKQEVVTVTRTDKFGKPIA GSQINHSLYVTDTKSSGDDYQAKYGGAFLDELKEKYPELFTKKQMSTGQ AIDPSVKIKQWSAKYFNGSNILGRGADYVLSDQVSNKYFNVASDTLFLPS SLLGKVVESGIRYDGKGYIYNSSATGDQVKASFITEAGNLYYFGKDGYM VTGAQTINGANYFFLENGTALRNTIYTDAQGNSHYYANDGKRYENGYQ QFGNDWRYFKDGNMAVGLTTVDGNVQYFDKDGVQAKDKIIVTRDGKV RYFDQHNGNAVTNTFIADKTGHWYYLGKDGVAVTGAQTVGKQKLYFE ANGQQVKGDFVTSDEGKLYFYDVDSGDMWTDTFIEDKAGNWFYLGKD GAAVTGAQTIRGQKLYFKANGQQVKGDIVKGTDGKIRYYDAKSGEQVF NKTVKAADGKTYVIGNDGVAVDPSVVKGQTFKDASGALRFYNLKGQL VTGSGWYETANHDWVYIQSGKALTGEQTINGQHLYFKKDGHQVKGQL VTGTDGKVRYYDANSGDQAFNKSVTVNGKTYYFGNDGTAQTAGNPKG QTFKDGSDIRFYSMEGQLVTGSGWYSNAQGQWLYVKNGKVLTGLQTV GSQRVYFDENGIQAKGKAVRTSDGKIRYFDENSGSMITNQWKEVNGRY YYFGNDGAAIYRGWN | 12 |
| gtfG coding sequence (L. pseudo-mesenteroides) | ATGGGAGAGAAAGTCGTGGCGAGAAAGAAGCTTTATAAGGCGAAAA AAAGTTGGGTGGTAGCTGGTTTGACTACTGCCTTTTTGATGGTGAATC AAGCCAGTGTAAGCGCTGATCAAAATGTAAATGATACATCGGTCACA ACACCAACGCAGGATGTCACAACAGATCAGGACACTGGTATTGACGC ATCTGTAACGACGACAGTTAGTCCAAATTTGGATGATACTCAAGTTGA TAACACCAATATTCAGACGTCAACAGATCAAAAAGATGATTCAAAAG GCACCACGCAAACAGTTGAAACGGACGTTACAACGAATAGTCAATCA ACAGACACAACAGCAGTGACAGCTCAAACGAATCAAACAGAAACAA TACAAAATAGTGATGCGACAACTGAAACAGGATTAGTGACAGTTAAT AATCAAGTCAGATACGTTAATCCTGATGGCACAGTTTTGAAAGGCGC ATACAAAACAATTAATGGTAATACCTATTATTTTGATGATAATAGTGG TGACGCACTGATAGGAATACATAAAATTGGAGAATCAATTAAGGGAT TTGGTCTTACTGGTGTCCAAGTCAAAGGAGATTACTTAACGGCAGTCA ACGGTGACAAATATTACTTTGATTCTGACGGTAATACGGTGTCTGGCG TGCAGCAAATTAATGGCAAGACCTATTATTTTGACAGCACTGGTAAAT TAATGAAGGGCTACACAGCAGTCTTGAATGGTGTCGTAACTTTCTTCA ATAGCACAACTGGTAAGCAGATAATACTGATGCCTCAACCATTAAA ACTGGCGTTACAATCGACAACTCGGATTACACAGCTCATAATGCTGCC TATGATAATACAGCCGCCAGCTTTGATAATATCAATGGCTATCTGACG GCAGAAAGTTGGTACAGACCTAAAGAAATATTGGAAAATGGTGAGTC ATGGCGGCCATCTACTGCTGAGGATAAACGTCCCATTTTAATCACTTG GCAACCGGATATTGTGACCGAGGTCAATTATCTCAACATGATGTCTGC AAATGGTTTGCTCTCGATTAACGCACCATTTACAACTGCTAGTGACCT TGCCATTATGAATGATGCTGTCAGAGCTGTTCAAAAGAATATTGAAAT ACGGATTAGCCAAGAAAAATCAACTGATTGGTTAAAAGCGTTGATGA CTCAGTTTATTAATACACAACCGCAGTGGAATGAGGTGAGTGAATCA CCAAGCAATGATCACCTACAAGGCGGTGCATTAACGTATGTCAATAG TCCATTGACGCCAGATGCCAATTCTAATTTTCGTTTGCTTAATCGGAC | 13 |

TABLE 1-continued

Sequences of wild-type enzymes

| Type | Sequence | SEQ ID NO: |
|---|---|---|
| | CCCGACTAATCAATCTGGCACAACGCGTTATGATACTGACAAATCTG<br>AAGGTGGTTTTGAATTATTATTAGCTAATGATGTTGATAATTCAAACC<br>CAGTAGTTCAAGCTGAGCAACTTAACTGGTTGTACTATTTAATGAATT<br>TTGGCTCAATTACAGCTAATGATCCAACGGCTAATTTTGATGGTATTA<br>GAGTTGATGCTGTTGATAACGTAGACGCTGACTTGTTGCAAATTGCAT<br>CGGATTACTTTAAATTAGCGTATGGCACTAGTTTATCTGATACAAATG<br>CTAACCAACATTTATCAATTTTGGAAGATTGGTCTGCTAATGATGCGG<br>AATACATGTCAAAAACGGGTAGTAATCAATTGACAATGGACACGTAT<br>ACGCAGCAACAATTACTCTTTTCATTGACAAAACAAGTTGGTAATCGT<br>GCTGACATGCGACGCTTCCTAGAATACTTTATGATTAATCGTGCCAAC<br>GATTCAACCGAAAATATTGCGACACCAAATTACTCATTTGTTCGTGCA<br>CATGACAGTGAAGTTCAAACGGTCATTGCTACGATAATTAAAGATTT<br>ACATCCTGATGTTGTGAATAGTCTTGCGCCAACTCAAGCACAATTAGA<br>AGAGGCATTTGCCGTGTATAACGCTGATATGAATCGGGTGGATAAAC<br>AATATACCCAATACAATATGCCAAGTGCTTATGCCATGCTTTTGACCA<br>ATAAAGATACGATTCCACGTGTATATTATGGTGATTTATACACAGATG<br>ATGGTGAGTATATGGGTACGCAAACACCCTATTATGATGCTATCGTTA<br>ATCTATTGCAGTCTCGCGTTAAATATGTTGCAGGTGGACAATCCATGG<br>CGGTTGATCAACATGATATTTTAACAAGTGTGCGTTATGGCAAAAATT<br>TGGCTGACGCTAATGCGACATCAGATGATTTAACCAGTATTAACTCAG<br>GCATAGGTGTTATTGTTTCTAATAATCCCAATCTTTCGTTGGCGTCTGG<br>TGAAACCGTCGTGCTCCATATGGGCATTGCACACGCTAATCAAGTTTA<br>TCGTGAGACTTGAGACAACCGACAACGGTATTGCAAATAATACCG<br>ATATTTTTAAAACAACAGACAGTAATGGTGACTTGATTTTCACAGCTT<br>CTGAAATTCATGGGTATAGTAATGTTCAAGTATCAGGCTTTTTATCAG<br>TTTGGGCGCCTAAAGATGCTACGGATAATCAAGATGTACGTACTGCT<br>GCTAGTGAATCGACTTCTAGTGATGGCAATACGCTTCATTCAAATGCT<br>GCCTTAGATTCCAACATAATTTATGAAGGCTTTTCAAACTTTCAATCC<br>ACACCTCAGTCAGAAAGTGAATTTGCAAAGGTCAAAATAGCTGCTAA<br>TGTTAATCTGTTCAAATCTTGGGGTGTCACCAGTTTTCAAATGGCACC<br>TCAATATCGCTCGAGCACCGATACAAGCTTTTTGGATTCCATTATTCA<br>AAATGGTTATGCCTTCACTGACCGTTACGATTTGGGATTTGAAACACC<br>AACGAAGTATGGGACGGACCAGCAATTGCGTGATGCAATTAAAGCAT<br>TGCATGCTAATGGTATACAAGCAATGGCTGACTTTGTGCCAGACCAG<br>ATTTATAATTTGCCTCAAACAGAACTGGTTTCTGTATCACGCACCGAT<br>AGTCTTGGTAATCAGTCAGCCAATTCAAATGCAGCCAATGTATTGTAT<br>GTATCTCATACAGTTGGTGGTGGTGAATATCAAAGCAAGTATGGGGG<br>CGAATTTTTAGCGCTTATTAAGTCTAAATATCCAAGCTTGTTTAAAAC<br>AATTCAGGTTTCGACAGGACTACCAATTGATGATTCAACTAAGATTAA<br>AGAGTGGTCGGCAAAATACTTTAATGGTTCAAATATTCAAGGACGTG<br>GTTTTGGATATGTGCTATCTGATGGTGGCACGCAGAATTACTTTAAAG<br>TGATTTCGAACAGTACAGATGATGACTTTTTGCCTAATCAGCTGACTG<br>GACAACCCACAATGACAGGCTTTGAACAAACAAGTAAGGGTATTGTA<br>TATTACTCTAAGAGTGGTATTCAGGCTAAAAATCAATTCGTCAAAGAT<br>GATGTTTCTGGTAATTACTACTATTTCAATAAGAATGGTCTGATGACA<br>ATTGGCAGTAAGACGATCAATGGTAAAAACTATATGTTCTTGCCAAA<br>CGGCGTAGAGTTACGAGGATCCTTTTTACAAACGGCGGATGGGACCG<br>TCAATTACTATGCGACTAATGGGCACAGGTTAAGGACGCCTATGTG<br>ACTGACACAGAAGGTAATAGTTATTACTTTGATGGTGATGGGGAAAT<br>GGTAACGGGTGCTTATACAGTTGATGGACATGCGCAATATTTTGATGT<br>GAATGGTGTTCAAACCAAAGGGCTATTATTACACTTGACGGTGTGC<br>AACGCTATTATCAAGCTGGGAACGGTAATTTGGCAACGAATCAATAT<br>GTCAGTTACAACAACAGCTGGTACTATGCCAACGCCAAGGGCGAGTT<br>AGTGACTGGTGTTCAAAGTATTAATGGTAACGTTCAATATTTTGCCAG<br>CAATGGGCAACAAATTAAAGGTCAAATTGTTGTGACTGGTAATCAGA<br>AAAGTTATTACGATGCAAACACTGGAAATCTTATCAGAAATGATTTTT<br>TGACACCGGATCAAGGTAAAACTTGGTATTATGCCGATCAAGATGGT<br>AATCTTGTGGTAGGTGTACGGAATATTAATGGACACAATCAATATTTT<br>GATGATAATGGGATACAAATCAAAGACCAAATCATATCAAATGATGG<br>GCAACAATATTATTATCAAGGTGGTAATGGTGATTTAGTCACAAATCG<br>ATATATCAGTTACAATGATAGTTGGTATTACGCCGACGCAACAGGTGT<br>TCTTGTAACAGGTCAACAAATTATCAACGGTGAAACGCAATACTTTA<br>GGACAGATGGTCGCCAAGTCAAGGGCCAAATTATTGCTGATGGTGAT<br>AAACAGCATTATTACGACGCATATTCAGGCAATTTGGTTAAAAATAA<br>TTTTGTCACAGTCGACCAAGGTAAAACTTGGTATTATGCTGATCAAGA<br>TGGGAACCTCTCTTTGGTTGCCCAATAA | |
| GtfG protein (L. pseudomesenteroides) | MGEKVVARKKLYKAKKSWVVAGLTTAFLMVNQASVSADQNVNDTS<br>VTTTTQDVTTDQDTGIDASVTTTVSPNLDDTQVDNTNIQTSTDQKDDSK<br>GTTQTVETDVTTNSQSTDTTAVTAQTNQTETIQNSDATTETGLVTVNNQ<br>VRYVNPDGTVLKGAYKTINGNTYYFDDNSGDALIGIHKIGESIKGFGLTG<br>VQVKGDYLTAVNGDKYYFDSDGNTVSGVQQINGKTYYFDSTGKLMKG<br>YTAVLNGVVTFFNSTTGEADNTDASTIKTGVTIDNSDYTAHNAAYDNTA<br>ASFDNINGYLTAESWYRPKEILENGESWRPSTAEDKRPILITWQPDIVTEV<br>NYLNMMSANGLLSINAPFTTASDLAIMNDAVRAVQKNIEIRISQEKSTDW | 14 |

TABLE 1-continued

Sequences of wild-type enzymes

| Type | Sequence | SEQ ID NO: |
|---|---|---|
| | LKALMTQFINTQPQWNEVSESPSNDHLQGGALTYVNSPLTPDANSNFRL<br>LNRTPTNQSGTTRYDTDKSEGGFELLLANDVDNSNPVVQAEQLNWLYY<br>LMNFGSITANDPTANFDGIRVDAVDNVDADLLQIASDYFKLAYGTSLSD<br>TNANQHLSILEDWSANDAEYMSKTGSNQLTMDTYTQQQLLFSLTKQVG<br>NRADMRRFLEYFMINRANDSTENIATPNYSFVRAHDSEVQTVIATIIKDL<br>HPDVVNSLAPTQAQLEEAFAVYNADMNRVDKQYTQYNMPSAYAMLLT<br>NKDTIPRVYYGDLYTDDGEYMGTQTPYYDAIVNLLQSRVKYVAGGQSM<br>AVDQHDILTSVRYGKNLADANATSDDLTSINSGIGVIVSNNPNLSLASGE<br>TVVLHMGIAHANQVYREILETTDNGIANNTDIFKTTDSNGDLIFTASEIHG<br>YSNVQVSGFLSVWAPKDATDNQDVRTAASESTSSDGNTLHSNAALDSNI<br>IYEGFSNFQSTPQSESEFAKVKIAANVNLFKSWGVTSFQMAPQYRSSTDT<br>SFLDSIIQNGYAFTDRYDLGFETPTKYGTDQQLRDAIKALHANGIQAMAD<br>FVPDQIYNLPQTELVSVSRTDSLGNQSANSNAANVLYVSHTVGGGEYQS<br>KYGGEFLALIKSKYPSLFKTIQVSTGLPIDDSTKIKEWSAKYFNGSNIQGR<br>GFGYVLSDGGTQNYFKVISNSTDDDFLPNQLTGQPTMTGFEQTSKGIVY<br>YSKSGIQAKNQFVKDDVSGNYYYFNKNGLMTIGSKTINGKNYMFLPNG<br>VELRGSFLQTADGTVNYYATNGAQVKDAYVTDTEGNSYYFDGDGEMV<br>TGAYTVDGHAQYFDVNGVQTKGAIITLDGVQRYYQAGNGNLATNQYV<br>SYNNSWYYANAKGELVTGVQSINGNVQYFASNGQQIKGQIVVTGNQKS<br>YYDANTGNLIRNDFLTPDQGKTWYYADQDGNLVVGVRNINGHNQYFD<br>DNGIQIKDQIISNDGQQYYYQGGNGDLVTNRYISYNDSWYYADATGVLV<br>TGQQIINGETQYFRTDGRQVKGQIIADGDKQHYYDAYSGNLVKNNFVTV<br>DQGKTWYYADQDGNLSLVAQ | |
| GtfG mature protein (*L. pseudo-mesenteroides*) | DQNVNDTSVTTTTQDVTTDQDTGIDASVTTTVSPNLDDTQVDNTNIQTS<br>TDQKDDSKGTTQTVETDVTTNSQSTDTTAVTAQTNQTETIQNSDATTET<br>GLVTVNNQVRYVNPDGTVLKGAYKTINGNTYYFDDNSGDALIGIHKIGE<br>SIKGFGLTGVQVKGDYLTAVNGDKYYFDSDGNTVSGVQQINGKTYYFD<br>STGKLMKGYTAVLNGVVTFFNSTTGEADNTDASTIKTGVTIDNSDYTAH<br>NAAYDNTAASFDNINGYLTAESWYRPKEILENGESWRPSTAEDKRPILIT<br>WQPDIVTEVNYLNMMSANGLLSINAPFTTASDLAIMNDAVRAVQKNIEI<br>RISQEKSTDWLKALMTQFINTQPQWNEVSESPSNDHLQGGALTYVNSPL<br>TPDANSNFRLLNRTPTNQSGTTRYDTDKSEGGFELLLANDVDNSNPVVQ<br>AEQLNWLYYLMNFGSITANDPTANFDGIRVDAVDNVDADLLQIASDYFK<br>LAYGTSLSDTNANQHLSILEDWSANDAEYMSKTGSNQLTMDTYTQQQL<br>LFSLTKQVGNRADMRRFLEYFMINRANDSTENIATPNYSFVRAHDSEVQ<br>TVIATIIKDLHPDVVNSLAPTQAQLEEAFAVYNADMNRVDKQYTQYNMP<br>SAYAMLLTNKDTIPRVYYGDLYTDDGEYMGTQTPYYDAIVNLLQSRVK<br>YVAGGQSMAVDQHDILTSVRYGKNLADANATSDDLTSINSGIGVIVSNN<br>PNLSLASGETVVLHMGIAHANQVYREILETTDNGIANNTDIFKTTDSNGD<br>LIFTASEIHGYSNVQVSGFLSVWAPKDATDNQDVRTAASESTSSDGNTLH<br>SNAALDSNIIYEGFSNFQSTPQSESEFAKVKIAANVNLFKSWGVTSFQMA<br>PQYRSSTDTSFLDSIIQNGYAFTDRYDLGFETPTKYGTDQQLRDAIKALH<br>ANGIQAMADFVPDQIYNLPQTELVSVSRTDSLGNQSANSNAANVLYVSH<br>TVGGGEYQSKYGGEFLALIKSKYPSLFKTIQVSTGLPIDDSTKIKEWSAKY<br>FNGSNIQGRGFGYVLSDGGTQNYFKVISNSTDDDFLPNQLTGQPTMTGFE<br>QTSKGIVYYSKSGIQAKNQFVKDDVSGNYYYFNKNGLMTIGSKTINGKN<br>YMFLPNGVELRGSFLQTADGTVNYYATNGAQVKDAYVTDTEGNSYYFD<br>GDGEMVTGAYTVDGHAQYFDVNGVQTKGAIITLDGVQRYYQAGNGNL<br>ATNQYVSYNNSWYYANAKGELVTGVQSINGNVQYFASNGQQIKGQIVV<br>TGNQKSYYDANTGNLIRNDFLTPDQGKTWYYADQDGNLVVGVRNING<br>HNQYFDDNGIQIKDQIISNDGQQYYYQGGNGDLVTNRYISYNDSWYYA<br>DATGVLVTGQQIINGETQYFRTDGRQVKGQIIADGDKQHYYDAYSGNLV<br>KNNFVTVDQGKTWYYADQDGNLSLVAQ | 15 |

In many embodiments, the modified glucansucrase enzymes of the present invention are at least partially purified from a recombinant host cell, or its growth medium. A purified protein or polypeptide of the mutant enzymes of the present invention can be obtained by several methods. The purified protein or polypeptide of the modified glucansucrase of the present invention is preferably produced in pure form (preferably at least about 80%, more preferably 90%, pure) by conventional techniques well known in the art. Typically, the purified protein or polypeptide of the modified glucansucrase of the present invention is secreted into the growth medium of recombinant host cells. Alternatively, the purified protein or polypeptide of the glucansucrase of the present invention is produced but not secreted into growth medium. In such cases, to isolate the protein or polypeptide of the mutant glucansucrase, the host cell carrying a recombinant plasmid is propagated, lysed by any method known in the art (e.g., sonication, heat, or chemical treatment), and the homogenate is centrifuged to remove cell debris. The supernatant is then subjected to immobilized affinity chromatography depending on the affinity tag (e.g., hexahistidine, maltose binding protein, or glutathione-S-transferase). Depending on the application requirements, affinity tags may be removed from the enzyme by enzymatic cleavage and further purified to homogeneity. Alternatively, traditional protein purification methods involving, but not limited to, sequential ammonium precipitation, ion exchange chromatography, hydrophobic interaction chromatography and gel filtration may be used in the purification of the mutant glucansucrase.

Oligosaccharides

Disclosed herein are variant glucansucrase enzymes that produce various products. In general, the variant enzymes produce some amount of at least one oligosaccharide. Of pertinence to the present application, isomelizitose (α-D-glucopyranosyl-(1→6)-β-D-fructofuranosyl-(2↔1)-α-D-glucopyranoside) production, is increased by many variants disclosed herein.

Although several uses for isomelezitose have been proposed, including prebiotics (Görl et al., supra) and pharmaceutical excipients (Backstrom et al, 1999), applications are currently limited due to the high cost and relative scarcity of this compound. Isomelezitose has been isolated in small amounts from several enzymatic reaction mixtures (Chiba et al., supra; Fujii et al., supra; Inohara-Ochiai et al., supra), but only one instance of a high-yielding synthesis has been reported (Görl et al., supra). In that example, the yield was reportedly over 70% from sucrose, but that number was calculated from the amount of sucrose consumed, not from the total sucrose added to the reaction. Because their method gave undesirable side products if the reaction was allowed to proceed to completion, it was halted when only a fraction of the sucrose was consumed. If their yield were calculated on the basis of the amount of sucrose present in the starting mixture, the result would actually be closer to 20-25% yield. This contrasts with yields from several variant enzymes described herein, which are on the order of 40-60% yield from the total sucrose added to the reaction mixture, all of which is consumed in the reaction.

Thus, one aspect of the present invention is the production of isomelezitose and other products using the modified proteins provided herein. Such modified proteins (purified or unpurified) can be exposed to one or more carbohydrate sources as a method of converting the carbohydrate(s) to a desired product (e.g., isomelezitose). In preferred embodiments, the carbohydrate source is sucrose in an aqueous solution, with or without additional components. In such embodiments, the sucrose can be at any desired molar concentration, such as 0.1M, 0.2M, 0.3M, 0.4M, 0.5M, 0.6M, 0.7M, 0.8M, 0.9M, 1.0M, 1.1M, 1.2M, 1.3M, 1.4M, 1.5M, 1.6M, 1.7M, 1.8M, 1.9M, 2.0M, or higher. Such reactions can be performed in reaction solutions under any conditions at which the enzyme(s) exhibit catalytic activity. Standard reaction variables such as pH, temperature and ionic concentration can be readily modified by one of skill in the art. Preferably, reactions are performed at or below 40° C., and more preferably between 20° C. and 35° C. Preferably, the pH of such reactions is between 3.5 and 8.5. Preferably, reactions are performed in the presence of any desirable ion or salt, such as $Ca^{+2}$, $Mg^{+2}$, $Na^+$, $K^+$, etc.

Having generally described this invention, the same will be better understood by reference to certain specific examples, which are included herein to further illustrate the invention and are not intended to limit the scope of the invention as defined by the claims.

EXAMPLES

Example 1

Modifications of Glucansucrases

The glucansucrase gene, dsrI, from *L. mesenteroides* NRRL B-1118 (SEQ ID NO: 4) was previously cloned and expressed in *E. coli* using a small ubiquinone-like modifier (SUMO) fusion tag to improve solubility (Côté and Skory (2012), supra). After removal of the SUMO tag with SUMO protease 1, the purified enzyme is expected to have the same amino acid sequence as the mature full-length protein (SEQ ID NO: 6) without the native dsrI signal peptide (see, Table 1, underlined section of SEQ ID NO: 5), which is normally removed during secretion in the wild-type *L. mesenteroides* host. The lysine residue at position 441 and the threonine residue at position 654 of the full length DsrI protein (SEQ ID NO:5) are equivalent to the lysine and threonine residues at positions 400 and 613 (respectively) of the mature DsrI protein (SEQ ID NO:6) and these residues are typically referred to as "L441" or "T654". Thus, text describing a mutation of L441 in the full-length DsrI also refers to a mutation of L400 in the mature DsrI protein (lacking the signal sequence). Mutations for L441 substitutions (FIG. 1) were introduced into plasmid pSUMO-Dsr403 using a two-stage PCR protocol (Wang and Malcolm, BioTechniques (1999) 26:680-82) followed by DpnI digestion and then transformation into *E. coli* Acella cells (EdgeBio, San Jose, Calif.). Oligonucleotides were used for mutagenesis to amino acid substitutions E, F, W, K, D, Y, N, V, P, T, S, G, I, Q, and R. In addition, we also performed L441P substitutions in pSUMO-Dsr403 T654R and T654Y mutants, which were shown to produce glucan having significantly altered levels of 1,3-disubstituted α-d-glucopyranosyl units compared to native DsrI (Côté and Skory (2014), supra). Expression and purification of the modified enzymes were previously described (Côté and Skory (2012), supra). Mutant forms of DsrI modified only at T654 were produced from *Lactococcus lactis* cultures as previously described (Côté and Skory (2015), supra).

The dextransucrase gene, dsrS, from *L. mesenteroides* NRRL B-1118 (SEQ ID NO: 7) was previously cloned and expressed in *E. coli* using a similar SUMO fusion tag (Côté and Skory (2015), supra). After removal of the SUMO tag with SUMO protease 1, the purified enzyme is expected to have the same amino acid sequence as the mature full-length protein (SEQ ID NO: 9) without the native DsrS signal peptide (see, Table 1, underlined section of SEQ ID NO: 8), which is normally removed during secretion in the wild-type *L. mesenteroides* host. The lysine residue at position 459 of the full length DsrS protein (SEQ ID NO:8) is equivalent to the lysine residue at position 417 of the mature DsrS protein (SEQ ID NO:9) and this residue is typically referred to as "L459". Thus, text describing a mutation of L459 in the full-length DsrS also refers to a mutation of L417 in the mature DsrS protein (lacking the signal sequence). Mutations for L459P substitutions (FIG. 1) were introduced into pDsrS-SUMO using oligonucleotides as previously described. In addition, DsrS (L459P) was also cloned into *L. lactis* for nisin-induced secreted expression of the modified enzyme. This was accomplished through Gibson assembly (Gibson, Young, Chuang, Venter, Hutchison and Smith 2009) of PCR-amplified DsrS(L459P) and the vector portion of pDsrI.3535.usp45 (Côté and Skory (2015), supra). The resultant plasmid pDsrS(L459).3535.usp45 relied on the Usp45 peptidase cleavage site fragment that was designed such that the DsrS(L459P) processed by *L. lactis* should be identical to that secreted by *L. mesenteroides* NRRL B-1118 (SEQ ID NO:9) with the exception of L459P. Transformation into *L. lactis* LM0230 and enzyme production methods were similar to that previously described (Côté and Skory (2015), supra).

The glucosyltransferase gene, gtfI, from *Streptococcus sobrinus* NRRL B-14554 (SEQ ID NO: 10) was PCR amplified and then used for Gibson assembly with PCR-amplified pE-SUMOpro Kan (Life Sensors, Malvern, Pa.). Cleavage of the purified protein from *E. coli* containing the resultant plasmid pGtfI.SUMO with SUMO protease 1 should yield enzyme with the same amino acid sequence as the secreted GtfI protein (SEQ ID NO: 12) from the wild-type *S. sobrinus* host, without the native signal peptide (see, Table 1, underlined section of SEQ ID NO:11). The lysine residue at position 350 of the full length GtfI protein (SEQ ID NO:11) is equivalent to the lysine residue at position 312 of the mature GtfI protein (SEQ ID NO:12) and this residue is typically referred to as "L350", but indicates the same lysine residue. Thus, text describing a mutation of L350 in full-length GtfI also refers to a mutation of L312 in the mature GtfI protein (lacking the signal sequence). Mutations for L350 substitutions (FIG. 1) were introduced into plasmid pGtfI.SUMO using the same methods as before for amino acid substitutions P, S, E, and R.

The alternansucrase gene, asr, from *Leuconostoc citreum* NRRL B-1355 (SEQ ID NO:1) was PCR amplified and used for Gibson assembly with the same pESUMO.Gib PCR fragment previously used. In order to improve solubility of the recombinant enzyme, the sequence was also cloned into the same *L. lactis* expression plasmid previously described. This was accomplished by Gibson assembly of the PCR-amplified asr gene to remove the predicted signal peptide (Arguello-Morales, et al., FEMS Microbiol. Lett., (2000) 182:81-5; see, Table 1, underlined section of SEQ ID NO:2) and the vector portion of pDsrI.3535.usp45 previously used. The resultant plasmid, pAsr.3535.usp45, was further altered by modifying the codon for L544 (FIG. 1) via PCR for amino acid substitutions P, S, E, and R. The pAsr.3535.usp45 derived plasmids are designed such that the Asr processed by *L. lactis* should be identical to that secreted by *L. citreum* NRRL B-1355 (SEQ ID NO:3) with the exception of the L544 substitution. The lysine residue at position 544 of the full length Asr protein (SEQ ID NO:2) is equivalent to the lysine residue at position 505 of the mature Asr protein (SEQ ID NO:3) and this residue is typically referred to as "L544", but indicates the same lysine residue. Thus, text describing a mutation of L544 in full-length Asr protein can also refer to a mutation of L505 in the mature Asr protein (lacking the signal sequence). Transformation into *L. lactis* LM0230 and enzyme production methods were similar to that previously described (Skory and Côté (2015), supra).

The glucosyltransferase gene responsible for isomelezitose production in *L. pseudomesenteroides* NRRL B-1297, previously classified as *L. mesenteroides* (Côté and Skory, Carbohydr. Res., (2017) 439:57-60), was identified by genomic sequencing using the Illumina Nextera XT DNA Library Preparation Kit and MiSeq Reagent Kit v3. A single gene (SEQ ID NO:13), gtfG, having similarity to other dextransucrases was PCR amplified to eliminate the predicted signal peptide (see, Table 1, underlined section of SEQ ID NO:15) and then used for Gibson assembly with the same pESUMO.Gib PCR fragment previously used. The lysine residue at position 417 of the full length GftG protein (SEQ ID NO:14) is equivalent to the lysine residue at position 380 of the mature GftG protein (SEQ ID NO:15) and this residue is typically referred to as "L417", but indicates the same lysine residue. Thus, text describing a mutation of L417 in full-length GftG protein can also refer to a mutation of L380 in the mature GftG protein (lacking the signal sequence). A L417P substitution was introduced into the resultant plasmid, pGtfG.SUMO as previously described. All plasmid modifications were confirmed by sequencing prior to utilization for enzyme studies.

Example 2

Analytical Methods

Glucansucrase activity was measured in one of two ways. Glucan formation was measured directly by monitoring the incorporation of $^{14}$C-glucose into methanol-insoluble glucan using a modification of the technique first described by Germaine, et al. (J. Dent. Res., (1974) 53:1355-60; Côté and Skory, (2012), supra). Alternatively, glucansucrase activity was determined indirectly by measuring the accumulation of fructose released under the same reaction conditions using the Megazyme D-Glucose/D-Fructose Assay Kit with a modified microplate protocol from those previously described (Vettori et al., Carbohydr. Res. (2011) 346:1077-82). Samples were removed at timed intervals throughout the enzyme reaction and then immediately diluted 20× in Megazyme Buffer #1 and heat denatured at 80° C. for 10 minutes. The activity of DsrI is almost non-existent in Buffer #1 and the enzyme is quickly heat inactivated at this temperature. Precipitated protein for the cooled sample was then removed by centrifugation and the remaining supernatant was then sequentially analyzed for glucose and fructose according to the manufacturer's recommendations. Formation of NADPH with this assay kit was monitored at $OD_{340}$ using a Biotek Synergy2 microplate reader to ensure that all conversion reactions were complete. The rate of fructose accumulation is representative of the initial rate of glucan biosynthesis. For most glucansucrases, the activities measured by both methods are nearly identical. However, for the DsrI L441 mutants, the amount of polysaccharide synthesized was significantly less than the amount of fructose released, as most of the glucosyl transfer reaction yielded isomelezitose, rather than glucan.

Reactions were also monitored chromatographically. Thin-layer chromatography was carried out using silica gel 60 plates with three solvent ascents of acetonitrile-water 4:1 (v/v). Sugars were made visible using N-(1-naphthyl) ethylenediamine dihydrochloride in 3% (v/v) sulfuric acid in methanol (Bounias, M., Anal. Biochem., (1980) 106:291-95). HPLC was performed using a Waters HPLC system with refractive index detector, fitted with a Regis Spherisorb S5NH column, 5 µm particle size, 4.6 mm×25 cm, eluted with acetonitrile-water 4:1 (v/v) at room temperature.

Isomelezitose was identified by chromatographic mobility, MALDI-TOFS, and $^1$H and $^{13}$C-NMR as previously described Côté et al., (2008), supra; Côté & Skory, (2017), supra).

Example 3

Reactions

All enzyme reactions were carried out at room temperature in 20 mM pH 5.5 sodium acetate buffer containing 2 mM calcium chloride and 1.5 mM sodium azide as a preservative. Sucrose concentration was varied between approximately 50 mM and 2.8M, depending on the experiment.

To compare the products from DsrI variants, 1 mL of an enzyme preparation was mixed with 6 mL of 1M sucrose (2 g sucrose). When all sucrose had been consumed, as determined by thin-layer chromatography, the water-insoluble glucan was removed by centrifugation, washed three times with water, once with 50% ethanol, once with absolute ethanol, and dried in vacuo at ~50° C. Weights were recorded. The water-soluble portion of each reaction mixture was mixed with four volumes of ethanol and chilled at −18° C. for several hours. The ethanol-precipitated polysaccharide was redissolved in water, precipitated a second time, and dried and weighed as above. The 80%-ethanol soluble fraction containing the residual oligosaccharides from the reaction mixtures was evaporated under a stream of nitrogen at ~60° C. to remove the ethanol. The resulting aqueous samples were chromatographed over a 3 cm×57 cm column of Dowex Monosphere 99CA/320 ion exchange resin, which is a strong cation-exchange resin in the $Ca^{2+}$ form. Isomelezitose and higher oligosaccharides were eluted immediately with water, whereas leucrose and fructose were retained and eluted in later fractions. The total yield of isomelezitose plus higher oligosaccharides was measured using the phenol-sulfuric acid method (DuBois et al., Anal. Chem., (1956) 28:350-6), using maltose as a standard. The oligosaccharide fraction was further analyzed by TLC as described above and the isomelezitose content determined densitometrically by scanning the TLC plate in reflectance mode on a desktop scanner (Epson Perfection V200 Photo) in black-and-white photographic mode. The image was saved as a 300 dpi jpeg file, which was subsequently analyzed densitometrically, using Un-Scan-It® software version 6.1 (Silk Scientific, Orem, Utah).

To calculate yield of isomelezitose from sucrose in a large scale reaction, 11 mL of L441E DsrI was incubated with 100 g of sucrose (0.3 moles) in 120 ml of buffer at room temperature (~22° C.) until all of the sucrose had been consumed (~40 hours). The entire reaction mixture was then chromatographed over BioGel P-2, eluting with water. Fractions containing isomelezitose, as determined by TLC, were combined and freeze-dried in vacuo at 50° C. overnight. Conditions were similar for analysis of DsrS L459P.

Example 4

Activity of DsrI Variants

Initial $^{14}$C-based glucansucrase assays of DsrI L441E enzyme preparations indicated much lower levels of glucan synthesis than the parent isolate and TLC analysis of the reactions showed that sucrose was being consumed at a rate comparable to wild-type DsrI. Fructose accumulation assays subsequently confirmed much higher activity than radioassays indicated. In one example, wild type DsrI showed 0.26 U/mL by radioassay and 0.38 U/mL based on the rate of fructose accumulation. Thin-layer chromatography of the wild-type enzyme reaction revealed that most of the difference could be accounted for by formation of leucrose. However, for the L441E mutant form of DsrI, radioassay measured only 0.07 U/mL of glucan synthase activity, but fructose accumulation analysis indicated 0.38 U/mL, similar to the wild-type. Furthermore, TLC actually showed less leucrose formation by L441E than by wild-type enzyme. Instead, the main products were fructose and an oligosaccharide with nearly the same chromatographic mobility as raffinose, suggesting it was a trisaccharide of similar structure. The unknown saccharide was isolated by gel-filtration chromatography over Bio-Gel P-2. NMR analysis was carried out as previously described (Côté et al., (2008), supra), and the resultant spectra matched previously published spectra for isomelezitose (Côté et al., (2008), supra; Inohara-Ochiai et al., supra; Shi et al., supra).

Figure 3:
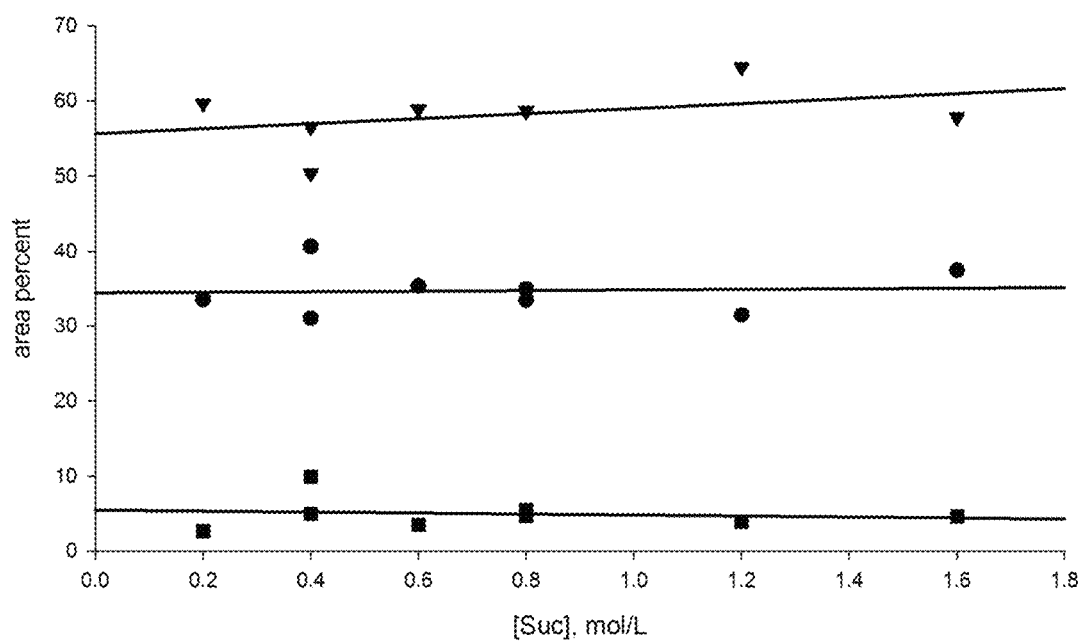
FIG. 3 provides a graph showing the effect of initial sucrose concentration on relative yields of fructose (•), isomelezitose (▼), and the disaccharides leucrose plus isomaltulose (■) by the L441E variant of B-1118 DsrI protein.

To determine the optimum sucrose concentration for maximum isomelezitose yields, a series of reactions was set up using 0.1 mL of L441E DsrI (0.18 U/mL glucan synthase activity) and 0.4 mL of sucrose solution of varying concentrations. When sucrose was completely consumed, as determined by TLC, the reaction mixtures were analyzed by HPLC. Fructose, isomelezitose, and leucrose plus isomaltulose (DP2) concentrations were measured. The results do not show any large effect of sucrose concentration on the relative ratios of each product (FIG. 2, fructose (•), isomelezitose (▼), and the disaccharides leucrose plus isomaltulose (●)). The major products at all concentrations were fructose and isomelezitose, in approximately equal proportions throughout the range of sucrose concentrations. This contrasts sharply with the products from wild-type DsrI, where isomelezitose concentrations were never more than a few percent of the total (FIG. 3 fructose (•), isomelezitose (▼), and the disaccharides leucrose plus isomaltulose (●)).

Figure 4:
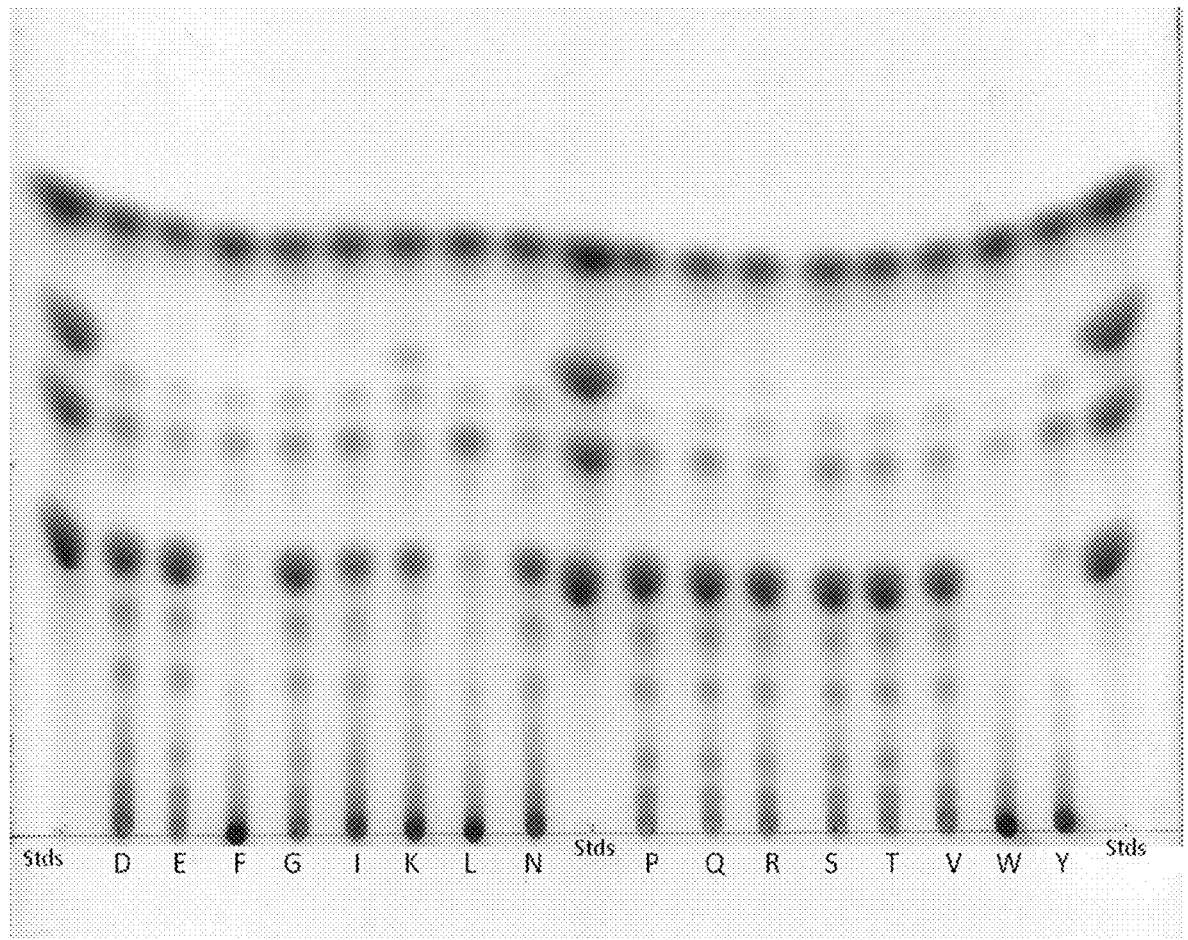
FIG. 4 provides a thin-layer chromatogram of various L441 mutant B-1118 DsrI reaction mixtures upon completion. Reactions contained 1 mL enzyme preparation and 6 mL 1M sucrose in buffer. Samples were diluted 10-fold with 50% ethanol, and 1 µL aliquots were chromatographed on a silica gel 60 plate for three ascents in acetonitrile-water 4:1 (v/v). Stds=standards: fructose, sucrose, leucrose, and raffinose (top to bottom). Isomelezitose migrates with a $R_f$ slightly greater than raffinose. No raffinose is present in DsrI samples. Letters indicate the amino acid at position L441. L=wild-type enzyme.

Several other amino acid substituents at L441 were also investigated by TLC of reaction mixtures after complete utilization of sucrose. Leucine (native enzyme), phenylalanine (L441F), tyrosine (L441Y), and tryptophan (L441W) made little or no isomelezitose. Those producing large amounts of isomelezitose were proline (L441P), glycine (L441P), serine (L441S), threonine (L441T), arginine (L441R), aspartate (L441D), glutamate (L441E), glutamine (L441Q), and valine (L441V). Intermediate amounts of isomelezitose were produced by L441 variants I (isoleucine), K (lysine) and N (asparagine). The reaction products of each of these are shown in the thin-layer chromatogram in FIG. 4.

Figure 5:
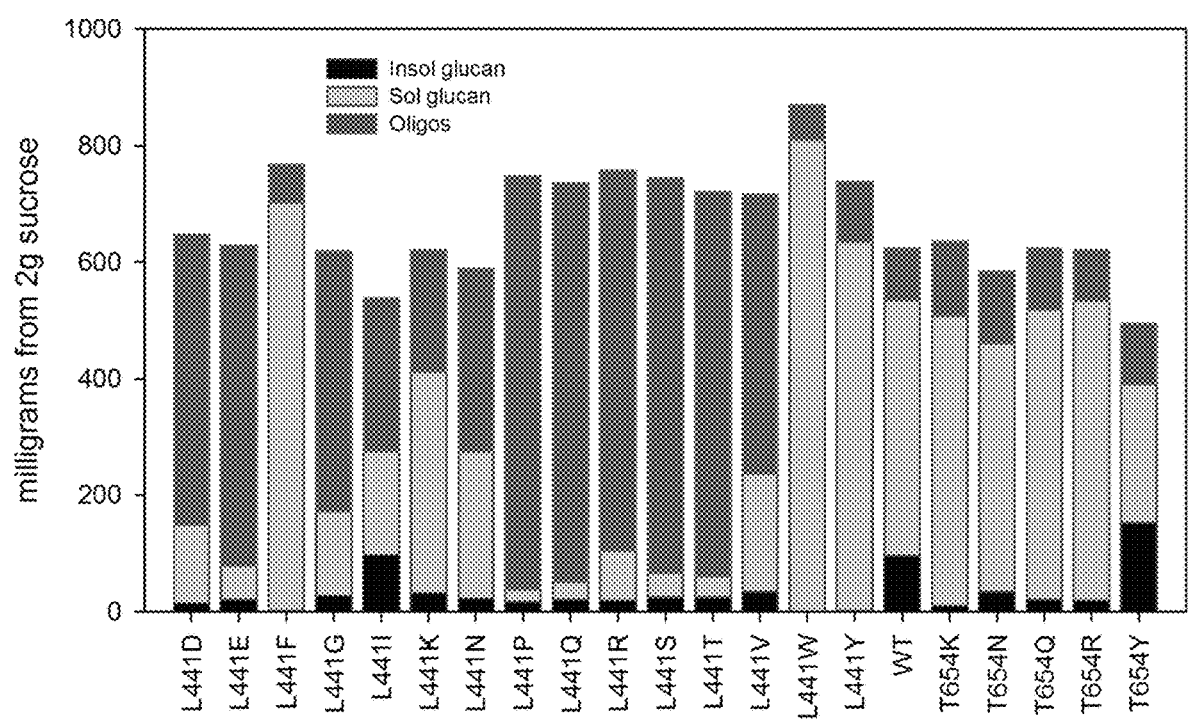
FIG. 5 provides a bar graph showing product distribution from various mutant DsrI reaction mixtures. Oligosaccharide is functionally defined here as the product fraction soluble in 80% ethanol after removal of fructose by Dowex chromatography. Water-soluble polysaccharide is functionally defined here as being initially soluble in reaction mixture, and precipitated at 80% ethanol concentration. Variants of the DsrI protein sequence are indicated. WT=wild-type enzyme.

After removal of fructose by Dowex chromatography, the oligosaccharide fraction was measured for total carbohydrate concentration (DuBois et al., supra). The bar graph in FIG. 5 shows the product distribution produced from 2 grams of sucrose by each DsrI variant. The oligosaccharide fraction was further analyzed by TLC, and the isomelezitose content determined densitometrically (FIG. 5). Variants L441P, Q, R, S, and T produced the greatest yields of isomelezitose. Variants L441F, W and Y produced little or no detectable amounts of isomelezitose, and the wild type produced only small amounts. The amount of isomelezitose formed by T654 mutants was similar to that formed by wild-type enzyme.

There were also higher oligosaccharides formed in most of the reactions, with degrees of polymerization (DP) ranging from tetrasaccharides (DP4) upwards to DP14, as measured by MALDI-TOFS and thin-layer chromatography. Treatment with endodextranase eliminated most of the higher (DP>4) oligosaccharides, indicating that they contained predominantly α(1→6)-linked D-glucopyranosyl residues. These are apparently acceptor products arising from glucosylation of isomelezitose. These soluble compounds may be considered higher DP oligosaccharides or very low-MW polysaccharides related to dextran.

The yield of isomelezitose from sucrose in a large scale reaction with L441E DsrI was 43 g (0.085 moles) isomelezitose from 100 g sucrose (0.3 moles), for a yield of 57%. The same reaction with L441P resulted in an isomelezitose yield of 51%.

Example 5

Activity of DsrS Variants

The wild type dextransucrase enzyme, DsrS, from *L. mesenteroides* NRRL B-1118 produces a water-soluble dextran, with predominantly α-1→6 linkages (Côté and Skory (2015), supra). Substitution of leucine 459 with a proline residue resulted in a mutant enzyme (L459P) that produced isomelezitose in yields comparable to those of L441E and L441P, but with slightly lower amounts of higher DP oligosaccharides. When using the DsrS L459P mutant enzyme secreted by *L. lactis*, the average yield on a 1 g scale was 40% (SD±5) from sucrose.

Example 6

Activity of Asr Variants

*L. citreum* alternansucrase (Asr) synthesizes an alternating α-1→3, α-1→6-linked D-glucan (Côté, G. L. (2002) "Alternan." Chapter 13 in Biopolymers, Vol. 5. A. Steinbüchel, Ed. Wiley-VCH, Weinheim, Germany. Pp. 323-350). Mutant enzymes were created by substitution of leucine 544 with glutamic acid, proline, arginine, or serine. All four were expressed from *L. lactis* extracellularly. Yields varied according to the amino acid substituent. Whereas the wild-type enzyme gave a 2.5% yield of isomelezitose, variant L544R gave a 1.9% yield, variant L544E gave a 6.8% yield, and variant L544S gave a 9.5% yield. The only alternansucrase variant tested that gave drastically higher yields of isomelezitose was L544P, which gave a 23% yield from sucrose.

Example 7

Activity of GtfI Variants

*S. sobrinus* 6715 is a cariogenic lactic acid bacterium that, like *L. mesenteroides* NRRL B-1118, produces both water-soluble and water-insoluble glucans (Hamada & Slade, Microbiol. Rev., (1980) 44:331-84). The GtfI enzyme is responsible for the synthesis of water-insoluble glucan similar to that of *L. mesenteroides* NRRL B-1118 in some respects (Shimamura et al., FEBS Lett., (1983) 157:79-84). Like other glucansucrases, it made isomelezitose in low yields (1.2% of theoretical maximum yield from sucrose) (Côté & Skory, (2017), supra). Mutant versions of GtfI produced enhanced amounts of isomelezitose, but the yields were much lower than those produced by the DsrI and DsrS mutants described herein. Respectively, the yields for GtfI mutants L350E, L350P, L350R and L350S as expressed from *E. coli* were 4.2%, 6.5%, 4.0% and 5.0%. It appeared that the lower yields were due in part to the formation of larger quantities of the higher DP oligosaccharides.

Example 8

Activity of GtfG Variants

Two glucansucrases that potentially could be responsible for isomelezitose production were identified from the *L. pseudomesenteroides* genome. One of them shared a 70% protein sequence identity by Lipman Pearson alignment with DsrE from *L. mesenteroides* NRRL B-1299, which catalyses the synthesis of α-1,6 and α-1,2 linkages from sucrose (Bozonnet et al., J. Bacteriol. (2002) 184:5753-61). The other protein, GtfG, was between 95-98% identical to a relatively new uncharacterized clade of glucosyltransferase from *L. pseudomesenteroides* (Pedersen et al., Genome Announc., (2014) 2:e00484-14; Frantzen et al., Front. Microbiol., (2017) 8:132). These proteins most closely align, 52-56% identity, with other glucansucrases that produce predominately soluble dextran where the majority of the glucosyl linkages are α-1,6. Variant GtfG L419P produced enhanced levels of isomelezitose relative to the unmodified enzyme. An overall yield of 10% based on sucrose was isolated chromatographically, whereas the wild type protein is not able to produce detectable levels of isomelezitose. Also observed was a series of oligosaccharides with chromatographic mobility similar to those observed for the other LxxxP variants described above.

Example 9

Summary of Results

We previously cloned DsrI from *L. mesenteroides* strain NRRL B-1118 (Côté & Skory, (2012), supra) that synthesizes a water-insoluble glucan, and demonstrated that amino acid substitutions within the active site of the enzyme at threonine residue 654 exhibit altered linkage specificity with respect to the ratios of α(1→3) and α(1→6) D-glucopyranosyl linkages (Côté & Skory, (2014), supra). Several of those strains produced higher proportions of α(1→3) linkages, but also gave lower yields of glucan. In an attempt to increase glucan yields, we subsequently decided to focus on amino acid substitution at leucine 441 with DsrI. The corresponding residue, Leu940, in a *L. reuteri* glucansucrase GTF180-AN, which produces a water-soluble dextran, was shown to be involved in acceptor substrate binding and is crucial to linkage specificity and glucan yields with this enzyme (Meng et al., Appl. Microbiol. Biotechnol., (2015) 99:5885-94; Meng et al., J. Biol. Chem. (2014) 289:32773-82). All amino acid substitutions in Leu940 resulted in an increased percentage of α(1→6), with a subsequent decrease in α(1→3) linkages. However, L940E and L940F substitutions also significantly shifted reaction specificity from oligosaccharide to polysaccharide synthesis (Meng et al., (2014), supra).

We initially focused on the equivalent L940E substitution in DsrI because this particular GTF180-ΔN mutant had the highest α(1→3) polysaccharide productivity compared to the other substitutions. When we performed the L441E substitution with DsrI (as described above), the resulting mutant form of the enzyme produced very little insoluble glucan. Instead, and unexpectedly, it produced isomelezitose in high yields. This contrasts with L940 substitutions in GTF180-ΔN that produced linear isomalto-oligosaccharides or very complex oligosaccharide mixtures, none of which were identified as isomelezitose (Meng et al., (2014), supra).

Figure 6:
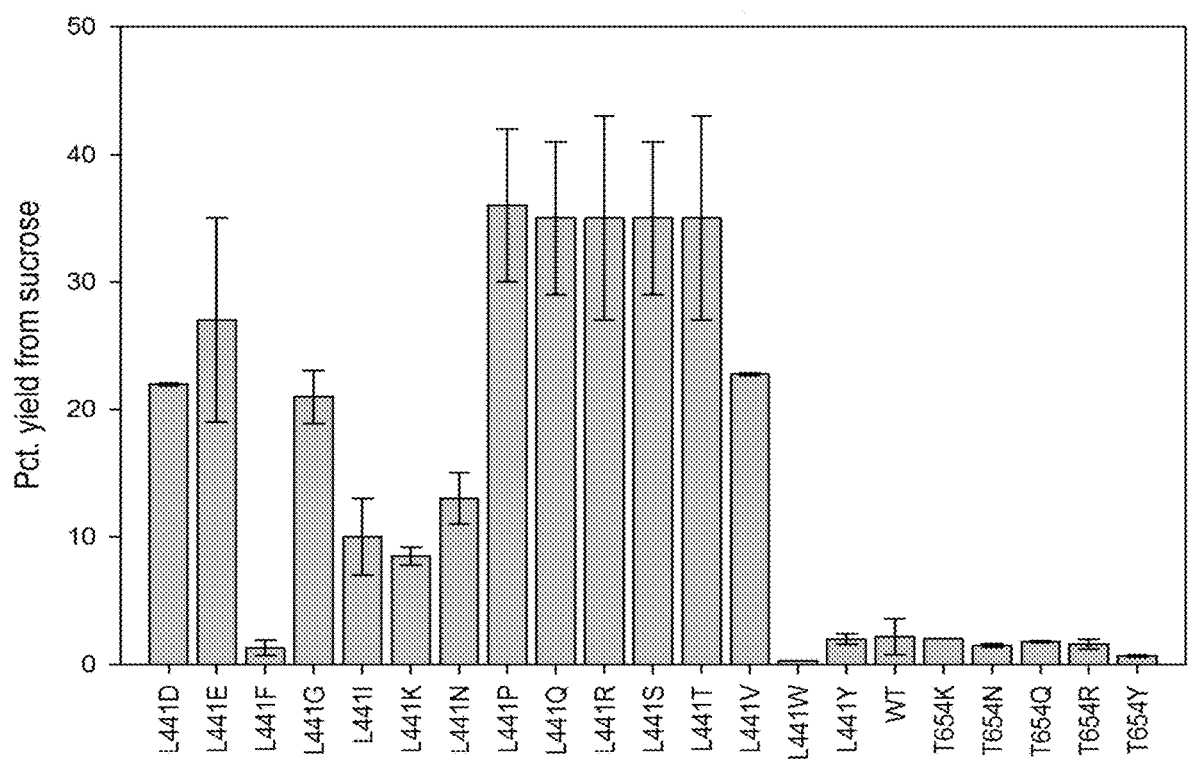
FIG. 6 provides a bar graph demonstrating the yield of isomelezitose produced by each variant from 2 grams of sucrose as determined by densitometric analysis of isomelezitose from TLC of oligosaccharides obtained from Dowex chromatography of 80% ethanol-soluble fraction. Variants of the DsrI protein sequence are indicated. WT=wild-type enzyme.

Isomelezitose has previously been described as minor product in reactions of alternansucrase using fructose as an acceptor Côté et al., (2008), supra) and *Weisella* dextransucrase using lactose as acceptor (Shi et al., supra). More recently, it was reported that isomelizitose is produced in trace amounts by a number of glucansucrases when sucrose is the only substrate added (Côté & Skory, (2017), supra). However, it was surprising to find that so many of the L441 variants of DsrI investigated produced high levels of isomelezitose. Besides the wild-type enzyme, the only other L441 variants studied which produced little or no isomelezitose were from the large aromatic amino acid substituents tryptophan, tyrosine and phenylalanine. Furthermore, these three variants also made little or no water-insoluble glucan (FIG. 6). Thus, of the sixteen L441 variants studied, only the wild-type DsrI enzyme produced large amounts of water-insoluble glucan and no isomelezitose.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A modified glucansucrase enzyme comprising a domain B motif, wherein the modified enzyme comprises an amino acid sequence that is at least 99% identical to:
   a. SEQ ID NO:5 or SEQ ID NO:6, wherein the leucine residue at position 441 of SEQ ID NO:5 or position 400 of SEQ ID NO:6 is substituted with an amino acid other than leucine;
   b. SEQ ID NO:8 or SEQ ID NO:9, wherein the leucine residue at position 459 of SEQ ID NO:8 or position 417 of SEQ ID NO:9 is substituted with an amino acid other than leucine;
   c. SEQ ID NO:2 or SEQ ID NO:3, wherein the leucine residue at position 544 of SEQ ID NO:2 or position 505 of SEQ ID NO:3 is substituted with an amino acid other than leucine;
   d. SEQ ID NO:11 or SEQ ID NO:12, wherein the leucine residue at position 350 of SEQ ID NO:11 or position 312 of SEQ ID NO:12 is substituted with an amino acid other than leucine; or
   e. SEQ ID NO:14 or SEQ ID NO:15, wherein the leucine residue at position 417 of SEQ ID NO:14 or position 380 of SEQ ID NO:15 is substituted with an amino acid other than leucine, and wherein the modified enzyme produces at least twice as much isomelezitose from sucrose as compared to the unmodified glucansucrase enzyme.

2. The modified glucansucrase of claim 1, wherein the substituting amino acid is proline.

3. The modified enzyme of claim 1, wherein the modified enzyme comprises an amino acid sequence that is at least 99% identical to SEQ ID NO:5 or SEQ ID NO:6, wherein the leucine residue at position 441 of SEQ ID NO:5 or position 400 of SEQ ID NO:6 is substituted with an amino acid other than leucine.

4. The modified enzyme of claim 3, wherein the substituting amino acid is arginine, asparagine, aspartic acid, glutamine, glutamic acid, glycine, isoleucine, lysine, proline, serine, threonine, or valine.

5. The modified enzyme of claim 1, wherein the modified enzyme comprises an amino acid sequence that is at least 99% identical to SEQ ID NO:8 or SEQ ID NO:9, wherein the leucine residue at position 459 of SEQ ID NO:8 or position 417 of SEQ ID NO:9 is substituted with an amino acid other than leucine.

6. The modified enzyme of claim 5, wherein the substituting amino acid is proline.

7. The modified enzyme of claim 1, wherein the modified enzyme comprises an amino acid sequence that is at least 99% identical to SEQ ID NO:2 or SEQ ID NO:3, wherein the leucine residue at position 544 of SEQ ID NO:2 or position 505 of SEQ ID NO:3 is substituted with an amino acid other than leucine.

8. The modified enzyme of claim 7, wherein the substituting amino acid is glutamic acid, proline, or serine.

9. The modified enzyme of claim 1, wherein the modified enzyme comprises an amino acid sequence that is at least 99% identical to SEQ ID NO:11 or SEQ ID NO:12, wherein the leucine residue at position 350 of SEQ ID NO:11 or position 312 of SEQ ID NO:12 is substituted with an amino acid other than leucine.

10. The modified enzyme of claim 9, wherein the substituting amino acid is arginine, glutamic acid, proline, or serine.

11. The modified enzyme of claim 1, wherein the modified enzyme comprises an amino acid sequence that is at least 99% identical to SEQ ID NO:14 or SEQ ID NO:15, wherein the leucine residue at position 417 of SEQ ID NO:14 or position 380 of SEQ ID NO:15 is substituted with an amino acid other than leucine.

12. The modified enzyme of claim 11, wherein the substituting amino acid is proline.

13. A method of producing isomelezitose comprising the steps of contacting a modified enzyme of any of claims 1-12 with a solution comprising a carbohydrate source, and allowing the modified enzyme to convert at least a portion of the carbohydrate source to isomelezitose.

14. The method of claim 13, further comprising the step of expressing the modified enzyme in a recombinant host cell.

15. The method of claim 14, further comprising the step of purifying the modified enzyme prior to contacting it with the carbohydrate source.

16. The method of claim 13, wherein the carbohydrate source comprises sucrose.

17. The method of claim 16, wherein the sucrose is in aqueous solution and is at a concentration of about 1.0 M.

* * * * *